United States Patent
Zha

(10) Patent No.: US 9,328,170 B2
(45) Date of Patent: May 3, 2016

(54) METHOD FOR PREPARING FC CONTAINING POLYPEPTIDES HAVING IMPROVED PROPERTIES

(75) Inventor: Dongxing Zha, Etna, NH (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 302 days.

(21) Appl. No.: 14/117,631

(22) PCT Filed: May 22, 2012

(86) PCT No.: PCT/US2012/038915
§ 371 (c)(1),
(2), (4) Date: Nov. 14, 2013

(87) PCT Pub. No.: WO2012/162277
PCT Pub. Date: Nov. 29, 2012

(65) Prior Publication Data
US 2014/0086916 A1    Mar. 27, 2014

Related U.S. Application Data

(60) Provisional application No. 61/489,743, filed on May 25, 2011.

(51) Int. Cl.
| | | |
|---|---|---|
| C07K 16/00 | (2006.01) |
| C12P 21/08 | (2006.01) |
| C07K 16/28 | (2006.01) |
| C07K 16/24 | (2006.01) |
| C07K 16/40 | (2006.01) |
| C07K 16/42 | (2006.01) |
| C07K 1/00 | (2006.01) |

(52) U.S. Cl.
CPC ........... *C07K 16/2851* (2013.01); *C07K 16/241* (2013.01); *C07K 16/28* (2013.01); *C07K 16/40* (2013.01); *C07K 16/42* (2013.01); *C07K 2317/41* (2013.01); *C07K 2317/524* (2013.01); *C07K 2317/71* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,439,196 A | 3/1984 | Higuchi |
| 4,447,224 A | 5/1984 | DeCant, Jr. et al. |
| 4,447,233 A | 5/1984 | Mayfield |
| 5,272,066 A | 12/1993 | Bergh et al. |
| 5,714,377 A | 2/1998 | Tanner et al. |
| 5,830,465 A | 11/1998 | Fukuda et al. |
| 6,156,881 A | 12/2000 | Seed et al. |
| 7,029,872 B2 | 4/2006 | Gerngross et al. |
| 7,198,921 B2 | 4/2007 | Miura et al. |
| 7,217,548 B2 | 5/2007 | Yoshida et al. |
| 7,244,601 B2 | 7/2007 | Gilbert et al. |
| 7,259,007 B2 | 8/2007 | Bobrowicz et al. |
| 7,326,681 B2 | 2/2008 | Gerngross et al. |
| 7,449,308 B2 | 11/2008 | Gerngross et al. |
| 7,863,020 B2 | 1/2011 | Hamilton |
| 7,931,895 B2 | 4/2011 | Beliard et al. |
| 2005/0170452 A1 | 8/2005 | Wildt et al. |
| 2005/0208617 A1 | 9/2005 | Bobrowicz et al. |
| 2005/0230042 A1 | 10/2005 | Hashimoto |
| 2005/0255489 A1 | 11/2005 | Pierce et al. |
| 2005/0260729 A1 | 11/2005 | Hamilton |
| 2006/0040353 A1 | 2/2006 | Davidson et al. |
| 2006/0211085 A1 | 9/2006 | Bobrowicz et al. |
| 2006/0234345 A1 | 10/2006 | Schwartz et al. |
| 2006/0275282 A1 | 12/2006 | Moore et al. |
| 2006/0286637 A1 | 12/2006 | Hamilton |
| 2007/0037248 A1 | 2/2007 | Bobrowicz et al. |
| 2007/0041979 A1 | 2/2007 | Raju et al. |
| 2007/0067855 A1 | 3/2007 | Jarvis et al. |
| 2007/0122403 A1 | 5/2007 | Dall'Acqua et al. |
| 2007/0184063 A1 | 8/2007 | Holgersson et al. |
| 2008/0112961 A1 | 5/2008 | Stavenhagen |
| 2008/0206246 A1 | 8/2008 | Ravetch et al. |
| 2008/0292621 A1 | 11/2008 | Lazar et al. |
| 2009/0215991 A1 | 8/2009 | Lazar et al. |
| 2010/0040601 A1 | 2/2010 | Cantin et al. |
| 2010/0137565 A1 | 6/2010 | Javaud et al. |
| 2010/0173323 A1 | 7/2010 | Strome et al. |

FOREIGN PATENT DOCUMENTS

| | | |
|---|---|---|
| EP | 2233500 | 9/2010 |
| WO | 9209694 | 6/1992 |
| WO | 9507020 | 3/1995 |
| WO | 96/21038 | 7/1996 |
| WO | 97/34631 | 9/1997 |
| WO | 0014251 | 3/2000 |
| WO | 0042072 | 7/2000 |
| WO | 0200856 | 1/2002 |
| WO | 2004029207 | 4/2004 |
| WO | 2004099249 | 11/2004 |

(Continued)

OTHER PUBLICATIONS

Van De Geijn, et al., Arthritis Research & Therapy vol. 11, 2009, R193-R203.
Abes et al., Pharmaceuticals vol. 3, 2010, pp. 146-157.
Sheeley et al., Analytical Biochemistry vol. 247 (1997) pp. 102-110.
Shibuya et al., Journal of Biological Chemistry, vol. 262, No. 4, (1987) pp. 1596-1601.
Anthony et al., Nature: Intravenous Gammaglobulin Suppresses Inflammation through a Novel TH2 Pathway (2011) pp. 1-5 (with Supplemental Information).
Dalziel et al., Glycoconjugate Journal, vol. 16 (1999) pp. 801-807.
Patel et al., Biochem. J. vol. 285 (1992) pp. 839-845.
Lifely et al., Glycobiology vol. 5, No. 8, (1995) pp. 813-822.

(Continued)

*Primary Examiner* — Chun Dahle
(74) *Attorney, Agent, or Firm* — Gloria Fuentes; Immac Thampoe

(57) ABSTRACT

The present invention is directed to methods and compositions for the production of Fc-containing polypeptides comprising mutations at positions 243, 264, 267 and 328 of the Fc region.

5 Claims, 9 Drawing Sheets

(56) References Cited

FOREIGN PATENT DOCUMENTS

| | | |
|---|---|---|
| WO | 2005033325 | 4/2005 |
| WO | 2005102387 | 11/2005 |
| WO | 2006019447 | 2/2006 |
| WO | 2006107990 | 10/2006 |
| WO | 2007/005786 | 1/2007 |
| WO | 2007/024743 | 3/2007 |
| WO | 2007061631 | 5/2007 |
| WO | 2007087420 | 8/2007 |
| WO | 2007120932 | 10/2007 |
| WO | 2008093165 | 8/2008 |
| WO | 2008-156676 | 12/2008 |
| WO | 2009/155513 | 12/2009 |
| WO | 2010033736 | 3/2010 |
| WO | 2010051391 | 5/2010 |
| WO | 2010/106180 | 9/2010 |
| WO | 2011/120134 | 10/2011 |
| WO | 2011/120135 | 10/2011 |
| WO | 2011149999 | 12/2011 |
| WO | 2013074598 | 5/2013 |

OTHER PUBLICATIONS

Anthony et al., J. Clin. Immunol. vol. 30, Suppl 1, (2010) pp. S9-S14.
Kuroda et al., The Journal of Immunology, (2005) pp. 1056-1061.
Stadlmann et al., J. Clin. Immunol. vol. 30 (Suppl 1), pp. S15-S19.
Stadlmann et al., Proteomics vol. 9 (2009) pp. 4143-4153.
Baumann et al., Immunol. Lett. vol. 131(1) (2010) pp. 59-66.
Cheong et al., J. Immunol. Methods vol. 360(1-2) (2010) pp. 66-75.
Raju et al., Biochemistry vol. 40 (2001) pp. 8868-8876.
Baumeister et al., Novel Human Expression System Glycoengineered for Optimal Glycosylation of Biotherapeutics (Supplement) (2006) pp. 2-6.
Baumeister et al., A Novel Human Expression System for Generating Glycoprotein with Higher Activity, Fully Human Glycosylation, and Optimized Sialylation, (2005) pp. 45-47.
Hossler et al., Glycobiology vol. 19, No. 9 (2009) pp. 936-949.
Durandy et al., British Society for Immunology, Clinical and Experimental Immunology, 158 (Suppl 1) (2009) pp. 2-13.
Reddy et al., The American Association of Immunologists (2000) pp. 1925-1933.
Kaneko et al., Science, vol. 313 (2006) pp. 670-673.
Anthony et al., Science, vol. 320 (2008) pp. 373-376.
Nimmerjahn et al., Immunity, vol. 23 (2005) pp. 41-51.
Duncan et al., Nature, vol. 332 (1988) pp. 563-564.
Armour et al., Eur. J. Immunol. vol. 29 (1999) pp. 2613-2624.
Presta, L. G., Current Opinion in Immunology vol. 20 (2008) pp. 460-470.
Nimmerjahn et al., JEM, vol. 204, No. 1 (2007) pp. 11-15.
Voynov et al., Dynamic Fluctuations of Protein-Carbohydrate Interactions Promote Protein Aggregation, vol. 4, Issue 12 (2009) pp. 1-10.
Umana et al., Nature Biotechnology vol. 17 (1999) pp. 176-180.
Lund et al., Eur. J. Biochem. vol. 267 (2000) pp. 7246-7256.
Nimmerjahn et al., Manuscript—Fc-receptor, ITP, SIGNR1, Sialic Acid, IVlg (2012) pp. 1-14.
Jefferis, R., Nature Biotechnology vol. 24 (2006) pp. 1230-1231.
Jassal et al., Biochemical and Biophysical Research Communication vol. 286 (2001) pp. 243-249.
Shields et al., The Journal of Biological Chemistry, vol. 276, No. 9 (2001) pp. 6591-6604.
Dimitrov et al., Nephrol Dial Transplant vol. 22 (2007) pp. 1301-1304.
Hutchins et al., Proc. Natl. Acad. Sci. USA vol. 92 (1995) pp. 11980-11984.
Radev et al., The Journal of Biological Chemistry, vol. 276, No. 19 (2001) pp. 16469-16477.
Lund et al., The American Association of Immunologists: Multiple Interactions of IgG with it's Core Oligosaccharide can Modulate Recognition by Complement and Human Fc gamma Receptor 1 and Influence the Synthesis of it's Oligosaccharide Chains (1996) pp. 4963-4969.
Jefferis et al., Immunology Letters vol. 54 (1996) pp. 101-104.
Leontyev et al., Transfusion (2011) pp. 1-7.
Debre et al., Infusion of Fc gamma Fragments for Treatment of Children wtih Acute Immune Thrombocytopenic Purpura, vol. 342 (1993) pp. 945-949.
Yasukawa et al., Glycobiology vol. 15, No. 9 (2005) pp. 827-837.
Vaccaro et al., Nature Biotechnology, vol. 23, No. 10 (2005) pp. 1283-1287.
Patel et al., The Journal of Immunology: Neonatal Fc Receptor Blockade by Fc Engineering Ameliorates Arthritis in a Murine Model (2011) pp. 1015-1022.
Li et al., Science, vol. 333 (2011) pp. 1030-1034.
Scallon et al., Molecular Immunology, vol. 44 (2007) pp. 1524-1534.
Jefferis, R., Trends in Pharmacological Sciences vol. 30, No. 7 (2009) pp. 356-362.
Barb et al., Biochemistry vol. 48(41) (2009) pp. 9705-9707.
Raju et al., Biochemical and Biophysical Research Communications vol. 341 (2006) pp. 797-803.
Guhr et al., Enrichment of Sialylated IgG by Lectin Fractionation Does Not Enhance the Efficacy of Immunoglobulin G in a Murine Model of Immune Thrombocytopenia, vol. 6 (2011) pp. 1-8.
Hamilton et al., Science, vol. 313, No. 8 (2006) pp. 1441-1443.
Rook et al., Journal of Autoimmunity vol. 4 (1991) pp. 779-794.
International Search Report—Mall Date—Jan. 25, 2013.
Dimitrov et al., Slalylated Therapeutic IgG: A Sweet Remedy for Inflammatory Diseases, Nephrol. Dial Transplant, vol. 22, 2007, pp. 1301-1304.
Supplementary European Search Report—mailing date Apr. 17, 2014.
Yu et al., J. Am. Chem. Soc. vol. 135, 2013, pp. 9723-9732.
Lussier et al., J. Biol. Chem. vol. 272(24) (1997) pp. 15527-15631.
Bretthauer, R. K., Methods in Molecular Biology, vol. 389; Pichia Protocols, Seconds Edition, pp. 107-118.
Willer et al., Curr. Opin. Struct. Biol. vol. 13, (2003) pp. 621-630.
Goto et al., Biosci. Biotechnol, Biochem. vol. 71(6), (2007) pp. 1415-1427.
Chu et al., Molecular Immunology vol. 45, pp. 3926-3933 (2008).
Umana et al., Nat. Biotech. vol. 17, pp. 176-180 (1999).
Shields et al., J. Blol. Chem. vol. 277, pp. 26733-26740 (2002).
Shinkawa et al., J. Biol. Chem. vol. 278, pp. 3466-3473 (2003).
Kaneko et al., Science, vol. 313 pp. 670-673 (2006).
Nimmerjahn & Ravetch, J. Exp. Med. vol. 204, pp. 11-15 (2007).
Hamilton et al., Science, vol. 313 (5792), pp. 1441-1443 (2006).
Schauer et al., Biochem. Society Transactions vol. 11, pp. 270-271 (1983).
Schauer et al., Glycobiology vol. 1 pp. 449-452 (1991).
Anthony et al., Science, vol. 320 pp. 373-376 (2008).
Wright & Morrison, Trends in Biotechnology, vol. 15, pp. 26-31 (1997).
Tao & Morrison, J. Immunol, vol. 143(8), pp. 2595-2601 (1989).
Lifely et al., Glycobiology, vol. 5, pp. 813-822 (1995).
Hodoniczky et al., Biotechnology Prog. vol. 21(6), pp. 1644-1652 (2005).
Jefferis et al., Chem. Immunol. vol. 65, pp. 111-128 (1997).
Li et al., Nat. Biotechnol. vol. 24(2) pp. 210-215 (2006).
Hossler et al., Biotechnology & Bioengineering, vol. 95(5) pp. 946-960 (2006).
Jefferis, R., Nature Biotech. vol. 24(10), pp. 1230-1231 (2006).
Lund et al., J. Immunol. vol. 157(11) pp. 4863-4969 (1996).
Choi et al., PNAS, USA, Vol, 100(9), pp. 5022-5027 (2003).
Cox et al., Nature Biotechnology, vol. 24, pp. 1591-1597 (2006).
Castilho et al., J. Biol. Chem vol. 285(21), pp. 15923-15930 (2010).
Harrison & Jarvis, Adv. Virus Res. vol. 68, pp. 159-191 (2006).
Lizak et al., Bioconjugate Chem, vol. 22, pp. 488-496 (2011).
Jacobs et al., Nature Protocols, vol. 4(1), pp. 58-70 (2009).
Gaulitzek et al., Biotechnol. Bioengin. vol. 103, pp. 1164-1175 (2009).
Jones et al., Biochim. Biophys. Acta, vol. 1726, pp. 121-137 (2005).
Idusogie et al., J. Immunology, vol. 164(8) pp. 4178-4184 (2000).
Sheilds et al., J. Biol. Chem. vol. 276, pp. 6591-6604 (2001).

(56) References Cited

OTHER PUBLICATIONS

Lee et al., J. Biol. Chem. vol. 264, pp. 13848-13855 (1989).
Bragonzi et al., Biochimica at Biopyhysica Acta (BBA), vol. 1474, pp. 273-282 (2000).
Dschietzig et al., Biochem. Biophys. Res. Comm. vol. 289, pp. 245-251 (2001).
Baert et al., New Engl. J. Med. vol. 348, pp. 601-608 (2003).
Milgrom et al., New Engl. J. Med. vol. 341, pp. 1966-1973 (1999).
Slamon et al., New Engl. Med. vol. 344, pp. 783-792 (2001).
Beniaminovitz et al., New Engl. J. Med. vol. 342, pp. 613-619 (2000).
Ghosh et al., New Engl. J. Med. vol. 348, pp. 24-32 (2003).
Lipsky et al., New Engl. J. Med. vol. 343, pp. 1594-1602 (2000).
Yang et al., New Engl. J. Med. vol. 349, pp. 427-434 (2003).
Herold et al., New Engl. J. Med. vol. 346, pp. 1692-1698 (2002).
Liu et al., J. Neurol. Neurosurg. Psych. vol. 67 pp. 451-456 (1999).
Portielji et al., Cancer Immunol. Immunother. vol. 52, pp. 133-144 (2003).
English language Abstract corresponding to CN2008/10007439.

SEQUENCE LISTING

<160> NUMBER OF SEQ ID NOS: 17

<210> SEQ ID NO 1
<211> LENGTH: 448
<212> TYPE: PRT
<213> ORGANISM: Artificial Sequence
<220> FEATURE:
<223> OTHER INFORMATION: Antibody heavy chain

<400> SEQUENCE: 1

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Asn Gly Gly Ala Ile Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Ser Gly Ile Ile Thr Glu Ile Ala Glu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
```

```
              260                 265                 270
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 2
<211> LENGTH: 214
<212> TYPE: PRT
<213> ORGANISM: Artificial Sequence
<220> FEATURE:
<223> OTHER INFORMATION: Antibody light chain

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Val Trp Tyr Gln Gln Lys Pro Gly Lys Ala Pro Lys Ala Leu Ile
        35                  40                  45

His Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Lys Thr Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
              180                 185                 190
Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 448
<212> TYPE: PRT
<213> ORGANISM: Artificial Sequence
<220> FEATURE:
<223> OTHER INFORMATION: Antibody heavy chain

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Asp Ile Asn Pro Asn Asn Gly Gly Ala Ile Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Ser Gly Ile Ile Thr Glu Ile Ala Glu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Ala Pro Pro Lys Pro Lys Asp Thr Leu Met Ile Ser
                245                 250                 255

Arg Thr Pro Glu Val Thr Cys Val Val Ala Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
```

```
                    325                 330                 335
Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 4
<211> LENGTH: 448
<212> TYPE: PRT
<213> ORGANISM: Artificial Sequence
<220> FEATURE:
<223> OTHER INFORMATION: Antibody heavy chain

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Phe Thr Asp Tyr
                20                  25                  30

Tyr Met Asn Trp Val Arg Gln Ala Pro Gly Gln Gly Leu Glu Trp Ile
            35                  40                  45

Gly Asp Ile Asn Pro Asn Asn Gly Gly Ala Ile Tyr Asn Gln Lys Phe
        50                  55                  60

Lys Gly Arg Ala Thr Leu Thr Val Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Thr Ser Gly Ile Ile Thr Glu Ile Ala Glu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Ala Pro Pro Lys Pro Lys Asp Thr Leu Met Ile Ser
```

```
                    245                 250                 255
Arg Thr Pro Glu Val Thr Cys Val Val Ala Asp Val Glu His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Phe Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 5
<211> LENGTH: 69
<212> TYPE: DNA
<213> ORGANISM: Artificial Sequence
<220> FEATURE:
<223> OTHER INFORMATION: signal sequence

<400> SEQUENCE: 5
gaattcgaaa cgatgagatt tccttcaatt tttactgctg ttttattcgc agcatcctcc      60
gcattagct                                                             69

<210> SEQ ID NO 6
<211> LENGTH: 19
<212> TYPE: PRT
<213> ORGANISM: Artificial Sequence
<220> FEATURE:
<223> OTHER INFORMATION: signal sequence

<400> SEQUENCE: 6

Met Arg Phe Pro Ser Ile Phe Thr Ala Val Leu Phe Ala Ala Ser Ser
1               5                   10                  15

Ala Leu Ala

<210> SEQ ID NO 7
<211> LENGTH: 223
<212> TYPE: PRT
<213> ORGANISM: Artificial Sequence
<220> FEATURE:
<223> OTHER INFORMATION: Fc domain

<400> SEQUENCE: 7

Thr Cys Pro Pro Cys Pro Ala Pro Glu Leu Leu Gly Gly Pro Ser Val
1               5                   10                  15
```

```
Phe Leu Ala Pro Pro Lys Pro Lys Asp Thr Leu Met Ile Ser Arg Thr
            20                  25                  30

Pro Glu Val Thr Cys Val Val Ala Asp Val Glu His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Phe Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

<210> SEQ ID NO 8
<211> LENGTH: 233
<212> TYPE: PRT
<213> ORGANISM: Artificial Sequence
<220> FEATURE:
<223> OTHER INFORMATION: Fc domain

<400> SEQUENCE: 8

Ala Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Ala Pro Pro Lys
            20                  25                  30

Pro Lys Asp Thr Leu Met Ile Ser Arg Thr Pro Glu Val Thr Cys Val
        35                  40                  45

Val Ala Asp Val Glu His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Phe Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160
```

Ser Asp Ile Ala Val Glu Trp Glu Ser Asn Gly Gln Pro Glu Asn Asn
            165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 9
<211> LENGTH: 450
<212> TYPE: PRT
<213> ORGANISM: Artificial Sequence
<220> FEATURE:
<223> OTHER INFORMATION: Antibody heavy chain

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Ala Asp Ser Val
    50                  55                  60

Lys Gly Arg Phe Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Ala Pro Pro Lys Pro Lys Asp Thr Leu Met
                245                 250                 255

Ile Ser Arg Thr Pro Glu Val Thr Cys Val Val Ala Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 10
<211> LENGTH: 218
<212> TYPE: PRT
<213> ORGANISM: Artificial Sequence
<220> FEATURE:
<223> OTHER INFORMATION: Antibody light chain

<400> SEQUENCE: 10

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

```
His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 11
<211> LENGTH: 450
<212> TYPE: PRT
<213> ORGANISM: Artificial Sequence
<220> FEATURE:
<223> OTHER INFORMATION: Antibody heavy chain

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Val Ser Gly Tyr Ser Ile Thr Ser Gly
            20                  25                  30

Tyr Ser Trp Asn Trp Ile Arg Gln Ala Pro Gly Lys Gly Leu Glu Trp
        35                  40                  45

Val Ala Ser Ile Thr Tyr Asp Gly Ser Thr Asn Tyr Ala Asp Ser Val
    50                  55                  60

Lys Gly Arg Phe Thr Ile Ser Arg Asp Asp Ser Lys Asn Thr Phe Tyr
65                  70                  75                  80

Leu Gln Met Asn Ser Leu Arg Ala Glu Asp Thr Ala Val Tyr Tyr Cys
                85                  90                  95

Ala Arg Gly Ser His Tyr Phe Gly His Trp His Phe Ala Val Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Ala Pro Pro Lys Pro Lys Asp Thr Leu Met
                245                 250                 255

Ile Ser Arg Thr Pro Glu Val Thr Cys Val Val Ala Asp Val Glu His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Phe Pro Ala Pro Ile
                325                 330                 335
```

```
Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly
    450

<210> SEQ ID NO 12
<211> LENGTH: 450
<212> TYPE: PRT
<213> ORGANISM: Artificial Sequence
<220> FEATURE:
<223> OTHER INFORMATION: Antibody heavy chain

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
                35                  40                  45

Ser Ala Ile Thr Trp Asn Ser Gly His Ile Asp Tyr Ala Asp Ser Val
            50                  55                  60

Glu Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
                210                 215                 220

Asp Lys Thr His Thr Cys Pro Pro Cys Pro Ala Pro Glu Leu Leu Gly
225                 230                 235                 240
```

```
Gly Pro Ser Val Phe Leu Ala Pro Pro Lys Pro Lys Asp Thr Leu Met
                245                 250                 255

Ile Ser Arg Thr Pro Glu Val Thr Cys Val Val Ala Asp Val Glu His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Phe Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 13
<211> LENGTH: 214
<212> TYPE: PRT
<213> ORGANISM: Artificial Sequence
<220> FEATURE:
<223> OTHER INFORMATION: Antibody light chain

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 14
<211> LENGTH: 233
<212> TYPE: PRT
<213> ORGANISM: Artificial Sequence
<220> FEATURE:
<223> OTHER INFORMATION: Fc domain

<400> SEQUENCE: 14

```
Ala Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Ala Pro Pro Lys
                20                  25                  30

Pro Lys Asp Thr Leu Met Ile Ser Arg Thr Pro Glu Val Thr Cys Val
            35                  40                  45

Val Ala Asp Val Ser His Glu Asp Pro Glu Val Lys Phe Asn Trp Tyr
        50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230
```

<210> SEQ ID NO 15
<211> LENGTH: 450
<212> TYPE: PRT
<213> ORGANISM: Artificial Sequence
<220> FEATURE:
<223> OTHER INFORMATION: Antibody heavy chain

```
<400> SEQUENCE: 15

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

-continued

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 16
<211> LENGTH: 450
<212> TYPE: PRT
<213> ORGANISM: Artificial Sequence
<220> FEATURE:
<223> OTHER INFORMATION: Antibody heavy chain

<400> SEQUENCE: 16

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Ala Pro Pro Lys Pro Lys Asp Thr Leu Met
                245                 250                 255

Ile Ser Arg Thr Pro Glu Val Thr Cys Val Val Ala Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 17
<211> LENGTH: 232
<212> TYPE: PRT
<213> ORGANISM: Artificial Sequence
<220> FEATURE:
<223> OTHER INFORMATION: Fc domain

<400> SEQUENCE: 17

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Ala Pro Pro Lys Pro
            20                  25                  30

Lys Asp Thr Leu Met Ile Ser Arg Thr Pro Glu Val Thr Cys Val Val
        35                  40                  45

Ala Asp Val Glu His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Phe Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210             215                 220
Ser Leu Ser Leu Ser Pro Gly Lys
225             230
```

US 9,328,170 B2

METHOD FOR PREPARING FC CONTAINING POLYPEPTIDES HAVING IMPROVED PROPERTIES

CROSS REFERENCE TO RELATED APPLICATIONS

This application is the National Stage of International Application No. PCT/US2012/038915 filed on May 22, 2012, which claims the benefit under 35 U.S.C. 119(e) of U.S. Provisional Application No. 61/489,743, filed May 25, 2011.

FIELD OF THE INVENTION

The present invention is directed to methods and compositions for the production of glycosylated proteins (glycoproteins) and, specifically, Fc-containing polypeptides which are useful as human or animal therapeutic agents.

BACKGROUND OF THE INVENTION

Monoclonal antibodies often achieve their therapeutic benefit through two binding events. First, the variable domain of the antibody binds a specific protein on a target cell. This is followed by recruitment of effector cells that bind to the constant region (Fc) of the antibody and destroy cells to which the antibody is bound.

The potency of an antibody (or other immunotherapeutic composition) depends on multiple mechanisms of action, including those mediated by effector cells expressing Fc receptors (FcRs). Fc receptors have activating or inhibitory functional roles and differ in their distribution among effector cells. Monocytes, macrophages, and neutrophils express both activating and inhibitory FcRs, whereas natural killer (NK) cells solely express the activating FcRIIIa. Thus, the degree to which an antibody (or other immunotherapeutic) can engage the various Fc receptors are important for clinical outcome.

Amino acid- and glyco-engineering of the antibody Fc domain are two ways to modify effector cell functions of antibodies and other immunothereapuetics. See, e.g., Chu et al., *Molecular Immunology* 45:3926-3933 (2008).

It would be desirable to engineer an antibody or Fc fusion protein comprising improved properties. For example, it would be desirable to engineer antibodies or other immunotherapeutics which bind to Fc gamma receptor IIB (CD32B), but which do not bind (or binds with reduced affinity) to Fc gamma receptor IIA (CD32A) and Fc gamma receptor IIIA (CD16A) and Fc gamma receptor I (CD64). Such antibodies would be characterized by their lack of (or a significant decrease in) effector function and increased anti-inflammatory properties.

The presence of N-glycosylation not only plays a role in the effector function of an antibody, the particular composition of the N-linked oligosaccharide is also important for its end function. For example, the lack of fucose or the presence of bisecting N-acetyl glucosamine has been positively correlated with the potency of the ADCC, Rothman (1989), Umana et al., *Nat. Biotech.* 17: 176-180 (1999), Shields et al., *J. Biol. Chem.* 277: 26733-26740 (2002), and Shinkawa et al., *J. Biol. Chem.* 278: 3466-3473 (2003). There is also evidence that sialylation in the Fc region is positively correlated with the anti-inflammatory properties of intravenous immunoglobulin (IVIG). See, e.g., Kaneko et al., *Science,* 313: 670-673, 2006; Nimmerjahn and Ravetch, *J. Exp. Med.,* 204: 11-15, 2007.

Given the utility of specific N-glycosylation in the function and potency of antibodies, methods for modifying the composition of N-linked oligosaccharides of antibodies and method of modifying the effector functions of antibodies and other immunotherapeutics would be desirable.

Yeast and other fungal hosts are important production platforms for the generation of recombinant proteins. Yeasts are eukaryotes and, therefore, share common evolutionary processes with higher eukaryotes, including many of the post-translational modifications that occur in the secretory pathway. Recent advances in glycoengineering have resulted in cell lines of the yeast strain *Pichia pastoris* with genetically modified glycosylation pathways that allow them to carry out a sequence of enzymatic reactions, which mimic the process of glycosylation in humans. See, for example, U.S. Pat. Nos. 7,029,872, 7,326,681 and 7,449,308 that describe methods for producing a recombinant glycoprotein in a lower eukaryote host cell that are substantially identical to their human counterparts. Human-like sialylated bi-antennary complex N-linked glycans like those produced in *Pichia pastoris* from the aforesaid methods have demonstrated utility for the production of therapeutic glycoproteins. Thus, a method for further modifying or improving the production of antibodies in yeasts such as *Pichia pastoris* would be desirable.

SUMMARY OF THE INVENTION

The invention relates to an Fc-containing polypeptide comprising mutations at amino acid positions 243, 264, 267 and 328 the Fc region, wherein the numbering is according to the EU index as in Kabat. In one embodiment, the mutations at positions 243 are selected from the group consisting of: F243A, F243G, F243S, F243T, F243V, F243L, F243I, F243D, F243Y, F243E, F243R, F243W and F243K; the mutations at position 264 are selected from the group consisting of: V264A, V264R, V264G, V264S, V264T, V264D, V264E, V264K, V264W, V264H, V264P, V264N, V264Q and V264L; the mutations at position 267 are selected from the group consisting of: S267D, S267Y, S267T; and the mutations at position 328 are selected from the group consisting of L328Y, L328W, L328H. In one embodiment, the mutations at positions 243 and 264 are selected from the group consisting of: F243A and V264A; F243Y and V264G; F243T and V264G; F243L and V264A; F243L and V264N; and F243V and V264G. In one embodiment, the mutations are F243A, V264A, S267E, and L328F.

In one embodiment, the Fc-containing polypeptide of the invention is an antibody or an antibody fragment. In one embodiment, the Fc-containing polypeptide of the invention is an antibody fragment comprising SEQ ID NO:7, SEQ ID NO:8 or SEQ ID NO:17. In another embodiment, the Fc-containing polypeptide of the invention is an antibody fragment consisting (or consisting essentially of) SEQ ID NO:7, SEQ ID NO:8 or SEQ ID NO:17.

In one embodiment, the Fc-containing polypeptide is an antibody comprising the heavy chain amino acid sequence of SEQ ID NO:4 or a variant thereof, and the light chain amino acid sequence of SEQ ID NO:2 or a variant thereof. In another embodiment, the Fc-containing polypeptide is an antibody comprising the heavy chain amino acid sequence of SEQ ID NO:11 or a variant thereof, and the light chain amino acid sequence of SEQ ID NO:10 or a variant thereof. In another embodiment, the Fc-containing polypeptide is an antibody comprising the heavy chain amino acid sequence of SEQ ID NO:12 or a variant thereof, and the light chain amino acid sequence of SEQ ID NO:13 or a variant thereof.

In some embodiments, the Fc-containing polypeptides of the invention comprise N-glycans comprising sialic acid (including NANA, NGNA, and analogs and derivatives thereof). In one embodiment, the N-glycans have a structure selected from SA$_{(1-4)}$Gal$_{(1-4)}$GlcNAc$_{(2-4)}$Man$_3$GlcNAc$_2$ or SAGalGlcNAcMan5GlcNAc$_2$. In one embodiment, the Fc-containing polypeptides of the invention comprise a mixture of α-2,3 and α-2,6 linked sialic acid. In another embodiment, the Fc-containing polypeptides of the invention comprise only α-2,6 linked sialic acid. In one embodiment, the Fc-containing polypeptides of the invention comprise α-2,6 linked sialic acid and comprise no detectable level of α-2,3 linked sialic acid. In one embodiment, the sialic acid is N-acetylneuraminic acid (NANA) or N-glycolylneuraminic acid (NGNA) or a mixture thereof. In another embodiment, the sialic acid is an analog or derivative of NANA or NGNA with acetylation at position 9 on the sialic acid. In one embodiment, the N-glycans on the Fc-containing polypeptides of the invention comprise NANA and no NGNA. In one embodiment, the N-glycans on the Fc-containing polypeptides of the invention comprise α-2,6 linked NANA (and no NGNA). In one embodiment, the Fc-containing polypeptide of the invention is an antibody or an antibody fragment comprising sialylated N-glycans comprising a structure selected from SA$_{(1-4)}$Gal$_{(1-4)}$GlcNAc$_{(2-4)}$Man$_3$GlcNAc$_2$ or SAGalGlcNAcMan5GlcNAc$_2$, wherein the sialic acid residues are via α-2,6 linkages. The N-glycans on the Fc-containing polypeptides of the invention can optionally comprise fucose. In one embodiment, the N-glycans on the Fc-containing polypeptides will comprise a mixture of fucosylated and non-fucosylated N-glycans. In another embodiment, the N-glycans on the Fc-containing polypeptides lack fucose.

In one embodiment, the Fc-containing polypeptide of the invention has one or more of the following properties when compared to a parent Fc-containing polypeptide: (i) reduced effector function; (ii) increased anti-inflammatory properties; (iii) increased binding to a lectin (e.g., CD22 (Siglec 2)); (iv) reduced binding to FcγRIIa; (v) increased binding to FcγRIIb; (vi) reduced binding to FcγRIIIa; and (v) reduced binding to FcγRIIIb.

In one embodiment, the Fc-containing polypeptide of the invention has reduced effector function when compared to a parent Fc-containing polypeptide. In one embodiment, the effector function is ADCC. In another embodiment, the effector function is CDC. In another embodiment, the effector function is ADCP.

In one embodiment, the Fc-containing polypeptide of the invention has reduced ADCC activity when compared to a parent Fc-containing polypeptide. In another embodiment, the Fc-containing polypeptide has at least a 100 fold reduction in ADCC activity. In another embodiment, the Fc-containing polypeptide has at least a 500 fold reduction in ADCC activity. In another embodiment, the Fc-containing polypeptide has at least a 1000 fold reduction in ADCC activity. In one embodiment, the Fc-containing polypeptide has no detectable ADCC activity.

In another embodiment, the Fc-containing polypeptide of the invention has reduced ADCP activity when compared to a parent Fc-containing polypeptide. In one embodiment, the Fc-containing polypeptide has no detectable ADCP activity.

In another embodiment, the Fc-containing polypeptide of the invention has reduced CDC activity when compared to a parent Fc-containing polypeptide. In one embodiment, the Fc-containing polypeptide has at least 100 fold reduction in CDC activity. In one embodiment, the Fc-containing polypeptide has no detectable CDC activity.

In one embodiment, the Fc-containing polypeptide of the invention has the following properties when compared to a parent Fc-containing polypeptide: (i) reduced binding to FcγRIIa; (ii) increased binding to FcγRIIb; (iii) reduced binding to FcγRIIIa; and (iv) reduced binding to FcγRIIIb.

In one embodiment, the Fc-containing polypeptide of the invention has the following properties when compared to a parent Fc-containing polypeptide: (i) reduced binding to FcγRIIa; (ii) increased binding to FcγRIIb; and (iii) reduced binding to FcγRIIIa.

In one embodiment, an Fc-containing polypeptide of the invention will have no detectable binding to FcγRIIa, FcγRIIIa or FcγRIIIb. In one embodiment, an Fc-containing polypeptide of the invention will have no detectable binding to FcγRIIa, FcγRIIIa FcγRIIIb, when such binding is detected using an ELISA assay.

In one embodiment, the Fc-containing polypeptide of the invention binds FcγRIIb with an increase affinity of at least 2 fold when compared to a parent Fc-containing polypeptide. In one embodiment, the Fc-containing polypeptide of the invention binds FcγRIIb with an increase affinity of at least 4 fold when compared to a parent Fc-containing polypeptide.

In one embodiment, the Fc-containing polypeptide of the invention has increased anti-inflammatory properties compared to a parent Fc-containing polypeptide.

In a one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation. In another embodiment, the parent Fc-containing polypeptide comprises a F243A mutation and a V264A mutation.

The invention also comprises a method for producing an Fc-containing polypeptide in a host cell comprising: (i) providing a host cell that has been genetically engineered to produce an Fc-containing polypeptide, wherein the host cell comprises a nucleic acid encoding mutations at amino acid positions 243, 264, 267 and 328 of the Fc region, wherein the numbering is according to the EU index as in Kabat; (ii) culturing the host cell under conditions which cause expression of the Fc-containing polypeptide; and (iii) isolating the Fc-containing polypeptide from the host cell. In one embodiment, the nucleic acid encodes mutations positions 243 are selected from the group consisting of: F243A, F243G, F243S, F243T, F243V, F243L, F243I, F243D, F243Y, F243E, F243R, F243W and F243K; the mutations at position 264 are selected from the group consisting of: V264A, V264R, V264G, V264S, V264T, V264D, V264E, V264K, V264W, V264H, V264P, V264N, V264Q and V264L; the mutations at position 267 are selected from the group consisting of: S267D, S267Y, S267T; and the mutations at position 328 are selected from the group consisting of L328Y, L328W, L328H. In one embodiment, the mutations at positions 243 and 264 are selected from the group consisting of: F243A and V264A; F243Y and V264G; F243T and V264G; F243L and V264A; F243L and V264N; and F243V and V264G. In one embodiment, the nucleic acid encodes the mutations F243A, V264A, S267E, and L328F. In one embodiment, the Fc-containing polypeptide of the invention is an antibody or an antibody fragment.

In one embodiment, the Fc-containing polypeptide of the invention is an antibody fragment comprising SEQ ID NO:7, SEQ ID NO:8 or SEQ ID NO:17. In another embodiment, the Fc-containing polypeptide of the invention is an antibody fragment consisting (or consisting essentially of) SEQ ID NO:7, SEQ ID NO:8 or SEQ ID NO:17.

In one embodiment, the method for producing an Fc-containing polypeptide is carried out in a mammalian cell. In another embodiment, the method for producing an Fc-containing polypeptide is carried out in a plant cell. In another embodiment, the method for producing an Fc-containing polypeptide is carried out in bacteria. In another embodiment, the method for producing an Fc-containing polypeptide is carried out in an insect cell. In another embodiment, the method for producing an Fc-containing polypeptide is carried out in a lower eukaryotic cell. In another embodiment, the method for producing an Fc-containing polypeptide is carried out in a yeast cell. In one embodiment, the method for producing an Fc-containing polypeptide is carried out in *Pichia pastoris*.

In one embodiment, the Fc-containing polypeptide produced by the claimed method comprises N-glycans comprising sialic acid (including NANA, NGNA, and analogs and derivatives thereof). In one embodiment, the Fc-containing polypeptide produced by the claimed method has an N-glycan composition in which at least 40 mole %, 70 mole % or 90 mole % of the N-glycans on the Fc-containing polypeptide are sialylated (have a structure selected from $SA_{(1-4)}Gal_{(1-4)}GlcNAc_{(2-4)}Man_3GlcNAc_2$ or $SAGalGlcNAcMan5GlcNAc_2$). In one embodiment, the Fc-containing polypeptides produced by the claimed method comprise a mixture of α-2,3 and α-2,6 linked sialic acid. In another embodiment, the Fc-containing polypeptides comprise only α-2,6 linked sialic acid. In one embodiment, the Fc-containing polypeptides of the invention comprise α-2,6 linked sialic acid and comprise no detectable level of α-2,3 linked sialic acid. In one embodiment, the sialic acid is N-acetylneuraminic acid (NANA) or N-glycolylneuraminic acid (NGNA) or a mixture thereof. In another embodiment, the sialic acid is an analog or derivative of NANA or NGNA with acetylation at position 9 on the sialic acid. In one embodiment, the N-glycans on the Fc-containing polypeptides produced by the claimed method comprise NANA and no NGNA. In one embodiment, the N-glycans on the Fc-containing polypeptides of the invention comprise α-2,6 linked NANA (and no NGNA).

In one embodiment, the Fc-containing polypeptide of the invention is an antibody or an antibody fragment comprising sialylated N-glycans comprising a structure selected from $SA_{(1-4)}Gal_{(1-4)}GlcNAc_{(2-4)}Man_3GlcNAc_2$ or $SAGalGlcNAcMan5GlcNAc_2$, wherein the sialic acid residues are via α-2,6 linkages.

The N-glycans on the Fc-containing polypeptides produced by the claimed method can optionally comprise fucose. In one embodiment, the N-glycans on the Fc-containing polypeptides produced by the claimed method comprise a mixture of fucosylated and non-fucosylated N-glycans. In one embodiment, the N-glycans on the Fc-containing polypeptides produced by the claimed method lack fucose.

In one embodiment, the Fc-containing polypeptide produced by the claimed method has an N-glycan composition in which the amount and percentage of total sialylated N-glycans is increased relative to a parent Fc-containing polypeptide.

In some embodiments, the Fc-containing polypeptide produced by the claimed method has one or more of the following properties when compared to a parent Fc-containing polypeptide: (i) reduced effector function; (ii) increased anti-inflammatory properties; (iii) increased binding to a lectin (e.g., CD22 (Siglec 2)); (iv) reduced binding to FcγRIIa; (v) increased binding to FcγRIIb; (vi) reduced binding to FcγRIIIa; and (v) reduced binding to FcγRIIIb.

In one embodiment, the Fc-containing polypeptide produced by the claimed method has reduced effector function when compared to a parent Fc-containing polypeptide. In one embodiment, the effector function is ADCC. In another embodiment, the effector function is CDC. In another embodiment, the effector function is ADCP.

In one embodiment, the Fc-containing polypeptide of the invention has reduced ADCC activity when compared to a parent Fc-containing polypeptide. In another embodiment, the Fc-containing polypeptide has at least a 100 fold reduction in ADCC activity. In another embodiment, the Fc-containing polypeptide has at least a 500 fold reduction in ADCC activity. In another embodiment, the Fc-containing polypeptide has at least a 1000 fold reduction in ADCC activity. In one embodiment, the Fc-containing polypeptide has no detectable ADCC activity.

In another embodiment, the Fc-containing polypeptide of the invention has reduced ADCP activity when compared to a parent Fc-containing polypeptide. In one embodiment, the Fc-containing polypeptide has no detectable ADCP activity.

In another embodiment, the Fc-containing polypeptide produced by the claimed method has reduced CDC activity when compared to a parent Fc-containing polypeptide. In one embodiment, the Fc-containing polypeptide has at least 100 fold reduction in CDC activity. In one embodiment, the Fc-containing polypeptide has no detectable CDC activity.

In one embodiment, the Fc-containing polypeptide produced by the claimed method the following properties when compared to a parent Fc-containing polypeptide: (i) reduced binding to FcγRIIa; (ii) increased binding to FcγRIIb; (iii) reduced binding to FcγRIIIa; and (v) reduced binding to FcγRIIIb.

In one embodiment, the Fc-containing polypeptide produced by the claimed method the following properties when compared to a parent Fc-containing polypeptide: (i) reduced binding to FcγRIIa; (ii) increased binding to FcγRIIb; and (iii) reduced binding to FcγRIIIa.

In one embodiment, an Fc-containing polypeptide of the invention will have no detectable binding to FcγRIIa, FcγRIIIa, or FcγRIIIb. In one embodiment, an Fc-containing polypeptide of the invention will have no detectable binding to FcγRIIa, FcγRIIIa or FcγRIIIb, when such binding is detected using an ELISA assay.

In one embodiment, the Fc-containing polypeptide of the invention binds FcγRIIb with an increase affinity of at least 2 fold when compared to a parent Fc-containing polypeptide. In one embodiment, the Fc-containing polypeptide of the invention binds FcγRIIb with an increase affinity of at least 4 fold when compared to a parent Fc-containing polypeptide.

In one embodiment, the Fc-containing polypeptide produced by the claimed method has increased anti-inflammatory properties relative to a parent Fc-containing polypeptide.

In a one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation. In another embodiment, the parent Fc-containing polypeptide comprises a F243A mutation and a V264A mutation.

The invention also comprises a method of reducing the effector function of an Fc-containing polypeptide, comprising introducing mutations at positions 243, 264, 267 and 328 of a parent Fc-containing polypeptide, wherein said Fc containing polypeptide has decreased effector function when compared to the parent Fc-containing polypeptide, wherein the numbering is according to the EU index as in Kabat. In a one embodiment, the Fc-containing polypeptide comprises mutations F243A, V264A, S267E, and L328F. In one embodiment, the effector function is ADCC. In another embodiment, the effector function is CDC. In one embodiment, the effector function is ADCP. In one embodiment, the Fc-containing polypeptide of the invention is an antibody or an antibody fragment. In one embodiment, the Fc-containing polypeptide is an antibody fragment comprising SEQ ID NO:7. In another embodiment, the Fc-containing polypeptide is an antibody fragment comprising SEQ ID NO:8. In another embodiment, the Fc-containing polypeptide is an antibody fragment comprising SEQ ID NO:17. In another embodiment, the Fc-containing polypeptide is an antibody fragment consisting (or consisting essentially of) SEQ ID NO:7, SEQ ID NO:8 or SEQ ID NO:17. In one embodiment, the Fc-containing polypeptide of the invention comprises sialylated N-glycans comprising a structure selected from $SA_{(1-4)}Gal_{(1-4)}GlcNAc_{(2-4)}Man_3GlcNAc_2$ or $SAGalGlcNAcMan5GlcNAc_2$, wherein the sialic acid residues are linked via α-2,6 linkages. In a one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation. In another embodiment, the parent Fc-containing polypeptide comprises a F243A mutation and a V264A mutation.

The invention also comprises a method of increasing the anti-inflammatory properties of an Fc-containing polypeptide, comprising introducing mutations at positions 243, 264, 267 and 328 of a parent Fc-containing polypeptide, wherein the numbering is according to the EU index as in Kabat, wherein said Fc containing polypeptide has increased anti-inflammatory activity when compared to a parent Fc-containing polypeptide. In a one embodiment, the Fc-containing polypeptide comprises mutations F243A, V264A, S267E, and L328F. In one embodiment, the Fc-containing polypeptide of the invention is an antibody or an antibody fragment. In one embodiment, the Fc-containing polypeptide is an antibody or antigen binding fragment thereof that binds to an antigen selected from the group consisting of: APRIL, INF-α, BAFF (BLys), CD22, TNF-α, IL-1, IL-2, IL-4, IL-5, IL-6, IL-8, IL-9, IL-10, IL-12, IL-15, IL-17, IL-18, IL-20, IL-21, IL-22, IL-23, IL-23R, IL-25, IL-27, IL-33, CD2, CD4, CD11A, CD14, CD18, CD19, CD23, CD25, CD38, CD40, CD40L, CD20, CD52, CD64, CD80, CD147, CD200, CD200R, TSLP, TSLPR, PD-1, PDL1, CTLA4, VLA-4, VEGF, PCSK9, α4β7-integrin, E-selectin, Fact II, ICAM-3, beta2-integrin, IFNγ, C5, CBL, LCAT, CR3, MDL-1, GITR, ADDL, CGRP, TRKA, IGF1R, RANKL, GTC, or the receptor for any of the above mentioned molecules. In a one embodiment, the Fc-containing polypeptide will bind to TNF-α. In another one embodiment, the Fc-containing polypeptide will bind to Her2. In another one embodiment, the Fc-containing polypeptide will bind to PCSK9. In one embodiment, the Fc-containing polypeptide of the invention is an antibody fragment comprising SEQ ID NO:7. In another embodiment, the Fc-containing polypeptide of the invention is an antibody fragment comprising SEQ ID NO:8. In another embodiment, the Fc-containing polypeptide of the invention is an antibody fragment comprising SEQ ID NO:17. In another embodiment, the Fc-containing polypeptide of the invention is an antibody fragment consisting (or consisting essentially of) SEQ ID NO:7 or SEQ ID NO:8 or SEQ ID NO:17. In one embodiment, the Fc-containing polypeptide of the invention is an antibody or an antibody fragment comprising sialylated N-glycans comprising a structure selected from $SA_{(1-4)}Gal_{(1-4)}GlcNAc_{(2-4)}Man_3GlcNAc_2$ or $SAGalGlcNAcMan5GlcNAc_2$, wherein the sialic acid residues are linked via α-2,6 linkages. In one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation. In another embodiment, the parent Fc-containing polypeptide comprises a F243A mutation and a V264A mutation.

The invention also comprises a method of increasing the anti-inflammatory properties of an Fc-containing polypeptide comprising: selecting a parent Fc-containing polypeptide that is useful in treating inflammation (for example, an antibody or immunoadhesin that binds to an antigen that is involved in inflammation) and introducing mutations at positions 243, 264, 267 and 328 of the Fc-region, wherein the numbering is according to the EU index as in Kabat, wherein the Fc-containing polypeptide has increased anti-inflammatory activity when compared to the parent Fc-containing polypeptide. In one embodiment, the nucleic acid encodes the mutations F243A, V264A, S267E, and L328F. In one embodiment, the Fc-containing polypeptide of the invention is an antibody or an antibody fragment. In one embodiment, the Fc-containing polypeptide is an antibody or antigen binding fragment thereof that binds to an antigen selected from the group consisting of: APRIL, INF-α, BAFF (BLys), CD22, TNF-α, IL-1, IL-2, IL-4, IL-5, IL-6, IL-8, IL-9, IL-10, IL-12, IL-15, IL-17, IL-18, IL-20, IL-21, IL-22, IL-23, IL-23R, IL-25, IL-27, IL-33, CD2, CD4, CD11A, CD14, CD18, CD19, CD23, CD25, CD38, CD40, CD40L, CD20, CD52, CD64, CD80, CD147, CD200, CD200R, TSLP, TSLPR, PD-1, PDL1, CTLA4, VLA-4, VEGF, PCSK9, α4β7-integrin, E-selectin, Fact II, ICAM-3, beta2-integrin, IFNγ, C5, CBL, LCAT, CR3, MDL-1, GITR, ADDL, CGRP, TRKA, IGF1R, RANKL, GTC, or the receptor for any of the above mentioned molecules. In a one embodiment, the Fc-containing polypeptide will bind to TNF-α. In another one embodiment, the Fc-containing polypeptide will bind to Her2. In another one embodiment, the Fc-containing polypeptide will bind to PCSK9. In one embodiment, the Fc-containing polypeptide is an antibody fragment comprising SEQ ID NO:7. In another embodiment, the Fc-containing polypeptide is an antibody fragment comprising SEQ ID NO:8. In another embodiment, the Fc-containing polypeptide of the invention is an antibody fragment comprising SEQ ID NO:17. In another embodiment, the Fc-containing polypeptide is an antibody fragment consisting (or consisting essentially of) SEQ ID NO:7 or SEQ ID NO:8 or SEQ ID NO:17. In one embodiment, the Fc-containing polypeptide of the invention is an antibody or an antibody fragment comprising sialylated N-glycans comprising a structure selected from $SA_{(1-4)}Gal_{(1-4)}GlcNAc_{(2-4)}Man_3GlcNAc_2$ or $SAGalGlcNAcMan5GlcNAc_2$, wherein the sialic acid residues are linked via α-2,6 linkages. In one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation. In another embodiment, the parent Fc-containing polypeptide comprises a F243A mutation and a V264A mutation.

The invention also comprises a method of treating an inflammatory condition in a subject in need thereof comprising: administering to the subject a therapeutically effective amount of an Fc-containing polypeptide comprising mutations at positions 243, 264, 267 and 328, wherein the numbering is according to the EU index as in Kabat. In one embodiment, the Fc-containing polypeptide decreases the expression of a gene selected from the group consisting of: IL-10, IL-6, RANKL, TRAP, ATP6v0d2, MDL-1, DAP12, CD11b, TIMP-1, MMP9, CTSK, PU-1, MCP1, MIP1α, Cxcl1-Groa, CXcl2-Grob, CD18, TNF, FcγRI, FcγRIIb, FcγRIII and FcγRIV. In a one embodiment, the Fc-containing polypeptide comprises mutations F243A, V264A, S267E, and L328F. In one embodiment, the Fc-containing polypeptide is administered parenterally. In one embodiment, the Fc-containing polypeptide is administered subcutaneously. In one embodiment, the Fc-containing polypeptide is an antibody or antigen binding fragment thereof. In one embodiment, the Fc-containing polypeptide is an antibody or antigen binding fragment thereof that is useful in treating an inflammatory condition. In one embodiment, the antibody or antigen binding fragment thereof binds to an antigen selected from the group consisting of: APRIL, INF-α, BAFF (BLys), CD22, TNF-α, IL-1, IL-2, IL-4, IL-5, IL-6, IL-8, IL-9, IL-10, IL-12, IL-15, IL-17, IL-18, IL-20, IL-21, IL-22, IL-23, IL-23R, IL-25, IL-27, IL-33, CD2, CD4, CD11A, CD14, CD18, CD19, CD23, CD25, CD38, CD40, CD40L, CD20, CD52, CD64, CD80, CD147, CD200, CD200R, TSLP, TSLPR, PD-1, PDL1, CTLA4, VLA-4, VEGF, PCSK9, α4β7-integrin, E-selectin, Fact II, ICAM-3, beta2-integrin, IFNγ, C5, CBL, LCAT, CR3, MDL-1, GITR, ADDL, CGRP, TRKA, IGF1R, RANKL, GTC, or the receptor for any of the above mentioned molecules. In one embodiment, the Fc-containing polypeptide will bind to TNF-α. In another embodiment, the Fc-containing polypeptide will bind to Her2. In another embodiment, the Fc-containing polypeptide will bind to PCSK9. In one embodiment, the Fc-containing polypeptide is an antibody fragment comprising SEQ ID NO:7. In another embodiment, the Fc-containing polypeptide is an antibody fragment comprising SEQ ID NO:8. In another embodiment, the Fc-containing polypeptide of the invention is an antibody fragment comprising SEQ ID NO:17. In another embodiment, the Fc-containing polypeptide is an antibody fragment consisting (or consisting essentially of) SEQ ID NO:7 or SEQ ID NO:8 or SEQ ID NO:17. In one embodiment, the Fc-containing polypeptide of the invention is an antibody or an antibody fragment comprising sialylated N-glycans comprising a structure selected from $SA_{(1-4)}Gal_{(1-4)}GlcNAc_{(2-4)}Man_3GlcNAc_2$ or $SAGalGlcNAcMan5GlcNAc_2$, wherein the sialic acid residues are linked via α-2,6 linkages.

Another invention disclosed herein relates to a pharmaceutical composition comprising an Fc-containing polypeptide, wherein at least 70%, at least 80% or at least 90% of the N-glycans on the Fc-containing polypeptide comprise an oligosaccharide structure selected from the group consisting of $SA_{(1-4)}Gal_{(1-4)}GlcNAc_{(2-4)}Man_3GlcNAc_2$ and $SAGalGlcNAcMan5GlcNAc_2$, wherein the Fc-containing polypeptide comprises mutations at amino acid positions 243, 264, 267 and 328 of the Fc region, wherein the numbering is according to the EU index as in Kabat. In one embodiment, the mutations are F243A, V264A, S267E, and L328F. In one embodiment, the sialylated N-glycans comprise a mixture of α-2,3 and α-2,6 linked sialic acid. In another embodiment, the sialylated N-glycans comprise only α-2,6 linked sialic acid. In another embodiment, the sialylated N-glycans comprise α-2,6 linked sialic acid and comprise no detectable level of α-2,3 linked sialic acid. In one embodiment, the sialic acid is N-acetylneuraminic acid (NANA) or N-glycolylneuraminic acid (NGNA) or a mixture thereof. In another embodiment, the sialic acid is an analog or derivative of NANA or NGNA with acetylation at position 9 on the sialic acid. In one embodiment, the N-glycans on the Fc-containing polypeptides comprise NANA and no NGNA. In one embodiment, the Fc-containing polypeptide is an antibody fragment comprising SEQ ID NO:7. In another embodiment, the Fc-containing polypeptide is an antibody fragment comprising SEQ ID NO:8. In another embodiment, the Fc-containing polypeptide of the invention is an antibody fragment comprising SEQ ID NO:17. In another embodiment, the Fc-containing polypeptide is an antibody fragment consisting (or consisting essentially of) SEQ ID NO:7 or SEQ ID NO:8 or SEQ ID NO:17.

Another invention disclosed herein relates to a pharmaceutical composition comprising an Fc-containing polypeptide, wherein at least 70%, 80% or 90% of the N-glycans on the Fc-containing polypeptide comprise an oligosaccharide structure selected from the group consisting of $SA_{(1-4)}Gal_{(1-4)}GlcNAc_{(2-4)}Man_3GlcNAc_2$ and $SAGalGlcNAcMan5GlcNAc_2$, wherein the sialic acid residues are attached exclusively via an α-2,6 linkage, wherein the N-glycans lack fucose, and wherein the Fc-containing polypeptide comprises mutations at amino acid positions 243, 264, 267 and 328 of the Fc region, wherein the numbering is according to the EU index as in Kabat. In one embodiment, the mutations are F243A, V264A, S267E, and L328F. In one embodiment, the sialylated N-glycans comprise a mixture of α-2,3 and α-2,6 linked sialic acid. In another embodiment, the sialylated N-glycans comprise only α-2,6 linked sialic acid. In another embodiment, the sialylated N-glycans comprise α-2,6 linked sialic acid and comprise no detectable level of α-2,3 linked sialic acid. In one embodiment, the sialic acid is N-acetylneuraminic acid (NANA) or N-glycolylneuraminic acid (NGNA) or a mixture thereof. In another embodiment, the sialic acid is an analog or derivative of NANA or NGNA with acetylation at position 9 on the sialic acid. In one embodiment, the N-glycans on the Fc-containing polypeptides comprise NANA and no NGNA. In one embodiment, the N-glycans on the Fc-containing polypeptides of the invention comprise α-2,6 linked NANA (and no NGNA). In one embodiment, the Fc-containing polypeptide is an antibody fragment comprising SEQ ID NO:7. In another embodiment, the Fc-containing polypeptide is an antibody fragment comprising SEQ ID NO:8. In another embodiment, the Fc-containing polypeptide of the invention is an antibody fragment comprising SEQ ID NO:17. In another embodiment, the Fc-containing polypeptide is an antibody fragment consisting (or consisting essentially of) SEQ ID NO:7 or SEQ ID NO:8 or SEQ ID NO:17.

The invention also comprises an Fc-containing polypeptide comprising a heavy chain and a light chain, wherein the heavy chain comprises the amino acid sequence of SEQ ID NO:4 or a variant thereof and the light chain comprises the amino acid sequence of SEQ ID NO:2 or a variant thereof, wherein the variant comprises one or more of the following properties when compared to an antibody comprising the heavy chain amino acid sequence of SEQ ID NO:1 and the light chain amino acid sequence of SEQ ID NO:2: (i) reduced effector function; (ii) increased anti-inflammatory properties; (iii) increased binding to a lectin (e.g., CD22 (Siglec 2)); (iv) reduced binding to FcγRIIa; (v) increased binding to FcγRIIb; (vi) reduced binding to FcγRIIIa; and (vii) reduced binding to FcγRIIIb. In one embodiment, the variant comprises up to 0, 1, 2, 3, 4, 5, 6, 7, 8, 9, 10 or more conservative or non conservative amino acid substitutions. In one embodiment, the variant comprises at least 75%, 80%, 85%, 90%, 95%, 98% or 99% sequence identity with the claimed sequence.

The invention also comprises an Fc-containing polypeptide comprising a heavy chain and a light chain, wherein the heavy chain comprises the amino acid sequence of SEQ ID NO:4 or a variant thereof and the light chain comprises the amino acid sequence of SEQ ID NO:2 or a variant thereof, wherein the variant comprises one or more of the following properties when compared to an antibody comprising the heavy chain amino acid sequence of SEQ ID NO:3 and the light chain amino acid sequence of SEQ ID NO:2: (i) reduced effector function; (ii) increased anti-inflammatory properties; (iii) increased binding to a lectin (e.g., CD22 (Siglec 2)); (iv) reduced binding to FcγRIIa; (v) increased binding to FcγRIIb; (vi) reduced binding to FcγRIIIa; and (vii) reduced binding to FcγRIIIb. In one embodiment, the variant comprises up to 0, 1, 2, 3, 4, 5, 6, 7, 8, 9, 10 or more conservative or non conservative amino acid substitutions. In one embodiment, the variant comprises at least 75%, 80%, 85%, 90%, 95%, 98% or 99% sequence identity with the claimed sequence.

DETAILED DESCRIPTION OF THE INVENTION

Definitions

Figure 1:
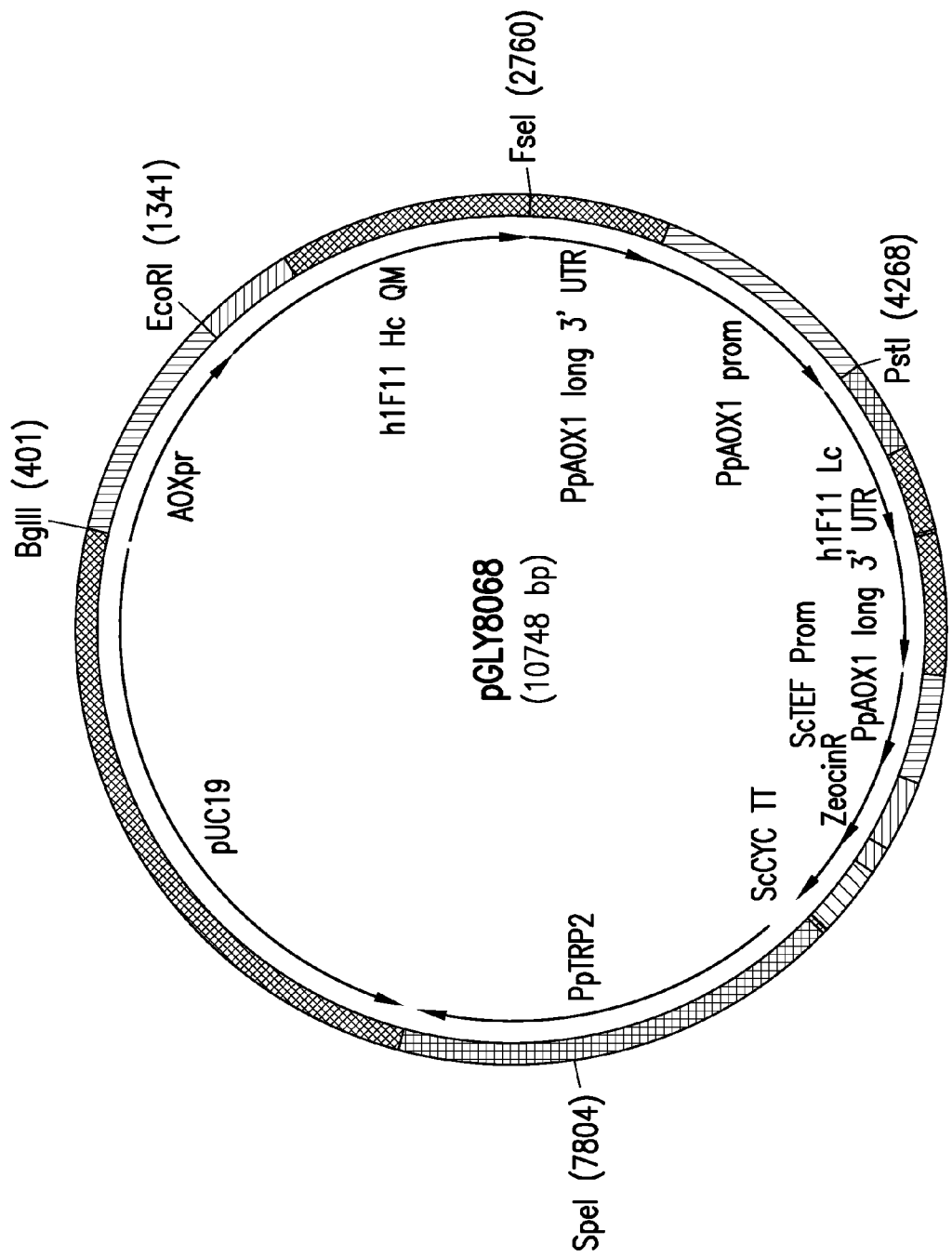
FIG. 1 is a graphic representation of pGLY8068, the expression plasmid for antibody 1F11 F243A/V264A/S267E/L328F. Both heavy and light chains were under the control of a methanol inducible promoter, AOX1. The PpTrp2 gene was the locus applied to integrate the entire cassette. With the exception of the mutations on the heavy chain, the expression plasmid structure was the same for the wild type, the double mutein (F243A/V264A), and the quadruple mutein (F243A/V264A/S267E/L328F) IF11 expression plasmids.

The term "G0" when used herein refers to a complex bi-antennary oligosaccharide without galactose or fucose, GlcNAc₂Man₃GlcNAc₂.

The term "G1" when used herein refers to a complex bi-antennary oligosaccharide without fucose and containing one galactosyl residue, GalGlcNAc₂Man₃GlcNAc₂.

The term "G2" when used herein refers to a complex bi-antennary oligosaccharide without fucose and containing two galactosyl residues, Gal₂GlcNAc₂Man₃GlcNAc₂.

The term "G0F" when used herein refers to a complex bi-antennary oligosaccharide containing a core fucose and without galactose, GlcNAc₂Man₃GlcNAc₂F.

The term "G1F" when used herein refers to a complex bi-antennary oligosaccharide containing a core fucose and one galactosyl residue, GalGlcNAc₂Man₃GlcNAc₂F.

The term "G2F" when used herein refers to a complex bi-antennary oligosaccharide containing a core fucose and two galactosyl residues, Gal₂GlcNAc₂Man₃GlcNAc₂F.

The term "Man5" when used herein refers to the oligosaccharide structure shown as

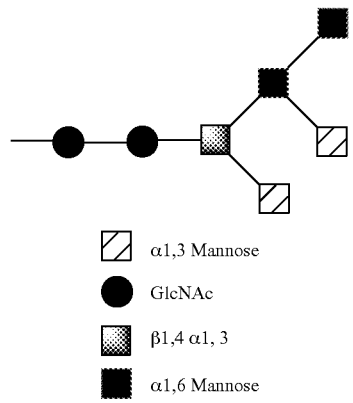

α1,3 Mannose
GlcNAc
β1,4 α1,3
α1,6 Mannose

The term "M4" as used herein refers to the oligosaccharide Man4GlcNAc2.

The term "M5" as used herein refers to the oligosaccharide Man5GlcNAc2.

The term "A1" as used herein refers to the oligosaccharide NANA1Gal2GlcNAc2Man3GlcNAc2.

The term "A1H" as used herein refers to the oligosaccharide NANA1GalMan(3-5)GlcNAc2.

The term "A2" as used herein refers to the oligosaccharide NANA2Gal2GlcNAc2Man3GlcNAc2.

The term "GFI 5.0" when used herein refers to glycoengineered *Pichia pastoris* strains that produce glycoproteins having predominantly Gal₂GlcNAc₂Man₃GlcNAc₂ N-glycans.

The term "GFI 6.0" when used herein refers to glycoengineered *Pichia pastoris* strains that produce glycoproteins having predominantly NANA₂Gal₂GlcNAc₂Man₃GlcNAc₂ N-glycans.

The term "GS5.0", when used herein refers to the N-glycosylation structure Gal₂GlcNAc₂Man₃GlcNAc₂.

The term "GS5.5", when used herein refers to the N-glycosylation structure NANAGal₂GlcNAc₂Man₃GlcNAc₂, which when produced in *Pichia pastoris* strains to which α2,6 sialyl transferase has been glycoengineered result in α2,6-linked sialic acid and which when produced in *Pichia pastoris* strains to which α2,3 sialyl transferase has been glycoengineered result in α2,3-linked sialic acid.

The term "GS6.0", when used herein refers to the N-glycosylation structure NANA₂Gal₂GlcNAc₂Man₃GlcNAc₂, which when produced in *Pichia pastoris* strains to which α2,6 sialyl transferase has been glycoengineered result in α2,6-linked sialic acid and which when produced in *Pichia pastoris* strains to which α2,3 sialyl transferase has been glycoengineered result in α2,3-linked sialic acid.

The term "wild type" or "wt" when used herein in connection to a *Pichia pastoris* strain refers to a native *Pichia pastoris* strain that has not been subjected to genetic modification to control glycosylation.

The term "antibody", when used herein refers to an immunoglobulin molecule capable of binding to a specific antigen through at least one antigen recognition site located in the variable region of the immunoglobulin molecule. As used herein, the term encompasses not only intact polyclonal or monoclonal antibodies, consisting of four polypeptide chains, i.e. two identical pairs of polypeptide chains, each pair having one "light" chain (LC) (about 25 kDa) and one "heavy" chain (HC) (about 50-70 kDa), but also fragments thereof, such as Fab, Fab', F(ab')$_2$, Fv, single chain (ScFv), mutants thereof, fusion proteins comprising an antibody portion, and any other modified configuration of an immunoglobulin molecule that comprises an antigen recognition site and at least the portion of the $C_H2$ domain of the heavy chain immunoglobulin constant region which comprises an N-linked glycosylation site of the $C_H2$ domain, or a variant thereof. As used herein the term includes an antibody of any class, such as IgG (for example, IgG1, IgG2, IgG3 or IgG4), IgM, IgA, IgD and IgE, respectively.

The term "consensus sequence of $C_H2$" when used herein refers to the amino acid sequence of the $C_H2$ domain of the heavy chain constant region containing an N-linked glycosylation site which was derived from the most common amino acid sequences found in $C_H2$ domains from a variety of antibodies.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The Fc region of an immunoglobulin comprises two constant domains, CH2 and CH3, and can optionally comprise a hinge region. In one embodiment, the Fc region comprises the amino acid sequence of SEQ ID NO:7. In one embodiment, the Fc region comprises the amino acid sequence of SEQ ID NO:8. In another embodiment, the Fc-containing polypeptide of the invention is an antibody fragment comprising SEQ ID NO:17. In another embodiment, the Fc region comprises the amino acid sequence of SEQ ID NO:7 or SEQ ID NO:8, with the addition of a lysine (K) residue at the 3' end. The Fc region contains a single N-linked glycosylation site in the CH2 domain that corresponds to the Asn297 site of a full-length heavy chain of an antibody.

The term "Fc-containing polypeptide" refers to a polypeptide, such as an antibody or immunoadhesin, which comprises an Fc region. This term encompasses polypeptides comprising or consisting of (or consisting essentially of) an Fc region. Polypeptides comprising an Fc region can be generated by papain digestion of antibodies or by recombinant DNA technology.

The term "parent antibody", "parent immunoglobulin" or "parent Fc-containing polypeptide" when used herein refers to an antibody or Fc-containing polypeptide which lacks the Fc region mutations disclosed herein. A parent Fc-containing polypeptide may comprise a native sequence Fc region or an Fc region with pre-existing amino acid sequence modifications. A native sequence Fc region comprises an amino acid sequence identical to the amino acid sequence of an Fc region found in nature. Native sequence Fc regions include the native sequence human IgG1 Fc region, the native sequence human IgG2 Fc region, the native sequence human IgG3 Fc region and the native sequence human IgG4 Fc region as well as naturally occurring variants thereof. When used as a comparator, a parent antibody or a parent Fc-containing polypeptide can be expressed in any cell. In one embodiment, the parent antibody or a parent Fc-containing polypeptide is expressed in the same cell as the Fc-containing polypeptide of the invention.

As used herein, the term "immunoadhesin" designates antibody-like molecules which combine the "binding domain" of a heterologous "adhesin" protein (e.g. a receptor, ligand or enzyme) with an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The term "ligand binding domain" as used herein refers to any native cell-surface receptor or any region or derivative thereof retaining at least a qualitative ligand binding ability of a corresponding native receptor. In a specific embodiment, the receptor is from a cell-surface polypeptide having an extracellular domain that is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor which predispose the mammal to the disorder in question. In one embodiment, the disorder is cancer. Methods of making immunoadhesins are well known in the art. See, e.g., WO00/42072.

The antibody referred to as "1F11" refers to a humanized anti-PCSK9 antibody having the amino acid sequence disclosed in Example 2.

The term "Herceptin®" refers to the commercial anti-Her2 antibody produced in CHO cells also known as rastuzumab.

The term "Fc mutein antibody" when used herein refers to an antibody comprising one of the single Fc muteins or the double Fc mutein described herein.

The term "Fc mutein" when used herein refers to an Fc-containing polypeptide in which one or more point mutations have been made to the Fc region.

The term "Fc mutation" when used herein refers to a mutation made to the Fc region of an Fc-containing polypeptide. Examples of such a mutation include the F243A, V264A, S267E, or L328F mutations described herein.

The term "F243A" refers to a mutation from F (wild-type) to A at position 243 of the Fc region of the antibody heavy chain. The term "V264A" refers to a mutation from V (wild-type) to A at position 264 of the Fc region of the antibody heavy chain. The term "S267E" refers to a mutation from S (wild-type) to E at position 267 of the Fc region of the antibody heavy chain. The term "L328F" refers to a mutation from L (wild-type) to F at position 328 of the Fc region of the antibody heavy chain. The position 243, 264, 267 and 328 represent the amino acid positions in the CH2 domain of the Fc region of the antibody heavy chain as according to the EU number system.

The term "double Fc mutein" or "DM" when used herein refers to an Fc-containing polypeptide comprising mutations at positions 243 and 264 of the Fc region. The term "F243A/V264A" refers to a double Fc mutein comprising the two specified mutations.

The term "quadruple Fc mutein" or "QM" when used herein refers to an Fc-containing polypeptide comprising mutations at positions 243, 264, 267 and 328 of the Fc region of the antibody heavy chain. The term "F243A/V264A/S267E/L328F" refers to a quadruple Fc mutein comprising the four specified mutations.

Throughout the present specification and claims, the numbering of the residues in an immunoglobulin heavy chain or an Fc-containing polypeptide is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

The term "effector function" as used herein refers to a biochemical event that results from the interaction of an antibody Fc region with an Fc receptor or ligand. Exemplary "effector functions" include C1q binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions can be assessed using various assays known in the art.

The term "glycoengineered *Pichia pastoris*" when used herein refers to a strain of *Pichia pastoris* that has been genetically altered to express human-like N-glycans. For example, the GFI 5.0, GFI 5.5 and GFI 6.0 strains described above.

The terms "N-glycan", "glycoprotein" and "glycoform" when used herein refer to an N-linked oligosaccharide, e.g., one that is attached by an asparagine-N-acetylglucosamine linkage to an asparagine residue of a polypeptide. Predominant sugars found on glycoproteins are glucose, galactose, mannose, fucose, N-acetylgalactosamine (GalNAc), N-acetylglucosamine (GlcNAc) and sialic acid (SA, including NANA, NGNA and derivatives and analogs thereof, including acetylated NANA or acetylated NGNA). In glycoengineered *Pichia pastoris*, sialic acid is exclusively N-acetyl-neuraminic acid (NANA) (Hamilton et al., *Science* 313 (5792): 1441-1443 (2006)). N-glycans have a common pentasaccharide core of $Man_3GlcNAc_2$, wherein "Man" refers to mannose, "Glc" refers to glucose, "NAc" refers to N-acetyl, and GlcNAc refers to N-acetylglucosamine. N-glycans differ with respect to the number of branches (antennae) comprising peripheral sugars (e.g., GlcNAc, galactose, fucose and sialic acid) that are added to the $Man_3GlcNAc_2$ ("Man3") core structure which is also referred to as the "trimannose core", the "pentasaccharide core" or the "paucimannose core". N-glycans are classified according to their branched constituents (e.g., high mannose, complex or hybrid).

As used herein, the term "sialic acid" or "SA" refers to any member of the sialic acid family, including without limitation: N-acetylneuraminic acid (Neu5Ac or NANA), N-glycolylneuraminic acid (NGNA) and any analog or derivative thereof (including those arising from acetylation at any position on the sialic acid molecule). Sialic acid is a generic name for a group of about 30 naturally occurring acidic carbohydrates that are essential components of a large number of glycoconjugates. Schauer, *Biochem. Society Transactions*, 11, 270-271 (1983). Sialic acids are usually the terminal residue of the oligosaccharides. N-acetylneuraminic acid (NANA) is the most common sialic acid form and N-glycolylneuraminic acid (NGNA) is the second most common form. Schauer, *Glycobiology*, 1, 449-452 (1991). NGNA is widespread throughout the animal kingdom and, according to species and tissue, often constitutes a significant proportion of the glycoconjugate-bound sialic acid. Certain species such as chicken and man are exceptional, since they lack NGNA in normal tissues. Corfield, et al., Cell Biology Monographs, 10, 5-50 (1982). In human serum samples, the percentage of sialic acid in the form of NGNA is reported to be 0.01% of the total sialic acid. Schauer, "Sialic Acids as Antigenic Determinants of Complex Carbohydrates", found in The Molecular Immunology of Complex Carbohydrates, (Plenum Press, New York, 1988).

The term "human-like N-glycan", as used herein, refers to the N-linked oligosaccharides which closely resemble the oligosaccharides produced by non-engineered, wild-type human cells. For example, wild-type *Pichia pastoris* and other lower eukaryotic cells typically produce hypermannosylated proteins at N-glycosylation sites. The host cells described herein produce glycoproteins (for example, antibodies) comprising human-like N-glycans that are not hypermannosylated. In some embodiments, the host cells of the present invention are capable of producing human-like N-glycans with hybrid and/or complex N-glycans. The specific type of "human-like" glycans present on a specific glycoprotein produced from a host cell of the invention will depend upon the specific glycoengineering steps that are performed in the host cell.

The term "high mannose" type N-glycan when used herein refers to an N-glycan having five or more mannose residues.

The term "complex" type N-glycan when used herein refers to an N-glycan having at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). As an example, when a N-glycan comprises a bisecting GlcNAc on the trimannose core, the structure can be represented as $Man_3GlcNAc_2(GlcNAc)$ or $Man_3GlcNAc_3$. When an N-glycan comprises a core fucose attached to the trimannose core, the structure may be represented as $Man_3GlcNAc_2(Fuc)$. Complex N-glycans may also have multiple antennae on the "trimannose core," often referred to as "multiple antennary glycans."

The term "hybrid" N-glycan when used herein refers to an N-glycan having at least one GlcNAc on the terminal of the 1,3 mannose arm of the trimannose core and zero or more than one mannose on the 1,6 mannose arm of the trimannose core.

When referring to "mole percent" of a glycan present in a preparation of a glycoprotein, the term means the molar percent of a particular glycan present in the pool of N-linked oligosaccharides released when the protein preparation is treated with PNGase and then quantified by a method that is not affected by glycoform composition, (for instance, labeling a PNGase released glycan pool with a fluorescent tag such as 2-aminobenzamide and then separating by high performance liquid chromatography or capillary electrophoresis and then quantifying glycans by fluorescence intensity). For example, 50 mole percent $NANA_2Gal_2GlcNAc_2Man_3GlcNAc_2$ means that 50 percent of the released glycans are $NANA_2Gal_2GlcNAc_2Man_3GlcNAc_2$ and the remaining 50 percent are comprised of other N-linked oligosaccharides.

The term "anti-inflammatory antibody" as used herein, refers to an antibody intended to be used to treat inflammation. The anti-inflammatory properties of an Fc-containing polypeptide can be measured using any method known in the art. In one embodiment, the anti-inflammatory properties of an Fc-containing polypeptide are measured using an animal model, such as the models described in Kaneko et al., *Science* 313:670-673 (2006), Anthony et al., *Science* 320:373-376 (2008), and Examples 20-21 herein. In another embodiment, the anti-inflammatory properties of an Fc-containing polypeptide are measured by determining the level of a biomarker related to inflammation (including without limitation: CRP, pro-inflammatory cytokines such as tumor necrosis factors (TNF-alpha), interferon-gamma, interleukin 6 (IL-6, IL-8, IL-10, chemokines, the coagulation marker D-dimer, sCD14, intestinal fatty acid binding peptide (IFABP), and hyaluronic acid. In one embodiment, the anti-inflammatory properties of an Fc-containing polypeptide is measured by determining the level of C-reactive protein (CRP) using a method known in the art. A decrease in the level of C-reactive protein indicates that the Fc-containing polypeptide has anti-inflammatory properties.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are listed below:

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Glycosylation of immunoglobulin G (IgG) in the Fc region, Asn297 (according to the EU numbering system), has been shown to be a requirement for optimal recognition and activation of effector pathways including antibody dependent cellular cytotoxicity (ADCC) and complement dependent cytotoxicity (CDC), Wright & Morrison, *Trends in Biotechnology*, 15: 26-31 (1997), Tao & Morrison, *J. Immunol.*, 143 (8):2595-2601 (1989). As such, glycosylation engineering in the constant region of IgG has become an area of active research for the development of therapeutic monoclonal antibodies (mAbs). It has been established that the presence of N-linked glycosylation at Asn297 is critical for mAb activity in immune effector function assays including ADCC, Rothman (1989), Lifely et al., *Glycobiology*, 5:813-822 (1995), Umana (1999), Shields (2002), and Shinkawa (2003), and complement dependent cytotoxicity (CDC), Hodoniczky et al., *Biotechnol. Prog.*, 21(6): 1644-1652 (2005), and Jefferis et al., *Chem. Immunol.*, 65: 111-128 (1997). This effect on function has been attributed to the specific conformation adopted by the glycosylated Fc domain, which appears to be lacking when glycosylation is absent. More specifically, IgG which lacks glycosylation in the Fc $C_H2$ domain does not bind to FcγR, including FcγRI, FcγRII, and FcγRIII, Rothman (1989).

Not only does the presence of glycosylation appear to play a role in the effector function of an antibody, the particular composition of the N-linked oligosaccharide is also important. For example, the presence of fucose shows a marked effect on in vitro FcγRIIIa binding and in vitro ADCC, Rothman (1989), and Li et al., *Nat. Biotechnol.* 24(2): 2100-215 (2006). Recombinant antibodies produced by mammalian cell culture, such as CHO or NS0, contain N-linked oligosaccharides that are predominantly fucosylated, Hossler et al., *Biotechnology and Bioengineering*, 95(5):946-960 (2006), Umana (1999), and Jefferis et al., *Biotechnol. Prog.* 21:11-16 (2005). Additionally, there is evidence that sialylation in the Fc region may impart anti-inflammatory properties to antibodies. Intravenous immunoglobulin (IVIG) purified over a lectin column to enrich for the sialylated form showed a distinct anti-inflammatory effect limited to the sialylated Fc fragment and was linked to an increase in expression of the inhibitory receptor FcγRIIb, Nimmerjahn and Ravetch., *J. Exp. Med.* 204:11-15 (2007).

Glycosylation in the Fc region of an antibody derived from mammalian cell lines typically consists of a heterogeneous mix of glycoforms, with the predominant forms typically being comprised of the complex fucosylated glycoforms: G0F, G1F, and, to a lesser extent, G2F. Possible conditions resulting in incomplete galactose transfer to the G0F structure include, but are not limited to, non-optimized galactose transfer machinery, such as β-1,4 galactosyl transferase, and poor UDP-galactose transport into the Golgi apparatus, suboptimal cell culture and protein expression conditions, and steric hindrance by amino acid residues neighboring the oligosaccharide. While each of these conditions may modulate the ultimate degree of terminal galactose, it is thought that subsequent sialic acid transfer to the Fc oligosaccharide is inhibited by the closed pocket configuration of the $C_H2$ domain. See, for example, FIG. 1, Jefferis, R., *Nature Biotech.*, 24 (10): 1230-1231, 2006. Without the correct terminal monosaccharide, specifically galactose, or with insufficient terminal galactosylated forms, there is little possibility of producing a sialylated form, capable of acting as a therapeutic protein, even when produced in the presence of sialyl transferase. Protein engineering and structural analysis of human IgG-Fc glycoforms has shown that glycosylation profiles are affected by Fc conformation, such as the finding that increased levels of galactose and sialic acid on oligosaccharides derived from CHO-produced IgG3 could be achieved when specific amino acids from the Fc pocket were mutated, to an alanine including F241, F243, V264, D265 and R301. Lund et al., *J. Immunol.* 157(11); 4963-4969 (1996). It was further shown that certain mutations had some effect on cell mediated superoxide generation and complement mediated red cell lysis, which are used as surrogate markers for FcγRI and C1q binding, respectively.

Figure 4:
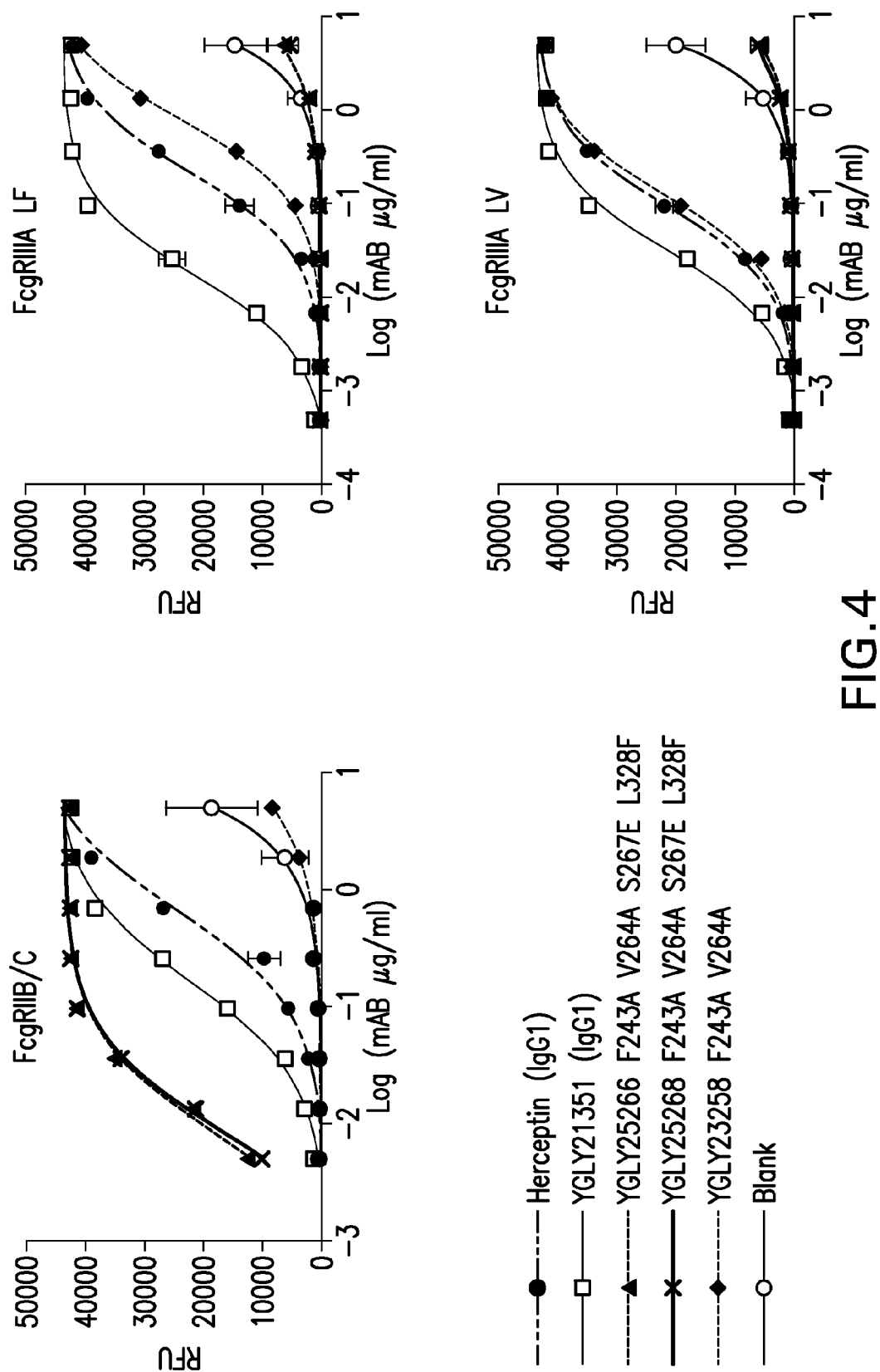

It has been reported that yeast have been genetically engineered to produce host strains capable of secreting glycoproteins with highly uniform glycosylation. Choi et al., *PNAS, USA* 100(9): 5022-5027 (2003) describes the use of libraries of α1,2 mannosidase catalytic domains and N-acetylglucosaminyltransferase I catalytic domains in combination with a library of fungal type II membrane protein leader sequences to localize the catalytic domains to the secretory pathway. In this way, strains were isolated that produced in vivo glycoproteins with uniform $Man_5GlcNAc_2$ or $GlcNAcMan_5GlcNAc_2$ N-glycan structures. Hamilton et al., *Science* 313 (5792): 1441-1443 (2006) described the production of a glycoprotein, erythropoietin, produced in *Pichia pastoris*, as having a glycan composition that consisted predominantly of a bisialylated glycan structure, GS6.0, $NANA_2Gal_2GlcNAc_2Man_3GlcNAc_2$ (90.5%) and monosialylated, GS5.5, $NANAGal_2GlcNAc_2Man_3GlcNAc_2$ (7.9%). However, an antibody produced in a similar strain will have a markedly lower content of sialylated N-glycan due to the relatively low level of terminal galactose substrate in the antibody as seen in FIG. 4. It has also recently been shown that sialylation of a Fc oligosaccharide imparts anti-inflammatory properties on therapeutic intravenous gamma globulin and its Fc fragments, Kaneko et al., *Science* 313(5787): 670-673 (2006), and that the anti-inflammatory activity is dependent on the α2,6-linked form, but not the α2,3 form, of sialic acid, Anthony et al., *Science*, 320: 373-376 (2008).

Host Organisms and Cell Lines

The Fc-containing polypeptides of this invention can be made in any host organism or cell line. In one embodiment, an Fc-containing polypeptide of the invention is made in a host cell which is capable of producing sialylated N-glycans.

In one embodiment, an Fc-containing polypeptide of the invention is made in a mammalian cell where the cell either endogenously or through genetic or process manipulation produces glycoproteins containing either a mixture of terminal α2-6 and α2-3 sialic acid, or only terminal α2-6 sialic acid. The propagation of mammalian cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); Chinese hamster ovary cells/–DHFR(CHO); mouse sertoli cells (TM4); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells; MRC 5 cells; FS4 cells; hybridoma cell lines; NS0; SP2/0; and a human hepatoma line (Hep G2).

In one embodiment, an Fc-containing polypeptide of the invention can be made in a plant cell which is engineered to produce sialylated N-glycans. See, e.g., Cox et al., *Nature Biotechnology* (2006) 24, 1591-1597 (2006) and Castilho et al., *J. Biol. Chem.* 285(21): 15923-15930 (2010).

In one embodiment, an Fc-containing polypeptide of the invention can be made in an insect cell which is engineered to produce sialylated N-glycans. See, e.g., Harrison and Jarvis, *Adv. Virus Res.* 68:159-91 (2006).

In one embodiment, an Fc-containing polypeptide of the invention can be made in a bacterial cell which is engineered to produce sialylated N-glycans. See, e.g., Lizak et al., *Bioconjugate Chem.* 22:488-496 (2011).

In one embodiment, an Fc-containing polypeptide of the invention can be made in a lower eukaryotic host cell or organism. Recent developments allow the production of fully humanized therapeutics in lower eukaryotic host organisms, yeast and filamentous fungi, such as *Pichia pastoris*, Gerngross et al., U.S. Pat. No. 7,029,872 and U.S. Pat. No. 7,449,308, the disclosures of which are hereby incorporated by reference. See also Jacobs et al., *Nature Protocols* 4(1):58-70 (2009).

Due to the decreased FcγR and C1q binding, the materials and methods described herein can be used to produce recombinant glycosylated antibodies with decreased effector function when compared to a parent antibody. Antibodies so produced in *Pichia pastoris* by the methods of the invention were produced at high yield, with decreased effector function, and had a predominant species of glycoprotein having a terminal α2,6-linked sialic acid residue as compared to antibodies produced in glycoengineered *Pichia pastoris* cells lacking the specific Fc mutations or in *Pichia pastoris* host cells retaining their endogenous glycosylation machinery.

In one embodiment, an Fc-containing polypeptide of the invention is made in a host cell, more preferably a yeast or filamentous fungal host cell, that has been engineered to produce glycoproteins having a predominant N-glycan comprising a terminal sialic acid. In one embodiment of the invention, the predominant N-glycan is the α2,6 linked form of $SA_2Gal_2GlcNAc_2Man_3GlcNAc_2$, produced in strains glycoengineered with α2,6 sialyl transferase which do not produce any α2,3 linked sialic acid. In other embodiments, the strain will be engineered to express an α2,3 sialyl transferase alone or in combination with an α2,6, sialyl transferase, resulting in α2,3 linked or a combination of α2,6 and α2,3 linked sialic acid as the predominant N-glycans.

The cell lines to be used to make the Fc-containing polypeptides of the invention can be any cell line, in particular cell lines with the capability of producing one or more sialylated glycoproteins. Those of ordinary skill in the art would recognize and appreciate that the materials and methods described herein are not limited to the specific strain of *Pichia pastoris* provided as an example herein, but could include any *Pichia pastoris* strain or other yeast or filamentous fungal strains in which N-glycans with one or more terminal galactose, such as $Gal_2GlcNAc_2Man_3$, are produced. The terminal galactose acts as a substrate for the production of α2,6-linked sialic acid, resulting in the N-glycan structure $NANA_2Gal_2GlcNAc_2Man_3GlcNAc_2$. Examples of suitable strains are described in U.S. Pat. No. 7,029,872, US 2006-0286637 and Hamilton et al., *Science* 313 (5792): 1441-1443 (2006), the descriptions of which are incorporated herein as if set forth at length.

In general, lower eukaryotes such as yeast are used for expression of the proteins, particularly glycoproteins because they can be economically cultured, give high yields, and when appropriately modified are capable of suitable glycosylation. Yeast particularly offers established genetics allowing for rapid transformations, tested protein localization strategies and facile gene knock-out techniques. Suitable vectors have expression control sequences, such as promoters, including 3-phosphoglycerate kinase or other glycolytic enzymes, and an origin of replication, termination sequences and the like as desired.

While the invention has been demonstrated herein using the methylotrophic yeast *Pichia pastoris*, other useful lower eukaryote host cells include *Pichia pastoris*, *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporiumi lucknowense*, *Fusarium* sp., *Fusarium gramineum*, *Fusarium venenatum* and *Neurospora crassa*. Various yeasts, such as *K. lactis*, *Pichia pastoris*, *Pichia methanolica*, and *Hansenula polymorpha* are particularly suitable for cell culture because they are able to grow to high cell densities and secrete large quantities of recombinant protein. Likewise, filamentous fungi, such as *Aspergillus niger*, *Fusarium* sp, *Neurospora crassa* and others can be used to produce glycoproteins of the invention at an industrial scale.

Lower eukaryotes, particularly yeast and filamentous fungi, can be genetically modified so that they express glycoproteins in which the glycosylation pattern is human-like or humanized. As indicated above, the term "human-like N-glycan", as used herein refers, to the N-linked oligosaccharides which closely resemble the oligosaccharides produced by non-engineered, wild-type human cells. In preferred embodiments of the present invention, the host cells of the present invention are capable of producing human-like glycoproteins with hybrid and/or complex N-glycans; i.e., "human-like N-glycosylation." The specific "human-like" glycans predominantly present on glycoproteins produced from the host cells of the invention will depend upon the specific engineering steps that are performed. In this manner, glycoprotein compositions can be produced in which a specific desired glycoform is predominant in the composition. Such can be achieved by eliminating selected endogenous glycosylation enzymes and/or genetically engineering the host cells and/or supplying exogenous enzymes to mimic all or part of the mammalian glycosylation pathway as described in U.S. Pat. No. 7,449,308. If desired, additional genetic engineering of the glycosylation can be performed, such that the glycoprotein can be produced with or without core fucosylation. Use of lower eukaryotic host cells is further advantageous in that these cells are able to produce highly homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition.

Lower eukaryotes, particularly yeast, can be genetically modified so that they express glycoproteins in which the glycosylation pattern is human-like or humanized. Such can be achieved by eliminating selected endogenous glycosylation enzymes and/or supplying exogenous enzymes as described by Gerngross et al., U.S. Pat. No. 7,449,308. For example, a host cell can be selected or engineered to be depleted in α1,6-mannosyl transferase activities, which would otherwise add mannose residues onto the N-glycan on a glycoprotein.

In one embodiment, the host cell further includes an α1,2-mannosidase catalytic domain fused to a cellular targeting signal peptide not normally associated with the catalytic domain and selected to target the α1,2-mannosidase activity to the ER or Golgi apparatus of the host cell. Passage of a recombinant glycoprotein through the ER or Golgi apparatus of the host cell produces a recombinant glycoprotein comprising a $Man_5GlcNAc_2$ glycoform, for example, a recombinant glycoprotein composition comprising predominantly a $Man_5GlcNAc_2$ glycoform. For example, U.S. Pat. Nos. 7,029,872 and 7,449,308 and U.S. Published Patent Application No. 2005/0170452 disclose lower eukaryote host cells capable of producing a glycoprotein comprising a $Man_5GlcNAc_2$ glycoform.

In a further embodiment, the immediately preceding host cell further includes a GlcNAc transferase I (GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a $GlcNAcMan_5GlcNAc_2$ glycoform, for example a recombinant glycoprotein composition comprising predominantly a $GlcNAcMan_5GlcNAc_2$ glycoform. U.S. Pat. Nos. 7,029,872 and 7,449,308 and U.S. Published Patent Application No. 2005/0170452 disclose lower eukaryote host cells capable of producing a glycoprotein comprising a $GlcNAcMan_5GlcNAc_2$ glycoform. The glycoprotein produced in the above cells can be treated in vitro with a hexosaminidase to produce a recombinant glycoprotein comprising a $Man_5GlcNAc_2$ glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant glycoprotein through the ER or Golgi apparatus of the host cell produces a recombinant glycoprotein comprising a $GlcNAcMan_3GlcNAc_2$ glycoform, for example a recombinant glycoprotein composition comprising predominantly a $GlcNAcMan_3GlcNAc_2$ glycoform. U.S. Pat. No. 7,029,872 and U.S. Published Patent Application No. 2004/0230042 discloses lower eukaryote host cells that express mannosidase II enzymes and are capable of producing glycoproteins having predominantly a $GlcNAcMan_3GlcNAc_2$ glycoform. The glycoprotein produced in the above cells can be treated in vitro with a hexosaminidase to produce a recombinant glycoprotein comprising a $Man_3GlcNAc_2$ glycoform.

In a further embodiment, the immediately preceding host cell further includes GlcNAc transferase II (GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform. U.S. Pat. Nos. 7,029,872 and 7,449,308 and U.S. Published Patent Application No. 2005/0170452 disclose lower eukaryote host cells capable of producing a glycoprotein comprising a $GlcNAc_2Man_3GlcNAc_2$ glycoform. The glycoprotein produced in the above cells can be treated in vitro with a hexosaminidase to produce a recombinant glycoprotein comprising a $Man_3GlcNAc_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a $GalGlcNAc_2Man_3GlcNAc_2$ or $Gal_2GlcNAc_2Man_3GlcNAc_2$ glycoform, or mixture thereof for example a recombinant glycoprotein composition comprising predominantly a $GalGlcNAc_2Man_3GlcNAc_2$ glycoform or $Gal_2GlcNAc_2Man_3GlcNAc_2$ glycoform or mixture thereof. U.S. Pat. No. 7,029,872 and U.S. Published Patent Application No. 2006/0040353 discloses lower eukaryote host cells capable of producing a glycoprotein comprising a $Gal_2GlcNAc_2Man_3GlcNAc_2$ glycoform. The glycoprotein produced in the above cells can be treated in vitro with a galactosidase to produce a recombinant glycoprotein comprising a $GlcNAc_2Man_3GlcNAc_2$ glycoform, for example a recombinant glycoprotein composition comprising predominantly a $GlcNAc_2Man_3GlcNAc_2$ glycoform.

In a further embodiment, the immediately preceding host cell further includes a sialyltransferase catalytic domain fused to a cellular targeting signal peptide not normally associated with the catalytic domain and selected to target sialyltransferase activity to the ER or Golgi apparatus of the host cell. In a preferred embodiment, the sialyltransferase is an alpha2,6-sialyltransferase. Passage of the recombinant glycoprotein through the ER or Golgi apparatus of the host cell produces a recombinant glycoprotein comprising predominantly a $NANA_2Gal_2GlcNAc_2Man_3GlcNAc_2$ glycoform or $NANAGal_2GlcNAc_2Man_3GlcNAc_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729 discloses a method for genetically engineering lower eukaryotes to have a CMP-sialic acid synthesis pathway and U.S. Published Patent Application No. 2006/0286637 discloses a method for genetically engineering lower eukaryotes to produce sialylated glycoproteins. To enhance the amount of sialylation, it can be advantageous to construct the host cell to include two or more copies of the CMP-sialic acid synthesis pathway or two or more copies of the sialylatransferase. The glycoprotein produced in the above cells can be treated in vitro with a neuraminidase to produce a recombinant glycoprotein comprising predominantly a $Gal_2GlcNAc_2Man_3GlcNAc_2$ glycoform or $GalGlcNAc_2Man_3GlcNAc_2$ glycoform or mixture thereof.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX) N-glycan structures such as disclosed in U.S. Published Patent Application Nos. 2005/0208617 and 2007/0037248. Further, the proceeding host cells can produce recombinant glycoproteins (for example, antibodies) comprising SA(1-4)Gal(1-4)GlcNAc(2-4) $Man_3GlcNAc_2$, including antibodies comprising NANA(1-4)Gal(1-4)GlcNAc(2-4) $Man_3GlcNAc_2$, NGNA(1-4)Gal(1-4)GlcNAc(2-4)$Man_3GlcNAc_2$ or a combination of NANA(1-4)Gal(1-4)GlcNAc(2-4)$Man_3GlcNAc_2$ and NGNA(1-4)Gal(1-4)GlcNAc(2-4) $Man_3GlcNAc_2$. In one embodiment, the recombinant glycoprotein will comprise N-glycans comprising a structure selected from the group consisting of SA(1-4)Gal(1-4)GlcNAc(2-4)$Man_3$ $GlcNAc_2$ and devoid of any α2-3 linked SA.

In further embodiments, the host cell that produces glycoproteins that have predominantly $GlcNAcMan_5GlcNAc_2$ N-glycans further includes a galactosyltransferase catalytic domain fused to a cellular targeting signal peptide not normally associated with the catalytic domain and selected to target the galactosyltransferase activity to the ER or Golgi apparatus of the host cell. Passage of the recombinant glycoprotein through the ER or Golgi apparatus of the host cell produces a recombinant glycoprotein comprising predominantly the $GalGlcNAcMan_5GlcNAc_2$ glycoform.

In a further embodiment, the immediately preceding host cell that produced glycoproteins that have predominantly the $GalGlcNAcMan_5GlcNAc_2$ N-glycans further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising a $SAGalGlcNAcMan_5GlcNAc_2$ glycoform (for example $NANAGalGlcNAcMan_5GlcNAc_2$ or $NGNAGalGlcNAcMan_5GlcNAc_2$ or a mixture thereof).

Any of the preceding host cells can further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Further, any of the preceding host cells can be further manipulated to increase N-glycan occupancy. See e, g., Gaulitzek et al., *Biotechnol. Bioengin.* 103:1164-1175 (2009); Jones et al., *Biochim. Biospyhs. Acta* 1726:121-137 (2005); WO2006/107990. In one embodiment, any of the preceding host cells can be further engineered to comprise at least one nucleic acid molecule encoding a heterologous single-subunit oligosaccharyltransferase (for example, *Leishmania* sp. STT3A protein, STT3B protein, STT3C protein, STT3D protein or combinations thereof) and a nucleic acid molecule encoding the heterologous glycoprotein, and wherein the host cell expresses the endogenous host cell genes encoding the proteins comprising the endogenous OTase complex. In one embodiment, any of the preceding host cells can be further engineered to comprise at least one nucleic acid molecule encoding a *Leishmania* sp. STT3D protein and a nucleic acid molecule encoding the heterologous glycoprotein, and wherein the host cell expresses the endogenous host cell genes encoding the proteins comprising the endogenous OTase complex.

Host cells further include lower eukaryote cells (e.g., yeast such as *Pichia pastoris*) that are genetically engineered to produce glycoproteins that do not have α-mannosidase-resistant N-glycans. This can be achieved by deleting or disrupting one or more of the β-mannosyltransferase genes (e.g., BMT1, BMT2, BMT3, and BMT4) (See, U.S. Published Patent Application No. 2006/0211085) and glycoproteins having phosphomannose residues by deleting or disrupting one or both of the phosphomannosyl transferase genes PNO1 and MNN4B (See for example, U.S. Pat. Nos. 7,198,921 and 7,259,007), which in further aspects can also include deleting or disrupting the MNN4A gene. Disruption includes disrupting the open reading frame encoding the particular enzymes or disrupting expression of the open reading frame or abrogating translation of RNAs encoding one or more of the β-mannosyltransferases and/or phosphomannosyltransferases using interfering RNA, antisense RNA, or the like. Further, cells can produce glycoproteins with α-mannosidase-resistant N-glycans through the addition of chemical hinhibios or through modification of the cell culture condition. These host cells can be further modified as described above to produce particular N-glycan structures.

Host cells further include lower eukaryote cells (e.g., yeast such as *Pichia pastoris*) that are genetically modified to control O-glycosylation of the glycoprotein by deleting or disrupting one or more of the protein O-mannosyltransferase (Dol-P-Man:Protein (Ser/Thr) Mannosyl Transferase genes) (PMTs) (See U.S. Pat. No. 5,714,377) or grown in the presence of Pmtp inhibitors and/or an α-mannosidase as disclosed in Published International Application No. WO 2007/061631, or both. Disruption includes disrupting the open reading frame encoding the Pmtp or disrupting expression of the open reading frame or abrogating translation of RNAs encoding one or more of the Pmtps using interfering RNA, antisense RNA, or the like. The host cells can further include any one of the aforementioned host cells modified to produce particular N-glycan structures.

Pmtp inhibitors include but are not limited to a benzylidene thiazolidinediones. Examples of benzylidene thiazolidinediones that can be used are 5-[[3,4-bis(phenylmethoxy)phenyl]methylene]-4-oxo-2-thioxo-3-thiazolidineacetic Acid; 5-[[3-

(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo-3-thiazolidineacetic acid.

In particular embodiments, the function or expression of at least one endogenous PMT gene is reduced, disrupted, or deleted. For example, in particular embodiments the function or expression of at least one endogenous PMT gene selected from the group consisting of the PMT1, PMT2, PMT3, and PMT4 genes is reduced, disrupted, or deleted; or the host cells are cultivated in the presence of one or more PMT inhibitors. In further embodiments, the host cells include one or more PMT gene deletions or disruptions and the host cells are cultivated in the presence of one or more Pmtp inhibitors. In particular aspects of these embodiments, the host cells also express a secreted α-1,2-mannosidase.

PMT deletions or disruptions and/or Pmtp inhibitors control O-glycosylation by reducing O-glycosylation occupancy, that is, by reducing the total number of O-glycosylation sites on the glycoprotein that are glycosylated. The further addition of an α-1,2-mannosidase that is secreted by the cell controls O-glycosylation by reducing the mannose chain length of the O-glycans that are on the glycoprotein. Thus, combining PMT deletions or disruptions and/or Pmtp inhibitors with expression of a secreted α-1,2-mannosidase controls O-glycosylation by reducing occupancy and chain length. In particular circumstances, the particular combination of PMT deletions or disruptions, Pmtp inhibitors, and α-1,2-mannosidase is determined empirically as particular heterologous glycoproteins (Fabs and antibodies, for example) may be expressed and transported through the Golgi apparatus with different degrees of efficiency and thus may require a particular combination of PMT deletions or disruptions, Pmtp inhibitors, and α-1,2-mannosidase. In another aspect, genes encoding one or more endogenous mannosyltransferase enzymes are deleted. This deletion(s) can be in combination with providing the secreted α-1,2-mannosidase and/or PMT inhibitors or can be in lieu of providing the secreted α-1,2-mannosidase and/or PMT inhibitors.

Thus, the control of O-glycosylation can be useful for producing particular glycoproteins in the host cells disclosed herein in better total yield or in yield of properly assembled glycoprotein. The reduction or elimination of O-glycosylation appears to have a beneficial effect on the assembly and transport of whole antibodies and Fab fragments as they traverse the secretory pathway and are transported to the cell surface. Thus, in cells in which O-glycosylation is controlled, the yield of properly assembled antibodies or Fab fragments is increased over the yield obtained in host cells in which O-glycosylation is not controlled.

To reduce or eliminate the likelihood of N-glycans and O-glycans with β-linked mannose residues, which are resistant to α-mannosidases, the recombinant glycoengineered *Pichia pastoris* host cells are genetically engineered to eliminate glycoproteins having α-mannosidase-resistant N-glycans by deleting or disrupting one or more of the β-mannosyltransferase genes (e.g., BMT1, BMT2, BMT3, and BMT4) (See, U.S. Pat. No. 7,465,577 and U.S. Pat. No. 7,713,719). The deletion or disruption of BMT2 and one or more of BMT1, BMT3, and BMT4 also reduces or eliminates detectable cross reactivity to antibodies against host cell protein.

Yield of glycoprotein can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell also appears to control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in Published International Application No. WO 2009105357 and WO2010019487 (the disclosures of which are incorporated herein by reference). Like above, further included are lower eukaryotic host cells wherein, in addition to replacing the genes encoding one or more of the endogenous chaperone proteins with nucleic acid molecules encoding one or more mammalian or human chaperone proteins or overexpressing one or more mammalian or human chaperone proteins as described above, the function or expression of at least one endogenous gene encoding a protein O-mannosyltransferase (PMT) protein is reduced, disrupted, or deleted. In particular embodiments, the function of at least one endogenous PMT gene selected from the group consisting of the PMT1, PMT2, PMT3, and PMT4 genes is reduced, disrupted, or deleted.

In addition, O-glycosylation may have an effect on an antibody or Fab fragment's affinity and/or avidity for an antigen. This can be particularly significant when the ultimate host cell for production of the antibody or Fab is not the same as the host cell that was used for selecting the antibody. For example, O-glycosylation might interfere with an antibody's or Fab fragment's affinity for an antigen, thus an antibody or Fab fragment that might otherwise have high affinity for an antigen might not be identified because O-glycosylation may interfere with the ability of the antibody or Fab fragment to bind the antigen. In other cases, an antibody or Fab fragment that has high avidity for an antigen might not be identified because O-glycosylation interferes with the antibody's or Fab fragment's avidity for the antigen. In the preceding two cases, an antibody or Fab fragment that might be particularly effective when produced in a mammalian cell line might not be identified because the host cells for identifying and selecting the antibody or Fab fragment was of another cell type, for example, a yeast or fungal cell (e.g., a *Pichia pastoris* host cell). It is well known that O-glycosylation in yeast can be significantly different from O-glycosylation in mammalian cells. This is particularly relevant when comparing wild type yeast O-glycosylation with mucin-type or dystroglycan type O-glycosylation in mammals. In particular cases, O-glycosylation might enhance the antibody or Fab fragments affinity or avidity for an antigen instead of interfere with antigen binding. This effect is undesirable when the production host cell is to be different from the host cell used to identify and select the antibody or Fab fragment (for example, identification and selection is done in yeast and the production host is a mammalian cell) because in the production host the O-glycosylation will no longer be of the type that caused the enhanced affinity or avidity for the antigen. Therefore, controlling O-glycosylation can enable use of the materials and methods herein to identify and select antibodies or Fab fragments with specificity for a particular antigen based upon affinity or avidity of the antibody or Fab fragment for the antigen without identification and selection of the antibody or Fab fragment being influenced by the O-glycosylation system of the host cell. Thus, controlling O-glycosylation further enhances the usefulness of yeast or fungal host cells to identify and select antibodies or Fab fragments that will ultimately be produced in a mammalian cell line.

Those of ordinary skill in the art would further appreciate and understand how to utilize the methods and materials described herein in combination with other *Pichia pastoris* and yeast cell lines that have been genetically engineered to produce specific N-glycans or sialylated glycoproteins, such as, but, not limited to, the host organisms and cell lines described above that have been genetically engineered to produce specific galactosylated or sialylated forms. See, for example, US 2006-0286637, Production of Sialylated N-Glycans in Lower Eukaryotes, in which the pathway for galactose uptake and utilization as a carbon source has been genetically modified, the description of which is incorporated herein as if set forth at length.

Additionally, the methods herein can be used to produce the above described recombinant Fc-containing polypeptides in other lower eukaryotic cell lines which have been engineered to produce human-like and human glycoproteins that do not have α2,6 sialyltransferase activity. The methods can also be used to produce the above described recombinant Fc-containing polypeptides in eukaryotic cell lines in which production of sialylated N-glycans is an innate feature.

Levels of α2,3- and α2,6-linked sialic acid on the Fc-containing polypeptides can be measured using well known techniques including nuclear magnetic resonance (NMR), normal phase high performance liquid chromatography (HPLC), and high performance anion exchange chromatography with pulsed amperometric detection (HPAEC-PAD).

Biological Properties of Fc Muteins

For many Fc-containing polypeptides the lack of or significant decrease in effector function, as shown by decreased FcγR and C1q binding, Idusogie et al., *J. Immunology,* 164 (8): 4178-84 (2000) and Shields et al., *J. Biol. Chem.,* 276: 6591-6604 (2001), and increased anti-inflammatory properties would be desirable characteristics.

Applicants have developed a quadruple Fc mutein, F243A/V264A/S267E/L328F, which will produce Fc-containing polypeptides having the aforesaid desired characteristics. The Examples herein comprise transforming a host cell with a polynucleotide vector encoding a Fc-containing polypeptide comprising mutations at positions 243, 264, 267 and 328 of the Fc region, and culturing the transformed host cell to produce the Fc-containing polypeptide.

Production of Fc-Containing Polypeptides

The Fc-containing polypeptides of the invention can be made according to any method known in the art suitable for generating polypeptides comprising an Fc region. In one embodiment, the Fc-containing polypeptide is an antibody or an antibody fragment (including, without limitation a polypeptide comprising, consisting, or consisting essentially of the Fc region of an antibody). In another embodiment, the Fc-containing polypeptide is an immunoadhesin. Methods of preparing antibody and antibody fragments are well known in the art. Methods of introducing point mutations into a polypeptide, for example site directed mutagenesis, are also well known in the art.

In the Examples disclosed herein, an IgG1 heavy and light chain containing a consensus $C_H2$ sequence and the Fc double mutants described herein were expressed in two different glycoengineered *Pichia pastoris* strains. As described in the Examples that follow, the heavy and light chain gene sequences were under the control of a methanol inducible promoter, AOX1, and incorporated a bleomycin (Zeocin) selection marker. This strategy integrates the entire expression cassette into the Trp2 locus by homologous DNA recombination.

Figure 2:
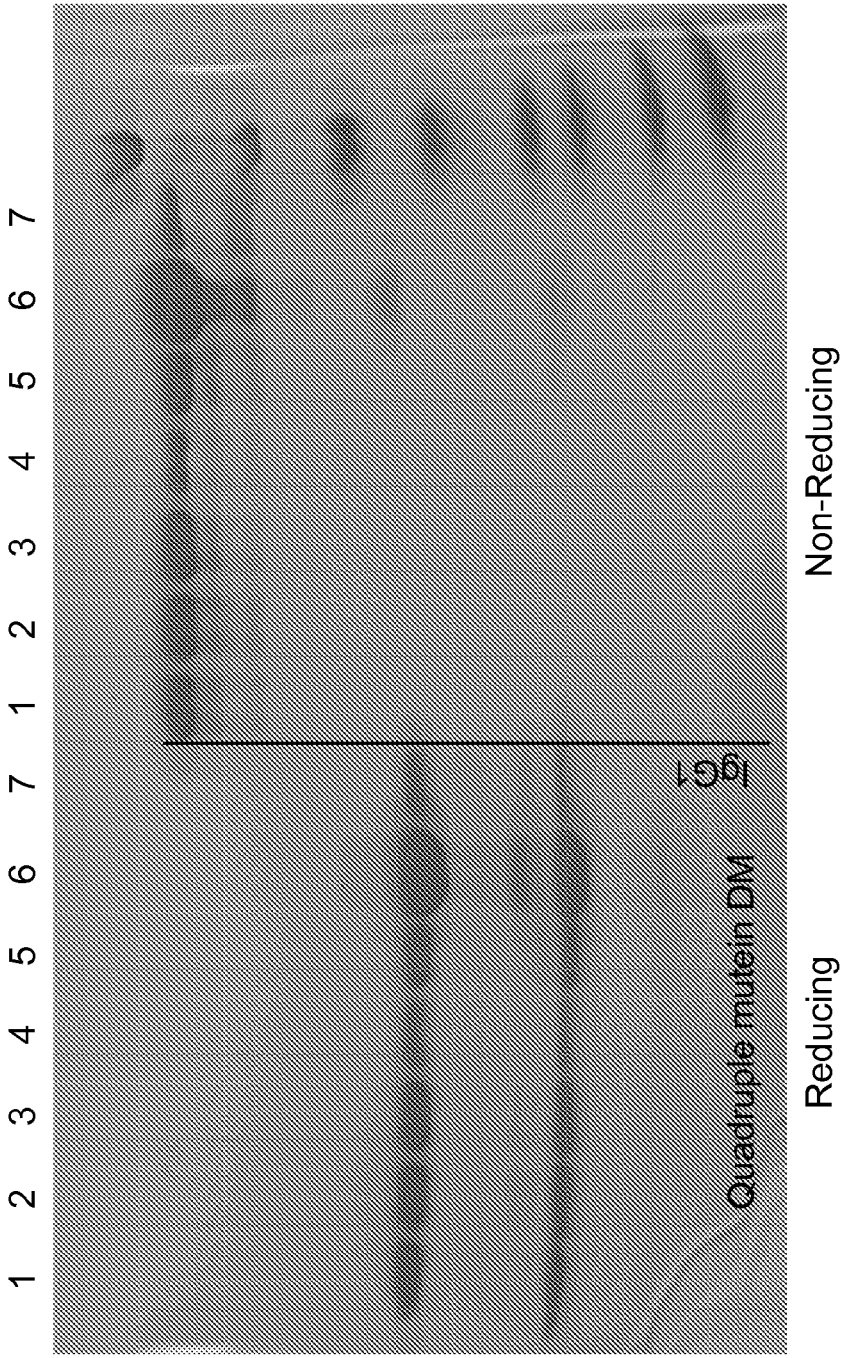
FIG. 2 is a representation of the gels from an SDS-PAGE analysis characterizing the nonreduced (NR) and reduced (R) antibodies produced by the materials and methods herein. Lane 1 contains antibodies produced in stratin YGLY25265. Lane 2 contains antibodies produced in strain YGLY25266. Lane 3 contains antibodies produced in strain YGLY25267. Lane 4 contains antibodies produced in strain YGLY25268. Lane 5 contains antibodies produced in strain YGLY25269. Lane 6 contains antibodies produced in strain YGLY23258. Lane 7 contains antibodies produced in strain GLY21351.

Secreted antibodies were captured from the fermentation broth by protein A affinity chromatography followed by a Source 30S cation exchange purification step. Purified antibodies were characterized by SDS-PAGE (FIG. 2) to assess proper assembly. As seen in FIG. 2, the antibodies produced by the materials and methods herein were properly assembled.

Antigen affinity for the various antibodies made by the materials and methods herein was determined by a cell based assay using a Biacore. As expected, all of the antibodies, including the Fc muteins, bound equally well to the PCSK9 antigen.

N-Glycan Analysis of Fc Muteins

For many glycoproteins, including certain antibodies, sialylation of the terminal N-linked glycan of an IgG Fc region is essential for producing glycoproteins and antibodies that have the correct conformation to impart therapeutic activity. See, for example, Anthony et al., *Science,* 320: 373-376 (2008), where terminal sialylation was correlated to anti-inflammatory activity for an IVIG preparation. Sialylation requires the presence of a penultimate galactose, upon which the sialyl transferase acts to form the sialylated glycan. Thus, glycoproteins lacking one or more terminal galactose glycoforms cannot produce antibodies having the α2,6-linked sialic acid composition associated with anti-inflammatory activity.

Mammalian cells have full capability of sialylation on its glycoproteins, however, due to spatial constricts antibodies produced in mammalian cell culture, such as CHO cells, have even incomplete galactose transfer to its N297 linked glycans. Moreover, because of further spatial hindrance, the level of sialylation of antibody from mammalian cell such as CHO usually contains little or no sialic acid at its N297 linked glycans. In the case of CHO cell production, when sialic acid is added, it is linked by an α2,3-linkage. CHO cells do not express an α2,6 sialyl transferase necessary to produce the α2,6-linked form of sialic acid, which has been associated with anti-inflammatory activity (Lee et al, *J. Biol. Chem.* 264: 13848-13855 (1989). Overexpression of a specific α2,6 sialyltranferase in CHO can give rise to a mixture of α2,3-linked and α2,6-linked sialic acid (Bragonzi et al., *BBA* 1474:273-282 (2000); *Biochem. Biophys. Res. Comm.* 289: 243-249 (2001)).

Glycoengineered *Pichia pastoris* GFI5.0 strains, which are capable of producing high levels of galactosylated non-antibody proteins, such as erythropoietin (Hamilton et al., *Science,* 313: 1441-1443 (2006)), produce antibodies with relatively low amounts of a terminal galactose that can be acted upon to form the α2,6-linked sialylated form. Antibodies produced in such *Pichia pastoris* strains typically have a composition including glycoforms G0 (60%), G1 (17%), G2 (4%) and Man5 (8%). Even antibodies produced in *Pichia pastoris* GFI6.0 strains, which have a glycan composition comprising G0 (43.5%), G1 (20.8%), G2 (2.7%), NANAGalGlcNAcMan$_5$GlcNAc$_2$ (5.5%), and NANAGal$_2$GlcNAc$_2$Man$_3$GlcNAc$_2$ (4.9%), have relatively low levels of the α2,6-linked sialylated form. Thus, antibodies produced in GFI 5.0 and 6.0 strains have much lower levels of galactosylation and sialylation compared to non-antibody proteins (such as erythropoietin) produced in the same strains.

Glycoforms of the *Pichia pastoris* wild-type PCSK-9 antibody (1F11) from the GFI5.0 strain (YGLY21351) included M4, G0, G1, M6, G2 glycans. Glycoforms of the *Pichia pastoris* double mutein PCSK-9 antibody (1F11 F243A/V264A) from the GFI 6.0 strain (YGLY23258) included G0, M5, G1, G2, A1 and A2 glycans. Glycoforms of the *Pichia pastoris* 1F11 F243A/V264A/S267E/L328F) from the GFI 6.0 strain included: A1, A1H and A2 (YGLY25267) and G2, Man5, A1 and A2 (YGLY25269).

FcγR Binding of Fc Muteins

Using an ELISA based assay, Applicants compared Fc gamma receptor (FcγR) binding for the commercially available Herceptin, a wildtype anti-PCSK9 antibody (1F11), an double mutein anti-PCSK9 (1F11) antibody having the F243A/V243A mutations, and a quadruple mutein anti-PCSK9 (1F11) antibody having the F243A/V264A/S267E/L328F mutations. As shown in the Examples, the Fc quadruple mutein has decreased affinity to FcγRI, FcγRIIa and FcγRIIa, and increased affinity to FcγRIIb, as compared to an antibody having a native Fc region or as compared to an antibody having a F243A/V264A double mutation.

Neither the double nor the quadruple mutein bind FcγRIIa.

Neither the double nor the quadruple mutein bind FcγRIIIa-F158 or FcγRIIIa-V158.

However, the quadruple mutein has increased binding to FcγRIIb which is surprising since the double mutein shown only minimal binding to this receptor.

Taken together, these data suggest that the quadruple Fc mutein is less prone to activating and recruiting immune cells such as macrophages, monocytes and natural killer cells as compared to double mutein or non-mutein (native) versions of the antibody.

Biological Targets

It should be noted that while, in the examples that follow, Applicants exemplify the materials and methods of the invention using an anti-PCSK9 antibody, the invention is not limited to the disclosed antibodies. Those of ordinary skill in the art would recognize and appreciate that the materials and methods herein could be used to produce any Fc-containing polypeptide for which the characteristics of enhanced anti-inflammatory activity or decreased effector function would be desirable. It should further be noted that there is no restriction as to the type of Fc-containing polypeptide or antibody so produced by the invention. The Fc region of the Fc-containing polypeptide could be from an IgA, IgD, IgE, IgG or IgM. In one embodiment, the Fc region of the Fc-containing polypeptide is from an IgG, including IgG1, IgG2, IgG3 or IgG4. In one embodiment, Fc region of the Fc-containing polypeptide is from an IgG1. In specific embodiments the antibodies or antibody fragments produced by the materials and methods herein can be humanized, chimeric or human antibodies.

In some embodiments, the Fc-containing polypeptides of the invention will bind to a biological target that is involved in inflammation.

In some embodiments, the Fc-containing polypeptide of the invention will bind to a pro-inflammatory cytokine. In some embodiments, the Fc-containing polypeptide of the invention will bind to a molecule selected from the group consisting of: APRIL, INF-α, BAFF (BLys), CD22, TNF-α, IL-1, IL-2, IL-4, IL-5, IL-6, IL-8, IL-9, IL-10, IL-12, IL-15, IL-17, IL-18, IL-20, IL-21, IL-22, IL-23, IL-23R, IL-25, IL-27, IL-33, CD2, CD4, CD11A, CD14, CD18, CD19, CD23, CD25, CD38, CD40, CD40L, CD20, CD52, CD64, CD80, CD147, CD200, CD200R, TSLP, TSLPR, PD-1, PDL1, CTLA4, VLA-4, VEGF, PCSK9, α4β7-integrin, E-selectin, Fact II, ICAM-3, beta2-integrin, IFNγ, C5, CBL, LCAT, CR3, MDL-1, GITR, ADDL, CGRP, TRKA, IGF1R, RANKL, GTC, αBLys, or the receptor for any of the above mentioned molecules. In one embodiment, the Fc-containing polypeptide of the invention will bind to TNF-α. In another embodiment, the Fc-containing polypeptide of the invention will bind to Her2. In another embodiment, the Fc-containing polypeptide of the invention will bind to PCSK9. In another embodiment, the Fc-containing polypeptide of the invention will bind to TNFR. In another embodiment, the Fc-containing polypeptide of the invention will bind to LCAT. In another embodiment, the Fc-containing polypeptide of the invention will bind to TSLP. In another embodiment, the Fc-containing polypeptide of the invention will bind to PD-1. In another embodiment, the Fc-containing polypeptide of the invention will bind to IL-23.

In some embodiments, the Fc-containing polypeptides of the invention will be specific for an antigen selected from autoimmune antigens, allergens, MHC molecules or Rhesus factor D antigen. See, e.g., the antigens listed in Table 1 of WO2010/10910, which is incorporated herein by reference.

Methods of Increasing Anti-Inflammatory Properties or Decreasing Effector Function/Cytotoxicity The invention also comprises a method of increasing the anti-inflammatory properties of an Fc-containing polypeptide comprising: selecting a parent Fc-containing polypeptide that is useful in treating an inflammatory condition (for example, an antibody or immunoadhesin that binds to an antigen that is involved in inflammation) and introducing mutations at positions 243, 264, 267 and 328 of the Fc-containing polypeptide, wherein the numbering is according to the EU index as in Kabat, wherein the Fc-containing polypeptide has increased anti-inflammatory properties when compared to the parent Fc-containing polypeptide. In one embodiment, the Fc-containing polypeptide comprises mutations F243A, V264A, S267E, and L328F. In one embodiment, the parent Fc-containing polypeptide is an antibody, antibody fragment or immunoadhesin that binds to an antigen that is involved in inflammation. In one embodiment, the parent Fc-containing polypeptide is an an antibody, antibody fragment or immunoadhesin that is already marketed or under development for the treatment of an inflammatory conditions. In another embodiment, the parent Fc-containing polypeptide is an antibody selected from the group consisting of: Muromonab-CD3 (anti-CD3 receptor antibody), Abciximab (anti-CD41 7E3 antibody), Rituximab (anti-CD20 antibody), Daclizumab (anti-CD25 antibody), Basiliximab (anti-CD25 antibody), Palivizumab (anti-RSV (respiratory syncytial virus) antibody), Infliximab (anti-TNFα antibody), Trastuzumab (anti-Her2 antibody), Gemtuzumab ozogamicin (anti-CD33 antibody), Alemtuzumab (anti-CD52 antibody), Ibritumomab tiuxeten (anti-CD20 antibody), Adalimumab (anti-TNFα antibody), Omalizumab (anti-IgE antibody), Tositumomab-131I (iodinated derivative of an anti-CD20 antibody), Efalizumab (anti-CD11a antibody), Cetuximab (anti-EGF receptor antibody), Golimumab (anti-TNFα antibody), Bevacizumab (anti VEGF-A antibody), Natalizumab (anti α4 integrin), Efalizumab (anti CD11a), Cetolizumab (anti-TNFα antibody), Tocilizumab (anti-IL-6R), Ustenkinumab (anti IL-12/23), alemtuzumab (anti CD52), and natalizumab (anti α4 integrin), and variants thereof. In another embodiment, the parent Fc-containing polypeptide is an Fc-fusion protein selected from the group consisting of: Arcalyst/rilonacept (IL1R-Fc fusion), Orencia/abatacept (CTLA-4-Fc fusion), Amevive/alefacept (LFA-3-Fc fusion), Anakinra-Fc fusion (IL-1Ra-Fc fusion protein), etanercept (TNFR-Fc fusion protein), FGF-21-Fc fusion protein, GLP-1-Fc fusion protein, RAGE-Fc fusion protein, ActRIIA-Fc fusion protein, ActRIIB-Fc fusion protein, glucagon-Fc fusion protein, oxyntomodulin-Fc-fusion protein, GM-CSF-Fc fusion protein, EPO-Fc fusion protein, Insulin-Fc fusion protein, proinsulin-Fc fusion protein and insulin precursor-Fc fusion protein, and analogs and variants thereof.

The invention also comprises a method of reducing the effector function of an Fc-containing polypeptide, comprising introducing mutations at positions 243, 264, 267 and 328 of a parent Fc-containing polypeptide, wherein said Fc containing polypeptide has decreased effector function when compared to the parent Fc-containing polypeptide, wherein the numbering is according to the EU index as in Kabat. In one embodiment, the Fc-containing polypeptide comprises mutations F243A, V264A, S267E, and L328F. In one embodiment, the Fc-containing polypeptide is an antibody or antigen binding fragment thereof. In one embodiment, the effector function is ADCC. In another embodiment, the effector function is CDC.

The invention also comprises a method of decreasing cytotoxicity of an Fc-containing polypeptide comprising: selecting a parent Fc-containing polypeptide that is useful in treating an inflammatory condition (for example, an antibody or immunoadhesin that binds to an antigen that is involved in inflammation) that binds to an antigen that is involved in inflammation and introducing mutations at positions 243, 264, 267 and 328 of the Fc-containing polypeptide, wherein the numbering is according to the EU index as in Kabat, wherein the Fc-containing polypeptide has decreased cytotoxicity when compared to the parent Fc-containing polypeptide. In a embodiment, the Fc-containing polypeptide comprises mutations F243A, V264A, S267E, and L328F.

In one embodiment, the parent Fc-containing polypeptide comprises a native Fc region. In another embodiment, the parent Fc-containing polypeptide comprises a F243A mutation. In another embodiment, the parent Fc-containing polypeptide comprises a V264A mutation. In another embodiment, the parent Fc-containing polypeptide comprises a F243A/V264A mutation.

Methods of Treatment

The invention also comprises a method of treating an inflammatory condition in a subject in need thereof comprising: administering to the subject a therapeutically effective amount of an Fc-containing polypeptide comprising mutations at positions 243, 264, 267 and 328, wherein the numbering is according to the EU index as in Kabat. In one embodiment, the Fc-containing polypeptide comprises mutations F243A, V264A, S267E, and L328F. In one embodiment, the Fc-containing polypeptide is an antibody fragment comprising SEQ ID NO:7. In another embodiment, the Fc-containing polypeptide is an antibody fragment comprising SEQ ID NO:8. In another embodiment, the Fc-containing polypeptide of the invention is an antibody fragment comprising SEQ ID NO:17. In another embodiment, the Fc-containing polypeptide is an antibody fragment consisting (or consisting essentially of) SEQ ID NO:7 or SEQ ID NO:8 or SEQ ID NO:17. The Fc-containing polypeptide of the invention can be administered by any route. In one embodiment, the Fc-containing polypeptide is administered parenterally. In one embodiment, the Fc-containing polypeptide is administered subcutaneously.

In one embodiment, the inflammatory condition is unwanted inflammatory immune reactions.

In one embodiment, the inflammatory condition is an autoimmune disease. In one embodiment, the inflammatory condition will be multiple sclerosis. In one embodiment, the inflammatory condition is systemic lupus erythematosus. In one embodiment, the inflammatory condition is type I diabetes.

In one embodiment, the inflammatory condition is a primary immunodeficiency syndrome, including congenital agammaglobulinaemia and hypogammaglobulinaemia, common variable immunodeficiency, severed combined immunodeficiency, or Wiskott Aldrich syndrome.

In one embodiment, the inflammatory condition is a secondary immunodeficiency syndrome, including B-cell lymphocytic leukemia, HIV infection or an allogeneic bone marrow transplantation.

In one embodiment, the inflammatory condition is idiopathic thrombocytopenic purpura.

In one embodiment, the inflammatory condition is multiple myeloma.

In one embodiment, the inflammatory condition is Guillain-Barre syndrome.

In one embodiment, the inflammatory condition is Kawasaki disease.

In one embodiment, the inflammatory condition is chronic inflammatory demyelinating polyneropathy (CIDP).

In one embodiment, the inflammatory condition is autoimmune nuetropenia.

In one embodiment, the inflammatory condition is hemolytic anemia.

In one embodiment, the inflammatory condition is anti-Factor VIII autoimmune disease.

In one embodiment, the inflammatory condition is multifocal neuropathy.

In one embodiment, the inflammatory condition is systemic vasculitis (ANCA positive).

In one embodiment, the inflammatory condition is polymyositis.

In one embodiment, the inflammatory condition is dermatomyositis.

In one embodiment, the inflammatory condition is antiphospholipid syndrome.

In one embodiment, the inflammatory condition is sepsis syndrome.

In one embodiment, the inflammatory condition is graft-v-host disease.

In one embodiment, the inflammatory condition is allergy.

In one embodiment, the inflammatory condition is an anti-Rhesus factor D reaction.

In one embodiment, the inflammatory condition is systemic lupus eythematusus (SLU).

In one embodiment, the inflammatory condition is an inflammatory condition of the cardiovascular system. The Fc-containing polypeptides of the invention may be used to treat atherosclerosis, atherothrombosis, coronary artery hypertension, acute coronary syndrome and heart failure, all of which are associated with inflammation.

In one embodiment, the inflammatory condition is an inflammatory condition of the central nervous system. In another embodiment, the inflammatory condition will be an inflammatory condition of the peripheral nervous system. For example, the Fc-containing polypeptides of the invention may be used for the treatment of, e.g., Alzheimer's disease, amyotrophic lateral sclerosis (a.k.a. ALS; Lou Gehrig's disease), ischemic brain injury, prion diseases, and HIV-associated dementia.

In one embodiment, the inflammatory condition is an inflammatory condition of the gastrointestinal tract. For example, the Fc-containing polypeptides of the invention may be used for treating inflammatory bowel disorders, e.g., Crohn's disease, ulcerative colitis, celiac disease, and irritable bowel syndrome.

In one embodiment, the inflammatory condition is psoriasis, atopic dermatitis, arthritis, including rheumatoid arthritis, osteoarthritis, and psoriatic arthritis.

In one embodiment, the inflammatory condition is steroid-dependent atopic dermatitis.

In one embodiment, the inflammatory condition is cachexia.

Examples of other inflammatory disorders that can be treated using the Fc-containing polypeptides of the invention also include: acne vulgaris, asthma, autoimmune diseases, chronic prostatitis, glomerulonephritis, hypersensitivities, pelvic inflammatory disease, reperfusion injury, sarcoidosis, transplant rejection, vasculitis, interstitial cystitis and myopathies.

In one embodiment, the Fc-containing polypeptide of the invention will be administered a dose of between 1 to 100 milligrams per kilograms of body weight. In one embodiment, the Fc-containing polypeptide of the invention will be administered a dose of between 0.001 to 10 milligrams per kilograms of body weight. In one embodiment, the Fc-containing polypeptide of the invention will be administered a dose of between 0.001 to 0.1 milligrams per kilograms of body weight. In one embodiment, the Fc-containing polypeptide of the invention will be administered a dose of between 0.001 to 0.01 milligrams per kilograms of body weight.

Pharmaceutical Formulations

The invention also comprises pharmaceutical formulations comprising an Fc-containing polypeptide of the invention and a pharmaceutically acceptable carrier.

In one embodiment, the invention relates a pharmaceutical composition comprising an Fc-containing polypeptide, wherein at least 70% of the N-glycans on the Fc-containing polypeptide comprise an oligosaccharide structure selected from the group consisting of $NANA_{(1-4)}Gal_{(1-4)}GlcNAc_{(2-4)}Man_3GlcNAc_2$, wherein the Fc-containing polypeptide comprises mutations at amino acid positions 243, 264, 267 and 328 of the Fc region, wherein the numbering is according to the EU index as in Kabat. In one embodiment, the mutations are F243A/V264A/S267E/L328F. In one embodiment, the Fc-containing polypeptide is an antibody fragment comprising SEQ ID NO:7. In another embodiment, the Fc-containing polypeptide is an antibody fragment comprising SEQ ID NO:8. In another embodiment, the Fc-containing polypeptide of the invention is an antibody fragment comprising SEQ ID NO:17. In another embodiment, the Fc-containing polypeptide is an antibody fragment consisting (or consisting essentially of) SEQ ID NO:7 or SEQ ID NO:8 or SEQ ID NO:17. In one embodiment, at least 47 mole % of the N-glycans have the structure $NANA_2Gal_2GlcNAc_2Man_3GlcNAc_2$. In one embodiment, the sialic acid residues in the sialylated N-glycans are attached via an α-2,6 linkage. In one embodiment, the sialic acid residues in the sialylated N-glycans are attached via an α-2,6 linkage and there is no detectable level of an α-2,3 linked sialic acid. In one embodiment, the sialylated N-glycans will comprise no N-glycolylneuraminic acid (NGNA).

As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration.

Pharmaceutical Formulations of therapeutic and diagnostic agents may be prepared by mixing with acceptable carriers, excipients, or stabilizers in the form of, e.g., lyophilized powders, slurries, aqueous solutions or suspensions (see, e.g., Hardman et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In certain embodiments, the Fc-containing polypeptides of the invention can be administered by an invasive route such as by injection (see above). In some embodiments of the invention, the Fc-containing polypeptides of the invention, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

In certain embodiments, the Fc-containing polypeptides of the invention can be administered by an invasive route such as by injection (see above). In some embodiments of the invention, the Fc-containing polypeptides of the invention, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions of the invention may also be administered with a needleless hypodermic injection device; such as the devices disclosed in U.S. Pat. No. 6,620,135; 6,096,002; 5,399,163; 5,383,851; 5,312,335; 5,064,413; 4,941,880; 4,790,824 or 4,596,556.

The pharmaceutical compositions of the invention may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

Alternately, one may administer the antibody in a local rather than systemic manner, for example, via injection of the antibody directly into an arthritic joint, often in a depot or sustained release formulation. Furthermore, one may administer the antibody in a targeted drug delivery system, for example, in a liposome coated with a tissue-specific antibody, targeting, for example, arthritic joint or pathogen-induced lesion characterized by immunopathology. The liposomes will be targeted to and taken up selectively by the afflicted tissue.

The administration regimen depends on several factors, including the serum or tissue turnover rate of the therapeutic antibody, the level of symptoms, the immunogenicity of the therapeutic antibody, and the accessibility of the target cells in the biological matrix. Preferably, the administration regimen delivers sufficient therapeutic antibody to effect improvement in the target disease state, while simultaneously minimizing undesired side effects. Accordingly, the amount of biologic delivered depends in part on the particular therapeutic antibody and the severity of the condition being treated. Guidance in selecting appropriate doses of therapeutic antibodies is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. Preferably, a biologic that will be used is derived from the same species as the animal targeted for treatment, thereby minimizing any immune response to the reagent. In the case of human subjects, for example, chimeric, humanized and fully human Fc-containing polypeptides are preferred.

Fc-containing polypeptides can be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang et al., *New Engl. J. Med.* 349:427-434 (2003); Herold et al., *New Engl. J. Med.* 346:1692-1698 (2002); Liu et al., *J. Neurol. Neurosurg. Psych.* 67:451-456 (1999); Portielji et al., *Cancer Immunol. Immunother.* 52:133-144 (2003). In other embodiments, an Fc-containing polypeptide of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/kg subject.

As used herein, the terms "therapeutically effective amount", "therapeutically effective dose" and "effective amount" refer to an amount of an Fc-containing polypeptide of the invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the Fc-containing polypeptide sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Example 1

Strains and Reagents

*Escherichia coli* strains TOP10 or DH5α (Invitrogen, CA) were used for recombinant DNA work. Restriction endonucleases, DNA modification enzymes and PNGase F were obtained from New England Biolabs, Ipswich, Mass. Oligonucleotides were ordered from Integrated DNA Technologies, Coralville, Iowa.

Example 2

Construction of IgG1 Fc Muteins and *Pichia pastoris* Recombinant Expression Vector The preparation of double and quadruple Fc muteins of the 1F11 IgG1 monoclonal antibody in *Pichia pastoris* was carried out using the sequences and protocols listed below.

A. Heavy and Light Chains

The heavy and light chain sequences, SEQ ID NOS: 1 and 2, respectively, used for the preparation of the wildtype (parent) 1F11 monoclonal IgG1 antibody are as set forth below. The heavy chain sequence used for the preparation of the 1F11 double mutein antibody is set forth in SEQ ID NO:3. The heavy chain sequence used for the preparation of the 1F11 quadruple mutein antibody is shown in SEQ ID NO:4. All light chain sequence for all antibodies was the same. The heavy and light chains were codon optimized according to *Pichia pastoris* codon usage and synthesized by GenScript USA Inc. 860 Centennial Ave. Piscataway, N.J. 08854.

B. Signal Sequence

The signal sequence of an α-Mating Factor predomain was fused in frame to the 5' end of the light or heavy chain by PCR fusion. The sequence was codon optimized as described above. A Kozak sequence AAACG was added to the 5' end of the methionine and an EcoR1 site was added before the Kozak sequence for cloning purposes. The DNA sequence (SEQ ID NO: 5) and amino acid (SEQ ID NO: 6) translation are as shown below.

C. Recombinant Plasmids for Expression IgG1 and IgG1 Fc Muteins

The heavy and light chains with the fused signal sequence of IgG1 and its muteins were cloned under *Pichia pastoris* AOX1 promoter and in front of *S. cerevisiae* Cyc terminator, respectively. The expression cassette of the completed heavy and light chains was put together into the final expression vector. Genomic insertion into *Pichia pastoris* was achieved by linearization of the vector with Spe1 and targeted integration into the Trp2 site.

A summary of the plasmids used herein is given below in Table 1. A graphic representation of the final expression plasmid for the 1F11 quadruple Fc mutein is set forth in FIG. 1.

TABLE 1

| Plasmid | Description |
|---|---|
| pGLY9535 | 1F11 in wild type IgG1 expression plasmid |
| pGLY9543 | 1F11 in IgG1 F243A/V264A double mutein expression plasmid |
| pGLY8068 | 1F11 in IgG1 F243A/V264A/S267E/L328F quadruple mutein expression plasmid |

Example 3

Glycoengineered *Pichia* GFI5.0 and GFI6.0 Hosts for Producing 1F11 and its Fc Muteins Two different glycoengineered *Pichia* hosts were applied in this invention, GFI5.0 and GFI 6.0. Following the procedures disclosed in Gerngross, U.S. Pat. No. 7,029,872 and Gerngross, U.S. Pat. No. 7,449,308, one can construct vectors that are useful for genetically engineering lower eukaryotic host cells such that they are capable of expressing a desired polypeptide having a desired N-glycoform as the predominant species. GFI 5.0 and GFI6.0 strains were engineered from NRRL11430 (American Type Culture Collection (ATCC), P.O. Box 1549, Manassas, Va. 20108, USA) according to the methods described in Hamilton et al., *Science*, 313: 1441-1443 (2006) and Hamilton US 2006/0286637. The engineered *Pichia pastoris* strain GFI5.0 is capable of producing proteins with a biantennary N-glycan structure with terminal galactose. The genotype of the GFI5.0 strain used herein, YGLY17108, is as follows: ura5Δ::ScSUC2 och1Δ::lacZ bmt2Δ::lacZ/KlMNN2-2 mnn4L1Δ::lacZ/MmSLC35A3 pno1Δ::lacZ ADE1::lacZ/FB8/NA10/MmSLC35A3 his1::lacZ-URA5-lacZ/XB33/SpGALE/DmUGT arg1::HIS1/KD53/TC54PRO1::ARG1/AOX1-ScMFpreTrMNS1URA6-LmSTT3d. The genotype of the engineered *Pichia pastoris* strain GFI 6.0, YGLY17159, is as follows: ura5Δ::ScSUC2 och1Δ::lacZ bmt2Δ::lacZ/KlMNN2-2 mnn4L1Δ::lacZ/MmSLC35A3 pno1Δ mnn4Δ::lacZADE1:lacZ/NA10/MmSLC35A3/FB8his1Δ::lacZ/ScGAL10/XB33/DmUGTarg1Δ::HIS1/KD53/TC54bmt4Δ::lacZ bmt1Δ::lacZ bmt3Δ::lacZTRP2:ARG1/MmCST/HsGNE/HsCSS/HsSPS/MmST6-33ste13Δ::lacZ/TrMDS1 dap2Δ::Nat$^R$TRP5:Hyg$^R$MmCST/HsGNE/HsCSS/HsSPS/MmST6-33 Vps10-1Δ::AOX1p_LmSTT3d pGAPDH-mPomGnT1-56. YGLY17159 is capable of producing proteins with a biantennary N-glycan structure on which terminal α2,6-linked sialic acid is attached to galactose.

The abbreviations used to describe the genotypes are commonly known and understood by those skilled in the art, and include the following abbreviations:
ScSUC2 *S. cerevisiae* Invertase
OCH1 Alpha-1,6-mannosyltransferase
K1MNN2-2 *K. lactis* UDP-GlcNAc transporter
BMT1 Beta-mannose-transfer (beta-mannose elimination)
BMT2 Beta-mannose-transfer (beta-mannose elimination)
BMT3 Beta-mannose-transfer (beta-mannose elimination)
BMT4 Beta-mannose-transfer (beta-mannose elimination)
MNN4L1 MNN4-like 1 (charge elimination)
MmSLC35A3 Mouse homologue of UDP-GlcNAc transporter
PNO1 Phosphomannosylation of N-glycans (charge elimination)
MNN4 Mannosyltransferase (charge elimination)
ScGAL10 UDP-glucose 4-epimerase
XB33 Truncated HsGalT1 fused to ScKRE2 leader
DmUGT UDP-Galactose transporter
KD53 Truncated DmMNSII fused to ScMNN2 leader
TC54 Truncated RnGNTII fused to ScMNN2 leader
NA10 Truncated HsGNTI fused to PpSEC12 leader
FB8 Truncated MmMNS1A fused to ScSEC12 leader
TrMDS1 Secreted *T. reseei* MNS1
ADE1 N-succinyl-5-aminoimidazole-4-carboxamide ribotide (SAICAR) synthetase
MmCST Mouse CMP-sialic acid transporter
HsGNE Human UDP-GlcNAc 2-epimerase/N-acetylmannosamine kinase
HsCSS Human CMP-sialic acid synthase
HsSPS Human N-acetylneuraminate-9-phosphate synthase
MmST6-33 Truncated Mouse alpha-2,6-saiIyl transferase fused to ScKRE2 leader
LmSTT3d Catalytic subunit of oligosaccharyltransferase from *Leishmania major*

Example 4

Yeast Transformation and Screening

The glycoengineered GFI5.0 and GS6.0 strains were grown in YPD rich media (yeast extract 1%, peptone 2% and 2% dextrose), harvested in the logarithmic phase by centrifugation, and washed three times with ice-cold 1 M sorbitol. One to five μg of a Spe1 digested plasmid was mixed with competent yeast cells and electroporated using a Bio-Rad Gene Pulser Xcell™ (Bio-Rad, 2000 Alfred Nobel Drive, Hercules, Calif. 94547) preset *Pichia pastoris* electroporation program. After one hour in recovery rich media at 24° C., the cells were plated on a minimal dextrose media (1.34% YNB, 0.0004% biotin, 2% dextrose, 1.5% agar) plate containing 300 μg/ml Zeocin and incubated at 24° C. until the transformants appeared.

To screen for high titer strains, 96 transformants were inoculated in buffered glycerol-complex medium (BMGY) and grown for 72 hours followed by a 24 hour induction in buffered methanol-complex medium (BMMY). Secretion of antibody was assessed by a Protein A beads assay as follows. Fifty micro liter supernatant from 96 well plate cultures was diluted 1:1 with 50 mM Tris pH 8.5 in a non-binding 96 well assay plate. For each 96 well plate, 2 ml of magnetic BioMag Protein A suspension beads (Qiagen, Valencia, Calif.) were placed in a tube held in a magnetic rack. After 2-3 minutes when the beads collected to the side of the tube, the buffer was decanted off. The beads were washed three times with a volume of wash buffer equal to the original volume (100 mM Tris, 150 mM NaCl, pH 7.0) and resuspended in the same wash buffer. Twenty μl of beads were added to each well of the assay plate containing diluted samples. The plate was covered, vortexed gently and then incubated at room temperature for 1 hour, while vortexing every 15 minutes. Following incubation, the sample plate was placed on a magnetic plate inducing the beads to collect to one side of each well. On the Biomek NX Liquid Handler (Beckman Coulter, Fullerton, Calif.), the supernatant from the plate was removed to a waste container. The sample plate was then removed from the magnet and the beads were washed with 100 μl wash buffer. The plate was again placed on the magnet before the wash buffer was removed by aspiration. Twenty μl loading buffer (Invitrogen E-PAGE gel loading buffer containing 25 mM NEM (Pierce, Rockford, Ill.)) was added to each well and the plate was vortexed briefly. Following centrifugation at 500 rpm on the Beckman Allegra 6 centrifuge, the samples were incubated at 99° C. for five minutes and then run on an E-PAGE high-throughput pre-cast gel (Invitrogen, Carlsbad, Calif.). Gels were covered with gel staining solution (0.5 g Coomassie G250 Brilliant Blue, 40% MeOH, 7.5% Acetic Acid), heated in a microwave for 35 seconds, and then incubated at room temperature for 30 minutes. The gels were de-stained in distilled water overnight. High titer colonies were selected for further Sixfors fermentation screening described in detail in Example 5. A summary of the IgG1 wild type and Fc mutein producing strains is given below in Table 2.

TABLE 2

| Strain | Description |
|---|---|
| YGLY21351 | GFI5.0 strain producing 1F11 IgG1 in GFI 5.0 |
| YGLY23258 | GFI6.0 strain producing 1F11 IgG1 F243A/V264A |
| YGLY25265 | GFI6.0 strain producing 1F11 IgG1F243A/V264A/S267E/L328F |
| YGLY25266 | |
| YGLY25267 | |
| YGLY25268 | |
| YGLY25269 | |

Example 5

Production of Antibody in Shake Flasks

The strains were cultivated in 500 ml shake flasks with 300 ml of 2% BMGY media and shaked at 24° C. for 3 days.
Protocol for Induction of Shake Flasks:
Collect the total volume of each culture (300 ml) into falcon tubes and spin at 2500 rpm for 5 minutes. Pour away supernatant and resuspend cell pellets in a final volume of 150 ml 2% BMMY and 360 ul PMTi4 (stock concentration 0.65 mg/ml). Transfer to a fresh 500 ml shake flask and shake at 24° C. for 2 days. Spin down the induced cultures and collect the supernatant into fresh falcon tubes.

The secreted antibodies were purified by protein A column using GE Healthcare, STREAMLINE rProtein A (catalog no. 17-1281-01) and BioRad poly-prep chromatography columns (10 ml) (catalog no. 731-1550). The following buffers were used:
Wash buffer #1: 20 mM Tris pH 7.0, 1M NaCl
Wash buffer #2: 20 mM Tris pH 7.0
Neutralization buffer: 1M Tris pH 8.0-pH 9.0
Elution buffer: 100 mM or 50 mM Sodium Citrate pH 3.0
Cleaning solution: 6M Urea in water.

The purification protocol is as follows:
Add 500 ul of STREAMLINE rProtein A beads to each BioRad column. The beads should be in 20% ethanol. The composition of the bead slurry should be 50% beads, 50% liquid.
Once the protein A beads are in the column they should be washed with 5 mls of Wash buffer #2 (discard the flow through)
Add 10 mls of supernatant to the BioRad column. During this step the antibodies will bind to the protein A beads. (discard the flow through)
Wash away undesired excess proteins by adding 5 mls of Wash buffer #1 to the column. (discard the flow through)
Wash the column again by adding 5 mls of Wash buffer #2 (discard the flow through)
Add 1 ml of Neutralization buffer to the 15 ml protein collection tube.
Place the BioRad column into the 15 ml collection tube.
Add 3 mls of Elution buffer to the BioRad column. This will remove the desired antibodies from the protein A beads.
Collect the eluted protein in the 15 ml protein collection tube.
Determine the concentration of the eluted protein by Bradford assay (use 10 ul of protein for Bradford assay).

Example 6

N-Linked Glycan Analysis by HPLC

To quantify the relative amount of each glycoform, the N-glycosidase F released glycans were labeled with 2-aminobenzidine (2-AB) and analyzed by HPLC as described in Choi et al., *Proc. Natl. Acad. Sci. USA* 100: 5022-5027 (2003) and Hamilton et al., *Science* 313: 1441-1443 (2006). Table 2 shows glycan profile of double mutein and quadruple mutein expression in GFI 6.0 host and 1F11 IgG1 in GFI 5.0 host. These strains were cultivated in shake flask. The results are shown in Table 2.

TABLE 2

| Glycan profile of 1F11 IgG1, IgG1 double mutein and IgG1 quadruple mutein | | | | | | | | | | |
|---|---|---|---|---|---|---|---|---|---|---|
| Strains | M4 | G0 | M5 | G1 | M6 | G2 | A1 | A1H | A2 | Sum |
| YGLY21351 | 0.3 | 12.9 | | 24.1 | 39.3 | 23.3 | | | | 100.0 |
| YGLY23258 | | 1.8 | 1.8 | 3.6 | | 24.6 | 32.7 | | 35.6 | 100.0 |
| YGLY25265 | | | | | | | | | | |
| YGLY25267 | | | | | | | 48.3 | 8.3 | 43.4 | 100.0 |
| YGLY25268 | 5.6 | | | | | 5.9 | 39.4 | | 41.4 | 100.0 |
| YGLY25269 | | | | | | 26.8 | 29.8 | | 38.2 | 100.0 |

Example 7

FcγR Binding Assay

Fcγ receptor binding assays were carried out as described (Shields, et al. (2001) *J. Biol. Chem.* 276:6591-6604) with minor modifications. High protein binding 96-well plates (Corning Costar) were coated with 100 μL per well of Fcγ receptor solutions in PBS at the following concentrations: 1 μg/mL for both FcγRI (R&D Systems) and FcγRIIa (*Pichia pastoris* produced), 2 μg/mL for FcγRIIb (*P. pastoris* produced), 0.8 μg/mL for FcγRIIIa-F158, and 0.4 μg/mL for FcγRIIIa-V158 (both *P. pastoris* produced). All *Pichia pastoris* produced receptors were expressed and purified as described (Li, et al. (2006) *Nature Biotechnology* 24:210-215). Monomeric antibody samples added to the FcγRI plate were serially diluted in assay diluent (1×PBS, 1% BSA, and 0.05% Tween20) and 100 μL per well was added to the plate. Antibody samples prepared for the remaining receptors require a one hour dimerization step with half molar ratio of goat anti-human IgG F(ab')2 F(ab')2 that is conjugated with alkaline phosphatase for detection. These dimerized F(ab')2/ antibody complexes were also serially diluted and 100 μL per well were added to the remaining receptor plates and all plates were incubated for one hour at room temperature. FcγRI bound sample antibody was detected using the same goat anti-human IgG F(ab')2 alkaline phosphatase conjugated F(ab')2. Sample antibody binding was quantified by measuring excitation at 340 nm and emission at 465 nm after 18 hour incubation with SuperPhos, 4-MUP Fluorescence AP Substrate Detection System (Virolabs).

Figure 3:
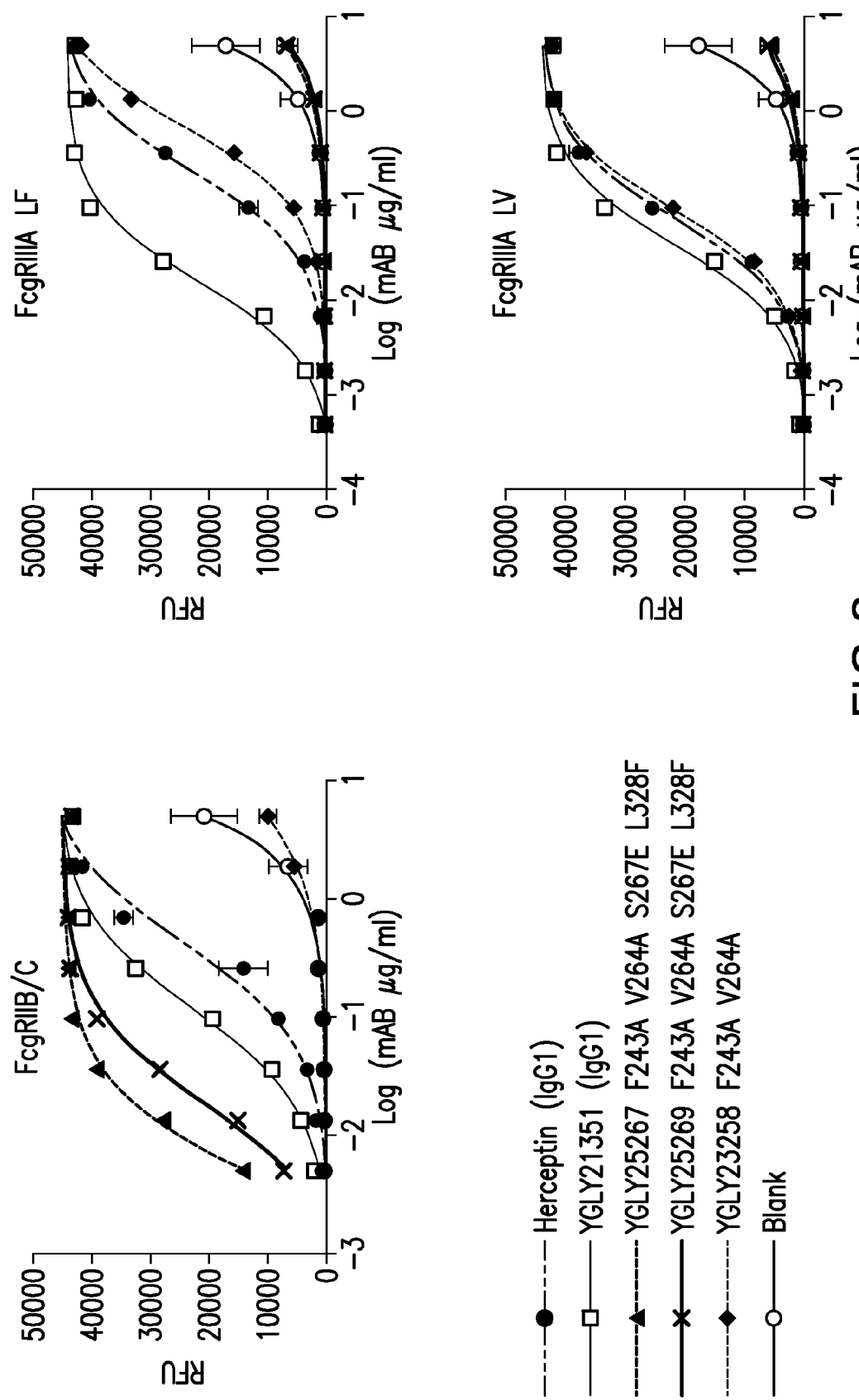
FIGS. 3-8 are graphic representations of the FcγR binding properties of the Fc-containing polypeptides of the invention.
Figure 5:
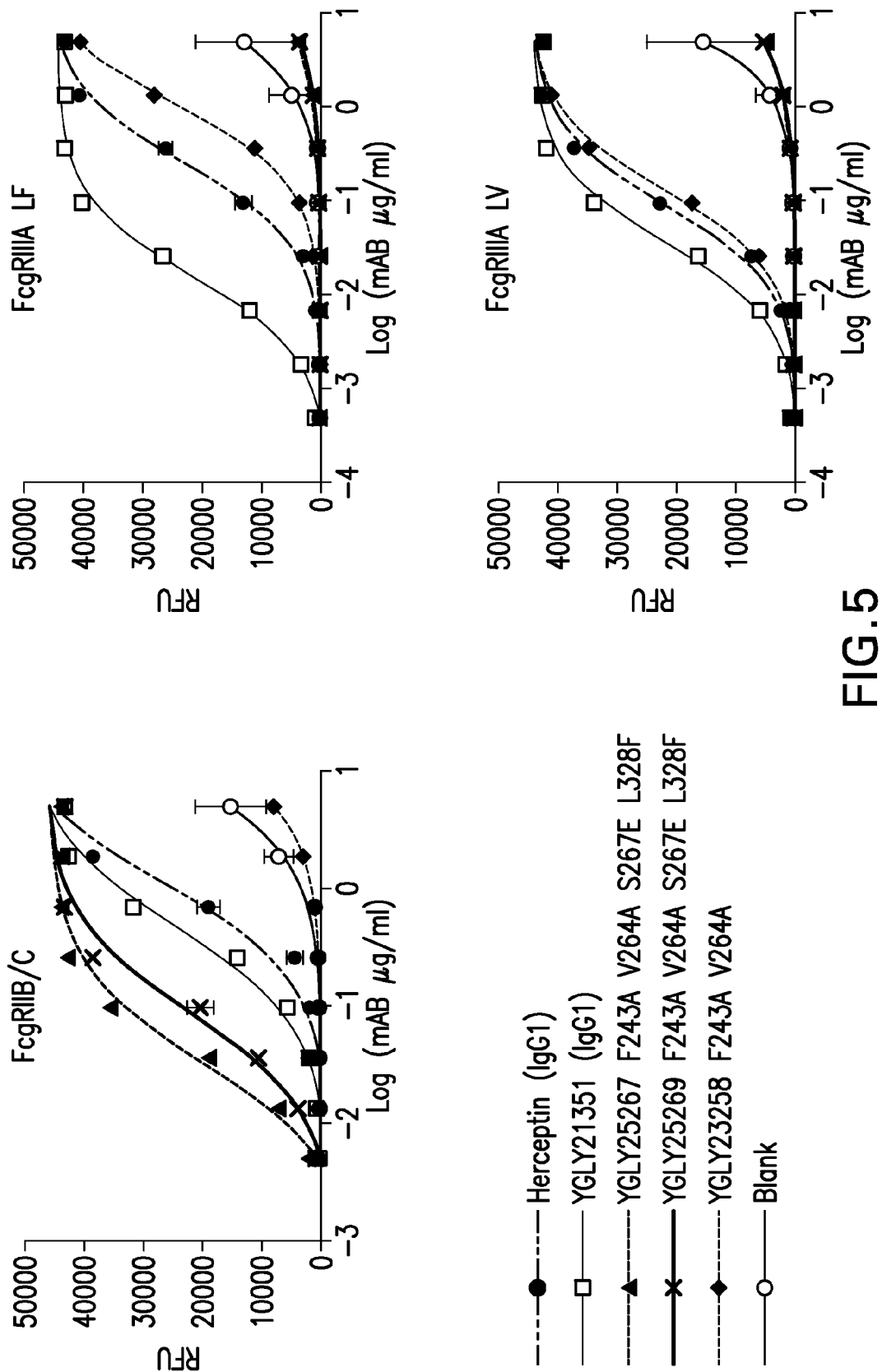
Figure 6:
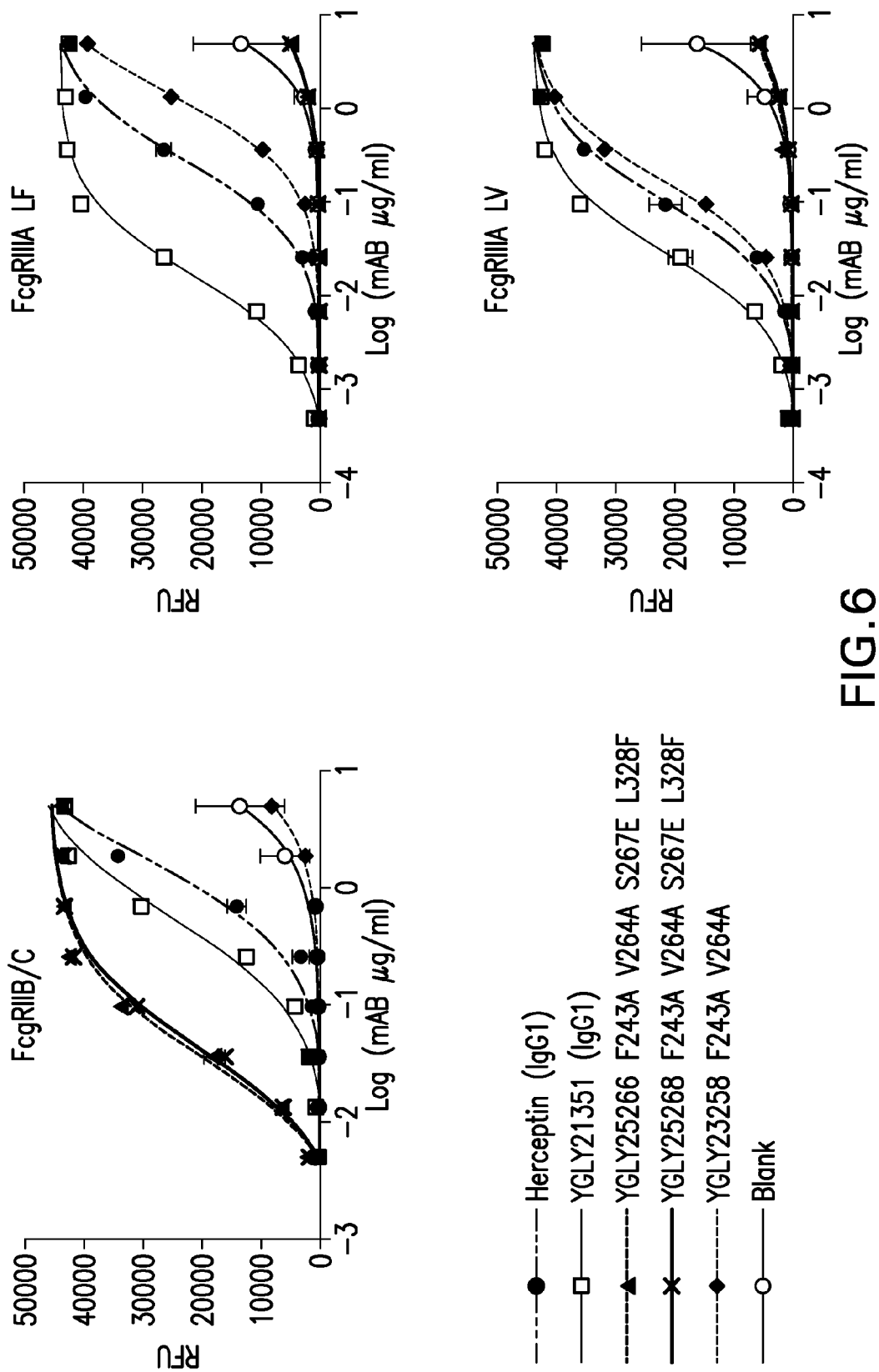
Figure 7:
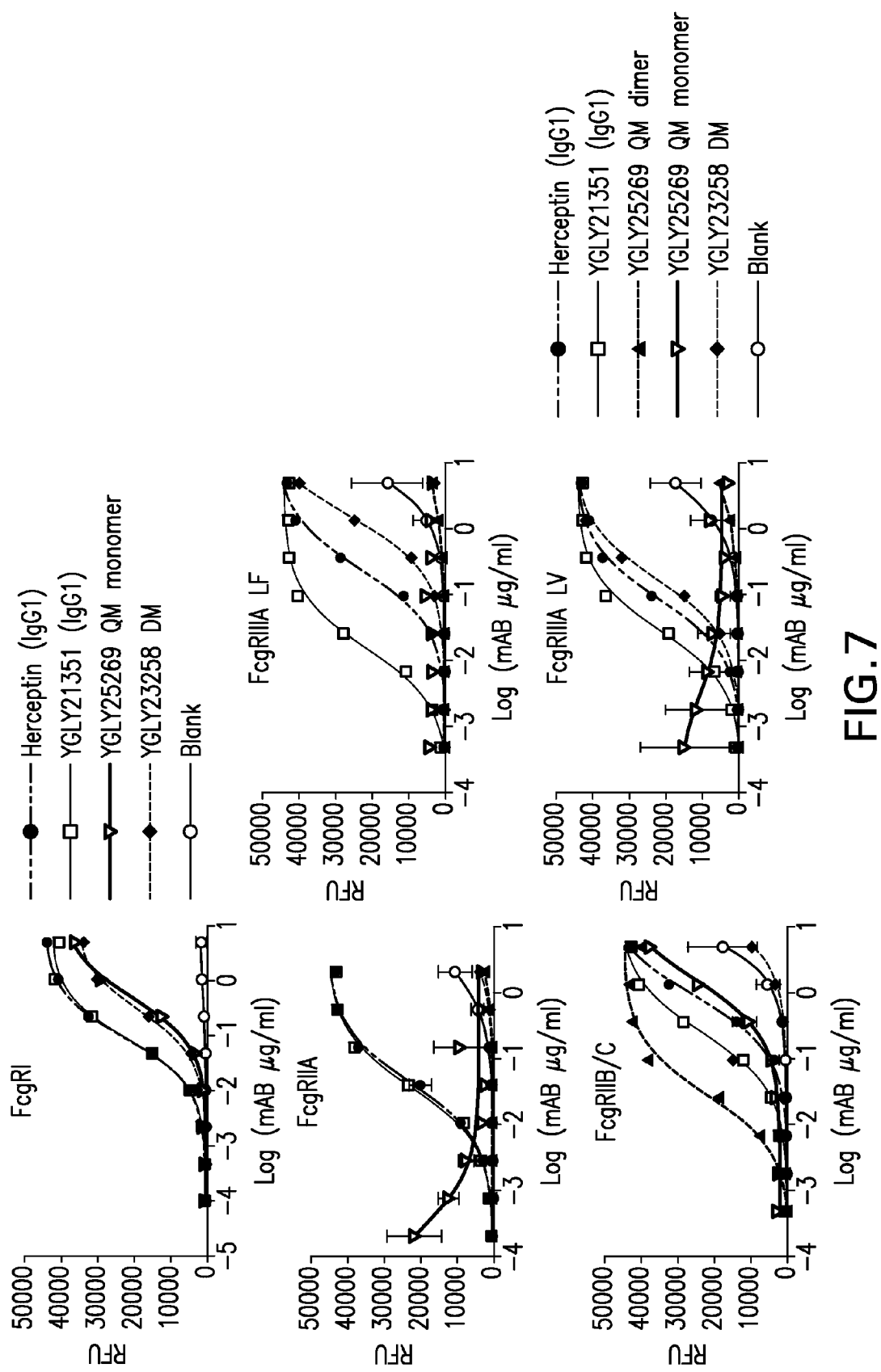

The results are shown in Tables 3-7. Each table represents the result of an individual experiment. A graphical representation of the data presented in Table 3, is found in FIG. 3. A graphical representation of the data presented in Table 4, is found in FIG. 4. A graphical representation of the data presented in Table 5, is found in FIG. 5. A graphical representation of the data presented in Table 6, is found in FIG. 6. A graphical representation of the data presented in Table 7, is found in FIG. 7.

TABLE 3

IC50 COMPARISON TABLE

| Samples | FcγRIIB | FcγRIIIA LF | FcγRIIIA LV |
|---|---|---|---|
| Herceptin (CHO; dimer) | 0.38 | 0.22 | 0.07 |
| YGLY21351 (dimer) | 0.12 | 0.02 | 0.04 |
| YGLY25269 (dimer) | 0.03 | no binding | no binding |
| YGLY25267 (dimer) | 0.01 | no binding | no binding |
| YGLY23258 (dimer) | no binding | 0.60 | 0.09 |

TABLE 4

IC50 COMPARISON TABLE

| Samples | FcγRIIB | FcγRIIIA LF | FcγRIIIA LV |
|---|---|---|---|
| Herceptin (CHO; dimer) | 0.54 | 0.21 | 0.09 |
| YGLY21351 (dimer) | 0.17 | 0.02 | 0.03 |
| YGLY25266 (dimer) | 0.02 | no binding | no binding |
| YGLY25268 (dimer) | 0.02 | no binding | no binding |
| YGLY23258(dimer) | no binding | 0.69 | 0.12 |

TABLE 5

IC50 COMPARISON TABLE

| Samples | FcγRIIB | FcγRIIIA LF | FcγRIIIA LV |
|---|---|---|---|
| Herceptin (CHO; dimer) | 0.43 | 0.24 | 0.09 |
| YGLY21351 (dimer)) | 0.18 | 0.02 | 0.04 |
| YGLY25269 (dimmer) | 0.03 | no binding | no binding |
| YGLY25267 (dimer) | 0.01 | no binding | no binding |
| YGLY23258 (dimer) | no binding | 0.94 | 0.13 |

TABLE 6

IC50 COMPARISON TABLE

| Samples | FcγRIIB | FcγRIIIA LF | FcγRIIIA LV |
|---|---|---|---|
| Herceptin (CHO; dimer) | 0.63 | 0.25 | 0.10 |
| YGLY21351(dimer)) | 0.20 | 0.02 | 0.03 |
| YGLY25266 (dimer) | 0.01 | no binding | no binding |

TABLE 6-continued

IC50 COMPARISON TABLE

| Samples | FcγRIIB | FcγRIIIA LF | FcγRIIIA LV |
|---|---|---|---|
| YGLY25268 (dimer) | 0.01 | no binding | no binding |
| YGLY23258 (dimer) | no binding | 1.17 | 0.16 |

TABLE 7

IC50 COMPARISON TABLE

| Samples | FcγRI | FcγRIIA | FcγRIIB | FcγRIIIA LF | FcγRIIIA LV |
|---|---|---|---|---|---|
| Herceptin (CHO; dimer) | 0.09 | 0.04 | 0.72 | 0.23 | 0.08 |
| YGLY21351 (dimer) | 0.08 | 0.04 | 0.23 | 0.02 | 0.03 |
| YGLY25269 (dimer) | 0.50 | no binding | 0.03 | no binding | no binding |
| YGLY25269 (monomer) | 0.42 | no binding | 1.26 | no binding | no binding |
| YGLY23258 (dimer) | 0.26 | no binding | no binding | 1.31 | 0.16 |

Figure 8:
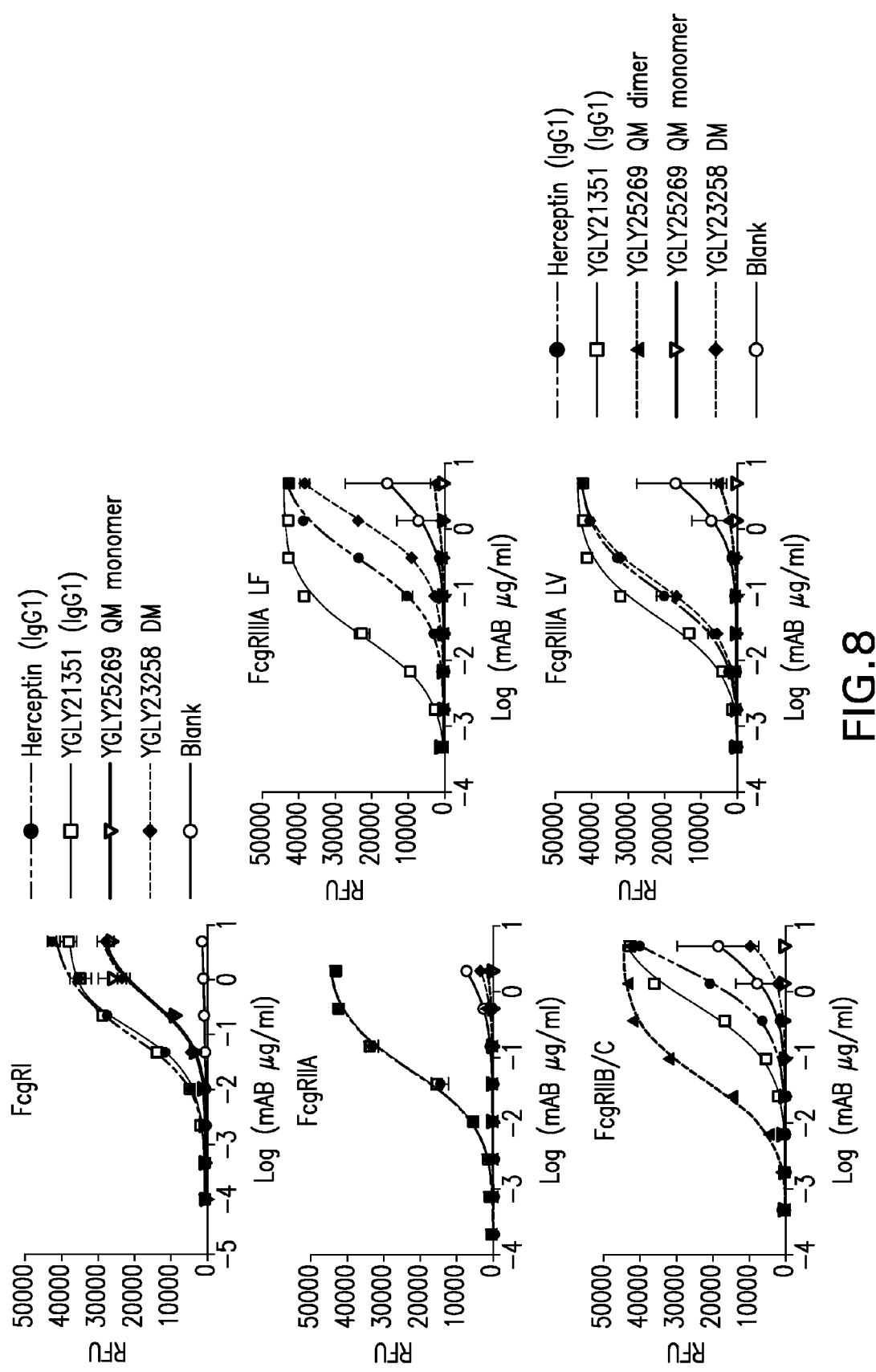

Table 8 summarizes the relative decrease in binding to the various receptors when compared to the wildtype parent antibody produced in GS 5.0. This data is also presented in FIG. 8.

TABLE 8

| Samples | FcγRI | FcγRIIA | FcγRIIB | FcγRIIIA LF | FcγRIIIA LV |
|---|---|---|---|---|---|
| IgG1 GS6.0 DM | ↓ 4 | no binding | no binding | ↓ 8-60 | ↓ 2-6 |
| IgG1 GS6.0 QM | ↓ 5-6 | no binding | ↑ 4-13 | no binding | no binding |

↓ indicates decreased affinity fold
↑ indicates increased affinity fold

Example 8

Antigen Affinity Assay

The binding affinity of the anti-PCSK9 antibodies of the invention was measured on a Biacore T100 instrument with a carboxymethylated dextran (CM5, cat# BR-1006-68) chip and 1×HBS-EP+ (10 mM HEPES, 150 mM NaCl, 3 mM EDTA, and 0.05% Surfactant P20) as the running buffer. The CM5 chip was immobilized on all flowcells with mouse anti-human IgG (Fc specific) according to the Biacore Human Antibody Capture Kit (Cat# BR-1008-39) to ~7000RU. Anti-PCSK9 antibodies were captured on the chip to ~500RU followed by analyte injections of wild-type human PCSK9 from 64.1 nM to 2.0 nM. Each flowcell was regenerated between each analyte injection with 3M MgCl for 40 seconds at 10 uL/min. Data was analyzed with Biacore T100 Evaluation Software using the 1:1 binding model using at least 5 point concentration range sensogram.

As shown in Table 9, antigen affinity for the various anti-PCSK9 antibodies made by the materials and methods herein are similar.

TABLE 9

| Samples | $k_a$ (1/M*s) Association Rate | $k_d$ (1/s) Dissociation Rate | $K_D$ (nM) Dissociation Constant | Average $K_D$ (nM) |
|---|---|---|---|---|
| 1F11 | 1.52E+05 | 4.99E-04 | 3.29 | 2.80 ± 0.70 |
| 1F11 | 1.77E+05 | 4.07E-04 | 2.30 | |
| YGLY25267-1 | 2.01E+05 | 6.34E-04 | 3.16 | |
| YGLY25267-2 | 1.93E+05 | 6.57E-04 | 3.41 | |
| YGLY25267-3 | 2.06E+05 | 6.61E-04 | 3.20 | 3.64 ± 0.4681 |
| YGLY25267-4 | 1.82E+05 | 7.79E-04 | 4.29 | |
| YGLY25267-5 | 1.94E+05 | 7.12E-04 | 3.68 | |
| YGLY25267-6 | 1.80E+05 | 7.37E-04 | 4.09 | |

Example 9

Construction, Expression and Characterization of Additional IgG1 Fc Muteins

Additional Fc muteins (Table 10) were constructed according to the methods of Example 2.

TABLE 10

| Strain | Parent | Expression Plasmid | Target | SEQ ID NO. (heavy chain/ light chain) |
|---|---|---|---|---|
| YGLY29110 | YGLY22834 | pGLY8068 | anti-PCSK9 1F11 QM | 4/2 |
| YGLY29111 | YGLY22834 | pGLY8068 | anti-PCSK9 1F11 QM | 4/2 |
| YGLY29105 | YGLY22834 | pGLY11555 | anti-IgE QM | 11/10 |
| YGLY29098 | YGLY22834 | pGLY11554 | anti-IgE DM | 9/10 |
| YGLY30176 | YGLY22834 | pGLY11515 | anti-TNF alpha QM | 12/13 |
| YGLY30177 | YGLY22834 | pGLY11515 | anti-TNF alpha QM | 12/13 |
| YGLY30178 | YGLY22834 | pGLY11515 | anti-TNF alpha QM | 12/13 |
| YGLY28722 | YGLY22834 | pGLY11539 | human IgG1 Fc ("hFc") QM | 8 |
| YGLY28725 | YGLY22834 | pGLY11539 | human IgG1 Fc ("hFc") QM | 8 |

The expression vectors containing the Fc muteins described in Table 10 were transformed in glycoengineered *Pichia pastoris* strain YGLY22834 (GFI6.0) which is capable adding alpha 2, 6 sialic acid onto bi-antennary galactoslyated glycan (G2). The genotype of the YGLY22834 strain used is as follows: ura5Δ::ScSUC2 och1Δ::lacZ bmt2Δ::lacZ/K1MNN2-2; mnn4L1Δ::lacZ/MmSLC35A3 pno1Δ mnn4Δ::lacZ; ADE1::lacZ/NA10/MmSLC35A3/FB8; his1Δ::lacZ/ScGAL10/XB33/DmUGT; arg1Δ::HIS1/KD53/TC54; bmt4Δ::lacZ bmt1Δ::lacZ bmt3Δ::lacZ; TRP2::ARG1/MmCST/HsGNE/HsCSS/HsSPS/MmST6-33; ste13Δ::lacZ-URA5-lacZ/TrMDS1 dap2Δ::NatR; TRP5::HygRMmCST/HsGNE/HsCSS/HsSPS/MmST6-33; vps10-1::pAOX1-LmSTT3d.

Fc mutein antibodies were produced and purified as indicated in Examples 4-5.

The glycosylation of the Fc muteins produced herein was quantified by HPLC as described in Example 6, and the results are shown in Table 11.

TABLE 11

Glycan profile of the Fc muteins described in Table 10.

| mAbs | Strains | Glycans | | | | | |
|---|---|---|---|---|---|---|---|
| | | G2 | A1 | A1H | A2 | Others | Sum |
| 1F11 QM | YGLY29110 | 1 | 10 | 3 | 84 | 2 | 100 |
| 1F11 QM | YGLY29111 | 1 | 13 | 5 | 75 | 5 | 100 |
| Anti-IgE QM | YGLY29105 | | 18 | 10 | 60 | 12 | 100 |
| Anti-IgEr DM | YGLY29098 | 6 | 30 | 5 | 54 | 4 | 100 |
| Anti-TNF QM | YGLY30176 | 1 | 9 | 4 | 83 | 2 | 100 |
| Anti-TNF QM | YGLY30177 | 2 | 14 | 7 | 60 | 15 | 100 |
| Anti-TNF QM | YGLY30178 | 3 | 21 | 5 | 67 | 3 | 100 |
| hFc QM | YGLY28722 | 2 | 19 | 8 | 66 | 2 | 100 |
| hFc QM | YGLY28725 | 5 | 15 | 3 | 63 | 14 | 100 |

The affinity of these Fc muteins towards the various FcγRs was measured as described in Example 7, and the results are shown in Tables 12 and 13.

The samples identified as "Anti-TNF IgG1 GS5" refers to an antibody comprising the heavy chain of SEQ ID NO:15 and the light chain of SEQ ID NO:13, produced in a recombinant *Pichia pastoris* strain GFI 5.0.

The samples identified as "1F11 IgG1 GS5.0" refers to an antibody comprising the heavy chain of SEQ ID NO:1, and the light chain of SEQ ID NO:2, produced in a recombinant *Pichia pastoris* strain GFI 5.0.

The sample identified as "Anti-TNF DM" refers to an antibody comprising the heavy chain of SEQ ID NO:16 and the light chain of SEQ ID NO:13, produced in a recombinant *Pichia pastoris* strain YGLY22834 (GFI6.0).

The sample identified as "1F11 DM" refers to an antibody comprising the heavy chain of SEQ ID NO:3 and the light chain of SEQ ID NO:2, produced in a recombinant *Pichia pastoris* strain YGLY22834 (GFI6.0).

The sample identified as "human IgG Fc DM" or "hFC DM" refers to a polypeptide comprising the amino acid sequence of SEQ ID NO:14 produced in a recombinant *Pichia pastoris* strain YGLY22834 (GFI6.0) according to the methods described above.

TABLE 12

| | Affinity (nM) | | | |
|---|---|---|---|---|
| Samples | FcγRIIIA LF (nM) ± STDEV | FcγRIIIA LV (nM) ± STDEV | FcγRIIA H (nM) ± STDEV | FcγRIIB (nM) ± STDEV |
| Anti-TNF IgG1 GS5.0 | 463 ± 16 | 53 ± 7 | 1053 ± 6 | 683 ± 52 |
| Anti-TNF DM | 3265 ± 440 | 195 ± 9 | 5558 ± 416 | 1552 ± 212 |
| Anti-TNF QM | 8067 ± 2984 | 5188 ± 1563 | 5927 ± 380 | 33 ± 8 |
| 1F11 IgG1 GS5.0 | 203 ± 14 | 0.15 ± 0.02 | 892 ± 26 | 545 ± 40 |
| 1F11 DM | 2517 ± 122 | 97 ± 6 | 11293 ± 2531 | 1693 ± 264 |
| 1F11 QM | 20967 ± 12115 | 5722 ± 1723 | 8147 ± 4875 | 29 ± 5 |
| hFcDM | 3473 ± 68 | 107 ± 11 | 10040 ± 628 | 2793 ± 300 |
| hFc QM | 30583 ± 813 | 6403 ± 203 | 9133 ± 556 | 28 ± 2 | n = 3
*Note-
any value reported greater than ~5000 nM should be intrepreted as a poor binder rather than relying on the actual value because these values are significantly outside the testing concentration range.

TABLE 13

Fold Changes in Affinity

| Samples | FcgRIIIA LF (nM) ± STDEV | FcgRIIIA LV (nM) ± STDEV | FcgRIIA H (nM) ± STDEV | FcgRIIB (nM) ± STDEV |
|---|---|---|---|---|
| Anti-TNF IgG1 GS5.0 | 1 | 1 | 1 | 1 |
| Anti-TNF DM | 7↓ | 4↓ | 5↓ | 2↓ |
| Anti-TNF QM | 17↓ | 98↓ | 6 | 21↑ |
| 1F11 IgG1 GS5.0 | 1 | 1 | 1 | 1 |
| 1F11 DM | 12↓ | 647↓ | 13↓ | 3↓ |
| 1F11 QM | 103 | >10000↓ | 9 | 19↑ |
| hFcDM | 1 | 1 | 1 | 1 |
| hFc QM | 9↓ | 59↓ | 1 | 100↑ |

↑ indicates decreased affinity fold
↓ indicates increased affinity fold

Example 10

Effect of the Fc Muteins in a Model of Immune Thrombocytopenia ("ITP")

ANIMALS: Fourteen (14) week old C57BL/6 female mice were obtained from Taconic Farms.

MODEL INDUCTION: The mice are dose with the reagents listed in Table 14 by intravenous (iv) infusion on day 0. After 24 hours, ITP is induced with a 2 μg iv dose of anti-CD41 antibody (MWReg30) obtained from BD Biosystems. Twentyfour (24) hours after ITP induction, platelet counts are done on whole blood samples using a Hemavet blood cell analyzer.

TABLE 14

| Group/Reagent | Strain | Dose (mpk) |
|---|---|---|
| hFc QM sialylated | YGLY28725 | 50 mpk |
| hFc QM asialylated | YGLY28725 | 50 mpk |
| hFc DM sialylated | YGLY30175 | 50 mpk |
| hFc DM asialylated | YGLY27893 | 50 mpk |
| GAMMAGARD | N/A | 1000 mpk |
| GAMMUNEX | N/A | 1000 mpk |

All Groups n = 4

Materials

The sample identified as ""hFC DM sialylated" refers to a polypeptide comprising the amino acid sequence of SEQ ID NO:14 produced in a recombinant *Pichia pastoris* strain YGLY22834 (GFI6.0)

The sample identified as ""hFC DM asialylated" refers to a polypeptide comprising the amino acid sequence of SEQ ID NO:14 produced in a recombinant *Pichia pastoris* strain YGLY22834 (GFI6.0), which was subsequently treated in vitro with neuramindase to produce an asialylated form of the protein with terminal galactose.

The sample identified as ""hFC QM sialylated" refers to a polypeptide comprising the amino acid sequence of SEQ ID NO:8 produced in a recombinant *Pichia pastoris* strain YGLY22834 (GFI6.0).

The sample identified as ""hFC QM asialylated" refers to a polypeptide comprising the amino acid sequence of SEQ ID NO:8 produced in a recombinant *Pichia pastoris* strain YGLY22834 (GFI6.0), which was subsequently treated in vitro with neuramindase to produce an asialylated form of the protein with terminal galactose.

In all cases the cultivation of the *Pichia pastoris* strains were performed in 15 L glass bioreactors. Briefly, two 3 L baffled seed flasks containing 500 mL of BSGY medium (4% glycerol, 1% yeast extract, 2% soytone, 100 mM potassium phosphate buffer, pH 6.5, 100 mM D-sorbitol, 1.34% yeast nitrogen base, and 4×10-5% biotin) were inoculated with yeast patches growing on agar plates. The flasks were incubated at 24° C. and 180 rpm for 48 h to ensure exponential growth when the cells were transferred to the bioreactor containing BSGY medium, at a 10% volumetric ratio. Temperature was controlled at 24° C., pH was controlled at 6.5 with 28% ammonium hydroxide, and dissolved oxygen (DO) was maintained at 20% of saturation at atmospheric pressure and 24° C. by fixing the airflow rate at 0.7 vvm and cascading agitation. Depletion of the initial 40 g $L^{-1}$ glycerol was detected by a rapid decrease in the oxygen uptake rate (OUR in mmol $L^{-1}h^{-1}$) and was followed by an exponential 50% glycerol feed, starting at 5.3 g $L^{-1}h^{-1}$ and increasing exponentially at a rate of 0.08 $h^{-1}$. After 8 h of glycerol fed-batch phase, the methanol induction in oxygen-limited environment was initiated. The DO cascade was turned off, and agitation was set to a setpoint of 460 rpm to achieve OUR of 20-25 mmol/L/h. After DO decreased to less than 1%, the first 1% (w/v) bolus shot of 100% methanol was delivered. All subsequent methanol 1% (w/v) bolus shots were triggered by rapid increases in DO indicating methanol depletion.

The samples ("hFC DM sialylated", "hFC DM asialylated", "hFC QM sialylated" and "hFC QM sialylated") were purified using MabSelect (from GE Healthcare Life Sciences).

The N-glycan analysis of the "hFC DM sialylated" and "hFC QM sialylated" samples was determined by HPLC, and had the following N-glycan characteristics:

| mAbs | Glycans | | |
|---|---|---|---|
| | A1 | A1H | A2 |
| hFC DM sialylated | 88 | 6 | 3 |
| hFC QM sialylated | 88 | 6 | 3 |

GAMMAGARD was obtained from Baxter Healthcare.

GAMMUNEX was obtained from by Talecris Biotherapeutics Inc.

The sample "ITP control" was anti-CD41 antibody (MWReg30) obtained from BD Biosystems.

Results

Figure 9:
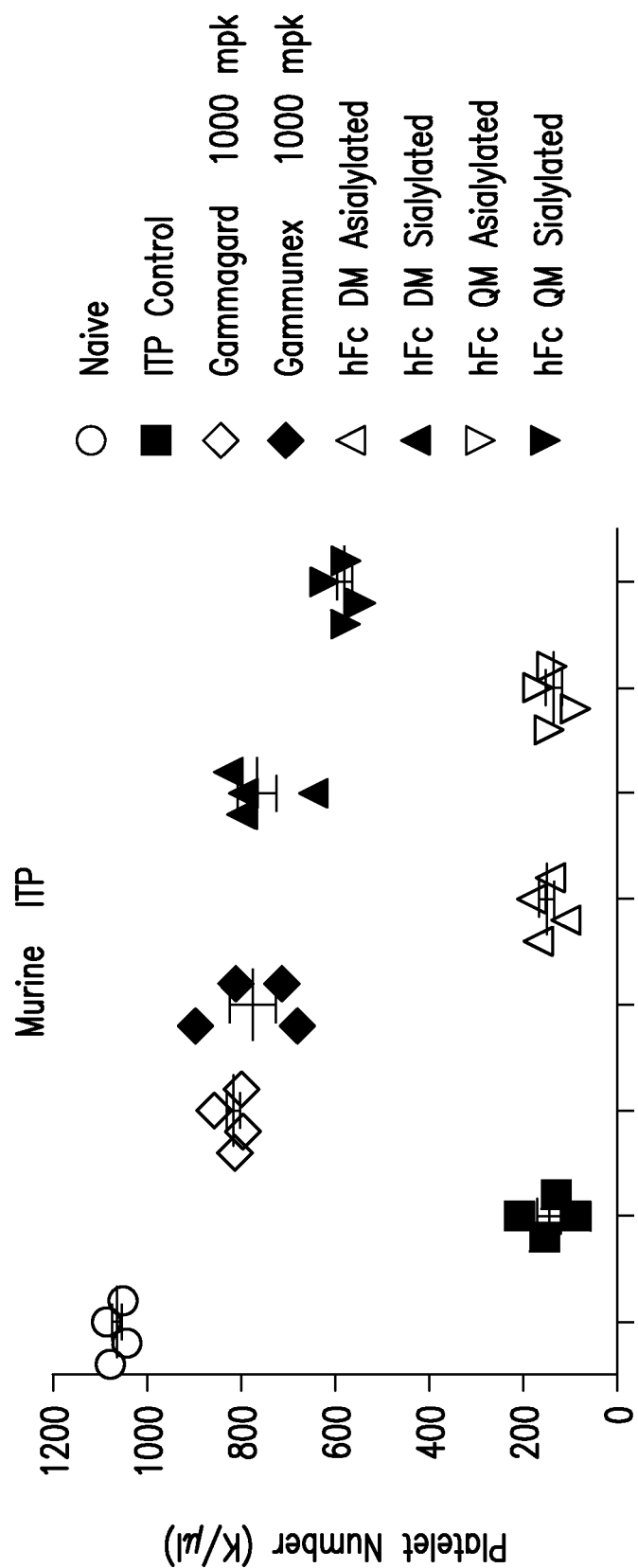
FIG. 9 shows the effect of some of the Fc polypeptides of the invention in a murine ITP model.

The platelets value obtained are listed in Table 15 (K/μL) and plotted in FIG. 9. hFc DM sialylated and hFc QM sialylated showed statistically significant protection from ITP by One-way Anova analysis.

| Naïve Cont | ITP Cont | GAMMAGARD | GAMMUNEX | hFc DM Asialylated | hFc DM Sialylated | hFc QM Asialylated | hFc QM Sialylated |
|---|---|---|---|---|---|---|---|
| 1051. | 208. | 857. | 713. | 109. | 795. | 169. | 545. |
| 1078. | 155. | 796. | 897. | 182. | 646. | 89. | 578. |
| 1043. | 130. | 799. | 811. | 168. | 827. | 139. | 622. |
| 1086. | 88. | 813. | 680. | 142. | 799. | 145. | 577. |

| SEQ ID NO | DESCRIPTION | SEQUENCE |
|---|---|---|
| 1 | Heavy chain (1F11 wt) | QVQLVQSGAEVKKPGASVKVSCKVSGYTFTDYYMNWVRQAPGQGLEWIG DINPNNGGAIYNQKFKGRATLTVDKSTSTAYMELRSLRSDDTAVYYCTS GIITEIAEDFWGQGTLVTV S S A S T K G P S V F P L A P S S K S T S G G T A A L G C L V K D Y F P E P V T V S W N S G A L T S G V H T F P A V L Q S S G L Y S L S S V V T V P S S S L G T Q T Y I C N V N H K P S N T K V D K K V E P K S C D K T H T C P P C P A P E L L G G P S V F L F P P K P K D T L M I S R T P E V T C V V V D V S H E D P E V K F N W Y V D G V E V H N A K T K P R E E Q Y N S T Y R V V S V L T V L H Q D W L N G K E Y K C K V S N K A L P A P I E K T I S K A K G Q P R E P Q V Y T L P P S R D E L T K N Q V S L T C L V K G F Y P S D I A V E W E S N G Q P E N N Y K T T P P V L D S D G S F F L Y S K L T V D K S R W Q Q G N V F S C S V M H E A L H N H Y T Q K S L S L S P G |
| 2 | Light chain (1F11) | DIQMTQSPSSLSASVGDRVTITCKASQNVGTNVVWYQQKPGKAPKALIH SASYRYSGVPSRFSGSGSGTDFTLTISSLQPEDFATYYCQQYKTYPYTF GQGTKVEIKRTVAAPSVFIFPPSDEQLKSGTASVVCLLNNFYPREAKVQ WKVDNALQSGNSQESVTEQDSKDSTYSLSSTLTLSKADYEKHKVYACEV THQGLSSPVTKSFNRGEC |
| 3 | Heavy chain (1F11 double mutein) | QVQLVQSGAEVKKPGASVKVSCKVSGYTFTDYYMNWVRQAPGQGLEWIG DINPNNGGAIYNQKFKGRATLTVDKSTSTAYMELRSLRSDDTAVYYCTS GIITEIAEDFWGQGTLVTVS S A S T K G P S V F P L A P S S K S T S G G T A A L G C L V K D Y F P E P V T V S W N S G A L T S G V H T F P A V L Q S S G L Y S L S S V V T V P S S S L G T Q T Y I C N V N H K P S N T K V D K K V E P K S C D K T H T C P P C P A P E L L G G P S V F L A P P K P K D T L M I S R T P E V T C V V A D V S H E D P E V K F N W Y V D G V E V H N A K T K P R E E Q Y N S T Y R V V S V L T V L H Q D W L N G K E Y K C K V S N K A L P A P I E K T I S K A K G Q P R E P Q V Y T L P P S R D E L T K N Q V S L T C L V K G F Y P S D I A V E W E S N G Q P E N N Y K T T P P V L D S D G S F F L Y S K L T V D K S R W Q Q G N V F S C S V M H E A L H N H Y T Q K S L S L S P G |
| 4 | Heavy chain (1F11 quadruple mutein) | QVQLVQSGAEVKKPGASVKVSCKVSGYTFTDYYMNWVRQAPGQGLEWIG DINPNNGGAIYNQKFKGRATLTVDKSTSTAYMELRSLRSDDTAVYYCTS GIITEIAEDFWGQGTLVTVS S A S T K G P S V F P L A P S S K S T S G G T A A L G C L V K D Y F P E P V T V S W N S G A L T S G V H T F P A V L Q S S G L Y S L S S V V T V P S S S L G T Q T Y I C N V N H K P S N T K V D K K V E P K S C D K T H T C P P C P A P E L L G G P S V F L A P P K P K D T L M I S R T P E V T C V V A D V E H E D P E V K F N W Y V D G V E V H N A K T K P R E E Q Y N S T Y R V V S V L T V L H Q D W L N G K E Y K C K V S N K A F P A P I E K T I S K A K G Q P R E P Q V Y T L P P S R D E L T K N Q V S L T C L V K G F Y P S D I A V E W E S N G Q P E N N Y K T T P P V L D S D G S F F L Y S K L T V D K S R W Q Q G N V F S C S V M H E A L H N H Y T Q K S L S L S P G |

| SEQ ID NO | DESCRIPTION | SEQUENCE |
|---|---|---|
| 5 | DNA sequence of signal sequence of an α-Mating Factor predomain | GAATTCGAAACGATGAGATTTCCTTCAATTTTTACTGCTGTTTTATTCG CAGCATCCTCCGCATTAGCT |
| 6 | Amino acid sequence of signal sequence of an α-Mating Factor predomain | MRFPSIFTAVLFAASSALA |
| 7 | Fc domain QM | TCPPCPAPELLGGPSVFLAPPKPKDTLMISRTPEVTCVVADVEHEDPEVKFNWYVDGVEVHNAKTKPREEQYNSTYRVVSVLTVLHQDWLNGKEYKCKVSNKAFPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 8 | Fc domain QM | AEPKSCDKTHTCPPCPAPELLGGPSVFLAPPKPKDTLMISRTPEVTCVVADVEHEDPEVKFNWYVDGVEVHNAKTKPREEQYNSTYRVVSVLTVLHQDWLNGKEYKCKVSNKAFPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 9 | Anti-IgE DM heavy chain | EVQLVESGGGLVQPGGSLRLSCAVSGYSITSGYSWNWIRQAPGKGLEWVASITYDGSTNYADSVKGRFTISRDDSKNTFYLQMNSLRAEDTAVYYCARGSHYFGHWHFAVWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLAPPKPKDTLMISRTPEVTCVVADVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPG |

-continued

| SEQ ID NO | DESCRIPTION | SEQUENCE | | | | | | | | | | | | |
|---|---|---|---|---|---|---|---|---|---|---|---|---|---|---|
| 10 | Anti-IgE light chain | D | I | Q | L | T | Q | S | P | S | S | L | S | A | S | V | G | D |
| | | R | V | T | I | T | C | R | A | S | Q | S | V | D | Y | D | G | D |
| | | S | Y | M | N | W | Y | Q | Q | K | P | G | K | A | P | K | L | L |
| | | I | Y | A | A | S | Y | L | E | S | G | V | P | S | R | F | S | G |
| | | S | G | S | G | T | D | F | T | L | T | I | S | S | L | Q | P | E |
| | | D | F | A | T | Y | Y | C | Q | Q | S | H | E | D | P | Y | T | F |
| | | G | Q | G | T | K | V | E | I | K | R | T | V | A | A | P | S | V |
| | | F | I | F | P | P | S | D | E | Q | L | K | S | G | T | A | S | V |
| | | V | C | L | L | N | N | F | Y | P | R | E | A | K | V | Q | W | K |
| | | V | D | N | A | L | Q | S | G | N | S | Q | E | S | V | T | E | Q |
| | | D | S | K | D | S | T | Y | S | L | S | S | T | L | T | L | S | K |
| | | A | D | Y | E | K | H | K | V | Y | A | C | E | V | T | H | Q | G |
| | | L | S | S | P | V | T | K | S | F | N | R | G | E | C | | | |
| 11 | Anti-IgE QM heavy chain | E | V | Q | L | V | E | S | G | G | G | L | V | Q | P | G | G | S |
| | | L | R | L | S | C | A | V | S | G | Y | S | I | T | S | G | Y | S |
| | | W | N | W | I | R | Q | A | P | G | K | G | L | E | W | V | A | S |
| | | I | T | Y | D | G | S | T | N | Y | A | D | S | V | K | G | R | F |
| | | T | I | S | R | D | D | S | K | N | T | F | Y | L | Q | M | N | S |
| | | L | R | A | E | D | T | A | V | Y | Y | C | A | R | G | S | H | Y |
| | | F | G | H | W | H | F | A | V | W | G | Q | G | T | L | V | T | V |
| | | S | S | A | S | T | K | G | P | S | V | F | P | L | A | P | S | S |
| | | K | S | T | S | G | G | T | A | A | L | G | C | L | V | K | D | Y |
| | | F | P | E | P | V | T | V | S | W | N | S | G | A | L | T | S | G |
| | | V | H | T | F | P | A | V | L | Q | S | S | G | L | Y | S | L | S |
| | | S | V | V | T | V | P | S | S | S | L | G | T | Q | T | Y | I | C |
| | | N | V | N | H | K | P | S | N | T | K | V | D | K | K | V | E | P |
| | | K | S | C | D | K | T | H | T | C | P | P | C | P | A | P | E | L |
| | | L | G | G | P | S | V | F | L | A | P | P | K | P | K | D | T | L |
| | | M | I | S | R | T | P | E | V | T | C | V | V | A | D | V | E | H |
| | | E | D | P | E | V | K | F | N | W | Y | V | D | G | V | E | V | H |
| | | N | A | K | T | K | P | R | E | E | Q | Y | N | S | T | Y | R | V |
| | | V | S | V | L | T | V | L | H | Q | D | W | L | N | G | K | E | Y |
| | | K | C | K | V | S | N | K | A | F | P | A | P | I | E | K | T | I |
| | | S | K | A | K | G | Q | P | R | E | P | Q | V | Y | T | L | P | P |
| | | S | R | D | E | L | T | K | N | Q | V | S | L | T | C | L | V | K |
| | | G | F | Y | P | S | D | I | A | V | E | W | E | S | N | G | Q | P |
| | | E | N | N | Y | K | T | T | P | P | V | L | D | S | D | G | S | F |
| | | F | L | Y | S | K | L | T | V | D | K | S | R | W | Q | Q | G | N |
| | | V | F | S | C | S | V | M | H | E | A | L | H | N | H | Y | T | Q |
| | | K | S | L | S | L | S | P | G | | | | | | | | | |
| 12 | Anti-TNF QM heavy chain | E | V | Q | L | V | E | S | G | G | G | L | V | Q | P | G | R | S |
| | | L | R | L | S | C | A | A | S | G | F | T | F | D | D | Y | A | M |
| | | H | W | V | R | Q | A | P | G | K | G | L | E | W | V | S | A | I |
| | | T | W | N | S | G | H | I | D | Y | A | D | S | V | E | G | R | F |
| | | T | I | S | R | D | N | A | K | N | S | L | Y | L | Q | M | N | S |
| | | L | R | A | E | D | T | A | V | Y | Y | C | A | K | V | S | Y | L |
| | | S | T | A | S | S | L | D | Y | W | G | Q | G | T | L | V | T | V |
| | | S | S | A | S | T | K | G | P | S | V | F | P | L | A | P | S | S |
| | | K | S | T | S | G | G | T | A | A | L | G | C | L | V | K | D | Y |
| | | F | P | E | P | V | T | V | S | W | N | S | G | A | L | T | S | G |
| | | V | H | T | F | P | A | V | L | Q | S | S | G | L | Y | S | L | S |
| | | S | V | V | T | V | P | S | S | S | L | G | T | Q | T | Y | I | C |
| | | N | V | N | H | K | P | S | N | T | K | V | D | K | K | V | E | P |
| | | K | S | C | D | K | T | H | T | C | P | P | C | P | A | P | E | L |
| | | L | G | G | P | S | V | F | L | A | P | P | K | P | K | D | T | L |
| | | M | I | S | R | T | P | E | V | T | C | V | V | A | D | V | E | H |
| | | E | D | P | E | V | K | F | N | W | Y | V | D | G | V | E | V | H |
| | | N | A | K | T | K | P | R | E | E | Q | Y | N | S | T | Y | R | V |
| | | V | S | V | L | T | V | L | H | Q | D | W | L | N | G | K | E | Y |
| | | K | C | K | V | S | N | K | A | F | P | A | P | I | E | K | T | I |
| | | S | K | A | K | G | Q | P | R | E | P | Q | V | Y | T | L | P | P |
| | | S | R | D | E | L | T | K | N | Q | V | S | L | T | C | L | V | K |
| | | G | F | Y | P | S | D | I | A | V | E | W | E | S | N | G | Q | P |
| | | E | N | N | Y | K | T | T | P | P | V | L | D | S | D | G | S | F |
| | | F | L | Y | S | K | L | T | V | D | K | S | R | W | Q | Q | G | N |
| | | V | F | S | C | S | V | M | H | E | A | L | H | N | H | Y | T | Q |
| | | K | S | L | S | L | S | P | G | | | | | | | | | |
| 13 | Anti-TNF QM light chain | D | I | Q | M | T | Q | S | P | S | S | L | S | A | S | V | G | D |
| | | R | V | T | I | T | C | R | A | S | Q | G | I | R | N | Y | L | A |
| | | W | Y | Q | Q | K | P | G | K | A | P | K | L | L | I | Y | A | A |
| | | S | T | L | Q | S | G | V | P | S | R | F | S | G | S | G | S | G |
| | | T | D | F | T | L | T | I | S | S | L | Q | P | E | D | V | A | T |

| SEQ ID NO | DESCRIPTION | SEQUENCE |
|---|---|---|
| | | Y Y C Q R Y N R A P Y T F G Q G T |
| | | K V E I K R T V A A P S V F I F P |
| | | P S D E Q L K S G T A S V V C L L |
| | | N N F Y P R E A K V Q W K V D N A |
| | | L Q S G N S Q E S V T E Q D S K D |
| | | S T Y S L S S T L T L S K A D Y E |
| | | K H K V Y A C E V T H Q G L S S P |
| | | V T K S F N R G E C |
| 14 | Fc domain DM | A E P K S C D K T H T C P P C P A P E L L G G P S V F L A P P K P K D T L M I S R T P E V T C V V A D V S H E D P E V K F N W Y V D G V E V H N A K T K P R E E Q Y N S T Y R V V S V L T V L H Q D W L N G K E Y K C K V S N K A L P A P I E K T I S K A K G Q P R E P Q V Y T L P P S R D E L T K N Q V S L T C L V K G F Y P S D I A V E W E S N G Q P E N N Y K T T P P V L D S D G S F F L Y S K L T V D K S R W Q Q G N V F S C S V M H E A L H N H Y T Q K S L S L S P G K |
| 15 | Anti-TNF heavy chain (wt) | EVQLVESGGGLVQPGRSLRLSCAASGFTFDDYAMHWVRQAPGKGL EWVSAITWNSGHIDYADSVEGRFTISRDNAKNSLY LQMNSLRAEDTAVYYCAKVSYLSTASSLDYWGQGTLVTVSSASTK GPSVFPLAPSSKSTSGGTAALGCLVKDYFPEPVTV SWNSGALTSGVHTFPAVLQSSGLYSLSSVVTVPSSSLGTQTYICN VNHKPSNTKVDKKVEPKSCDKTHTCPPCPAPELLG GPSVFLFPPKPKDTLMISRTPEVTCVVVDVSHEDPEVKFNWYVDG VEVHNAKTKPREEQYNSTYRVVSVLTVLHQDWLNG KEYKCKVSNKALPAPIEKTISKAKGQPREPQVYTLPPSRDELTKN QVSLTCLVKGFYPSDIAVEWESNGQPENNYKTTPP VLDSDGSFFLYSKLTVDKSRWQQGNVFSCSVMHEALHNHYTQKSL SLSPG |
| 16 | Anti-TNF DM heavy chain | E V Q L V E S G G G L V Q P G R S L R L S C A A S G F T F D D Y A M H W V R Q A P G K G L E W V S A I T W N S G H I D Y A D S V E G R F T I S R D N A K N S L Y L Q M N S L R A E D T A V Y Y C A K V S Y L S T A S S L D Y W G Q G T L V T V S S A S T K G P S V F P L A P S S K S T S G G T A A L G C L V K D Y F P E P V T V S W N S G A L T S G V H T F P A V L Q S S G L Y S L S S V V T V P S S S L G T Q T Y I C N V N H K P S N T K V D K K V E P K S C D K T H T C P P C P A P E L L G G P S V F L A P P K P K D T L M I S R T P E V T C V V A D V S H E D P E V K F N W Y V D G V E V H N A K T K P R E E Q Y N S T Y R V V S V L T V L H Q D W L N G K E Y K C K V S N K A L P A P I E K T I S K A K G Q P R E P Q V Y T L P P S R D E L T K N Q V S L T C L V K G F Y P S D I A V E W E S N G Q P E N N Y K T T P P V L D S D G S F F L Y S K L T V D K S R W Q Q G N V F S C S V M H E A L H N H Y T Q K S L S L S P G |
| 17 | Fc domain QM | E P K S C D K T H T C P P C P A P E L L G G P S V F L A P P K P K D T L M I S R T P E V T C V V A D V E H E D P E V K F N W Y V D G V E V H N A K T K P R E E Q Y N S T Y R V V S V L T V L H Q D W L N G K E Y K C K V S N K A F P A P I E K T I S K A K G Q P R E P Q V Y T L P P S R D E L T K N Q V S L T C L V K G F Y P S D I A V E W E S N G |

| SEQ ID NO | DESCRIPTION | SEQUENCE |
|---|---|---|
| | | Q P E N N Y K T T P P V L D S D G<br>S F F L Y S K L T V D K S R W Q Q<br>G N V F S C S V M H E A L H N H Y<br>T Q K S L S L S P G K |

While the present invention is described herein with reference to illustrated embodiments, it should be understood that the invention is not limited hereto. Those having ordinary skill in the art and access to the teachings herein will recognize additional modifications and embodiments within the scope thereof.

What is claimed:

1. An Fc-containing polypeptide comprising mutations at amino acid positions 243, 264, 267 and 328 of the Fc region, wherein the numbering is according to the EU index as in Kabat wherein the mutations are F243A, V264A, S267E, and L328F, and wherein the Fc region in the Fc-containing polypeptide is from an IgG.

2. The Fc-containing polypeptide of claim 1, comprising the amino acid sequence of SEQ ID NO:7, SEQ ID NO:8, or SEQ ID NO:17.

3. The Fc-containing polypeptide of claim 1, wherein said Fc-containing polypeptide is an antibody or an antibody fragment comprising sialylated N-glycans, wherein the sialic acid residues in the sialylated N-glycans are attached via α-2,6 linkages.

4. The Fc-containing polypeptide of claim 1, wherein said Fc-containing polypeptide is an antibody or an antibody fragment comprising sialylated N-glycans comprising a structure selected from $SA_{(1-4)}Gal_{(1-4)}GlcNAc_{(2-4)}Man_3GlcNAc_2$ or $SAGalGlcNAcMan_5GlcNAc_2$, wherein the sialic acid residues are attached via α-2,6 linkages.

5. The Fc-containing polypeptide of claim 1, wherein said Fc-containing polypeptide has one or more of the following properties when compared to a parent Fc-containing polypeptide:
   a) reduced effector function;
   b) increased anti-inflammatory properties;
   c) increased binding to a lectin;
   d) reduced binding to FcγRIIa;
   e) increased binding to FcγRIIb;
   f) reduced binding to FcγRIIIa;
   g) reduced binding to FcγRIIIb.

* * * * *